United States Patent
Chen et al.

(10) Patent No.: US 7,253,285 B2
(45) Date of Patent: Aug. 7, 2007

(54) THIAZOLINONE 4-MONOSUBSTITUTED QUINOLINES

(75) Inventors: Li Chen, Shanghai (CN); Shaoqing Chen, Bridgewater, NJ (US); Jianping Lou, Hillsborough, NJ (US); Achyutharao Sidduri, Livingston, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 157 days.

(21) Appl. No.: 11/214,153

(22) Filed: Aug. 29, 2005

(65) Prior Publication Data

US 2006/0063805 A1 Mar. 23, 2006

Related U.S. Application Data

(60) Provisional application No. 60/610,679, filed on Sep. 17, 2004.

(51) Int. Cl.
*C07D 417/06* (2006.01)

(52) U.S. Cl. .................................................... 546/135

(58) Field of Classification Search ................ 546/135; 548/190
See application file for complete search history.

(56) References Cited

FOREIGN PATENT DOCUMENTS

| EP | EP 1215208 A2 | 6/2002 |
| US | WO2004047760 A2 * | 6/2004 |
| WO | WO 2004/047760 A2 | 6/2004 |
| WO | WO 2005/011686 A1 | 2/2005 |

* cited by examiner

*Primary Examiner*—D. Margaret Seaman
*Assistant Examiner*—Nizal S. Chandrakumar
(74) *Attorney, Agent, or Firm*—George W. Johnston; Patricia S. Rocha-Tramaloni; David E. Wildman

(57) ABSTRACT

Thiazolinone monosubstituted quinoline derivatives where the quinoline ring is mono-substituted at the 4 positions which derivatives demonstrates CDK1 antiproliferative activity and are useful as anti-cancer agents.

80 Claims, No Drawings

THIAZOLINONE 4-MONOSUBSTITUTED QUINOLINES

PRIORITY TO RELATED APPLICATIONS

This application claims the benefit of Provisional Application Ser. No. 60/610,679, filed Sep. 17, 2004.

FIELD OF THE INVENTION

The field of this invention relates to thiazolinone monosubstituted quinoline derivatives where the quinoline ring is substituted at the 4-position, which derivatives demonstrates CDK1 antiproliferative activity and are useful as anti-cancer agents.

BACKGROUND OF THE INVENTION

Cyclin-dependent kinases (CDKs) are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. (See, e.g., the articles compiled in *Science*, 274:1643-1677 (1996); and *Ann. Rev. Cell Dev. Biol.*, 13:261-291 (1997)). CDK complexes are formed through association of a regulatory cyclin subunit (e.g., cyclin A, B1, B2, D1, D2, D3 and E) and a catalytic kinase subunit (e.g., CDK1, CDK2, CDK4, CDK5 and CDK6). As the name implies, the CDKs display an absolute dependence on the cyclin subunit in order to phosphorylate their target substrates, and different kinase/cyclin pairs function to regulate progression through specific phases of the cell-cycle.

As seen above, these protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

In view of the above properties, these kinases play an important part in the propagation of growth factor signal transduction that leads to cellular proliferation, differentiation and migration. Fibroblast growth factor (FGF) and vascular endothelial growth factor (VEGF) have been recognized as important mediators of tumor promoted angiogenesis. VEGF activates endothelial cells by signaling through two high affinity receptors, one of which is the kinase insert domain-containing receptor (KDR). (See, Hennequin L. F. et. al., *J. Med. Chem.* 45(6):1300 (2002). FGF activates endothelial cells by signaling through the FGF receptor (FGFR). Solid tumors depend upon the formation of new blood vessels (angiogenesis) to grow. Accordingly, inhibitors of the receptors FGFR and KDR that interfere with the growth signal transduction, and thus slow down or prevent angiogenesis, are useful agents in the prevention and treatment of solid tumors. (See, Klohs W. E. et. al., *Current Opinion in Biotechnology*, 10:544 (1999).

Because CDKs such as CDK1 serve as general activators of cell division, inhibitors of CDK1 can be used as antiproliferative agents. These inhibitors can be used for developing therapeutic intervention in suppressing deregulated cell cycle progression.

SUMMARY OF THE INVENTION

In accordance with this invention, it has been discovered that the compound of the formula:

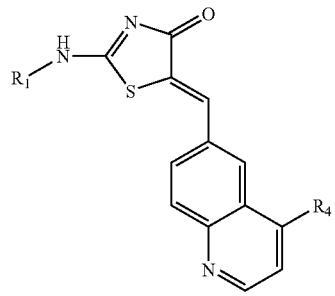

I wherein
R₁ is hydrogen, lower alkyl, aryloxy-lower alkyl, lower alkoxy-lower alkyl or

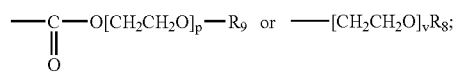

or R₂—(X)ₙ—
X is lower alkylene, hydroxyloweralkylene, cyclolower-alkylene, aryl lower alkylene, carboxyloweralkylene, hydroxy lower alkylene, amido lower alkylene, mono- or di-halo lower alkylene, amino lower alkylene, mono- or di-lower alkyl amino lower alkylene or imido lower alkylene
R₂ is

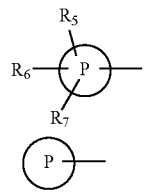

is an aryl ring, cyclolower alkyl ring containing from 3 to 6 carbon atoms, a 4 to 6 membered heterocycloalkyl ring containing from 3 to 5 carbon atoms and from 1 to 2 hetero atoms selected from the group consisting of oxygen, nitrogen and sulfur, or a 5 or 6 membered heteroaromatic ring containing from 1 to 2 hetero atoms selected from the group consisting of oxygen, sulfur and nitrogen;
R₅, R₆ and R₇ are independently selected from the group consisting of hydroxy, lower alkyl sulfone, hydroxy-lower alkyl, hydrogen, lower alkyl, halogen, perfluro lower alkyl, lower alkoxy, amino, mono- or di-lower alkyl amino, or when two of the substituents R₅, R₆ and R₇ are substituted on adjacent carbon atoms on ring these two substituents can be taken together with their adjacent, attached carbon atoms to form an aryl ring, a 3 to 6 membered cyclolower alkyl ring, a 4 to 6 membered heterocycloalkyl ring or a 4 to 6 membered heteroaromatic ring, said heterocycloalkyl ring and said heteroaromatic ring containing from 1 to 2 hetero atoms selected from the group consisting of oxygen, nitrogen or sulfur;

$R_4$ is halo,

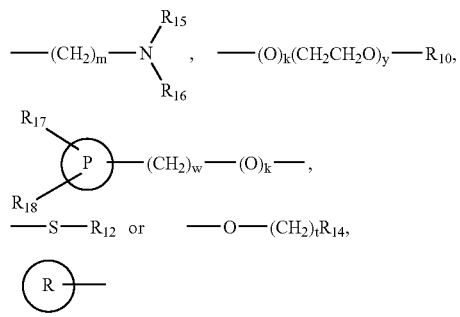

is an aryl ring, a cycloalkyl ring containing from 2 to 6 carbon atoms, a 4 to 6 membered heterocyclic alkyl ring containing from 1 to 2 hetero atoms selected from the group consisting of a oxygen, sulfur and nitrogen or a 5 to 6 numbered heteroaromatic right containing from 1 to 2 hetro atoms selected from the group consisting of oxygen, sulfur and nitrogen;

$R_8$, $R_9$, $R_{11}$, $R_{15}$ and $R_{16}$ are independently hydrogen or lower alkyl; $R_{10}$ and $R_{12}$ are loweralkyl;

$R_{14}$ is perfluro lower alkyl or $-N R_{15}R_{16}$;

$R_{17}$ and $R_{18}$ are independently hydrogen, lower alkyl, or $$-(CH_2)_z-\underset{\underset{O}{\|}}{C}-OR_{11};$$

n and k are integers from 0 to 1;
m, w, y and z are integers from 0 to 3;
p is an integer from 0 to 6; and
v and t are integers from 1 to 6;
or N-oxides of compounds where $R_2$ contains a nitrogen in the heteroaromatic ring, sulfones where $R_2$ contains a sulfur in the heterocycloalkyl ring or heteroaromatic ring;
or pharmaceutically acceptable salts thereof that inhibit the activity of CDKs, particularly, CDK1.

These inventive agents and pharmaceutical compositions containing such agents are useful in treating various diseases or disorder states associated with uncontrolled or unwanted cellular proliferation, such as cancer, autoimmune diseases, viral diseases, fungal diseases, neurodegenerative disorders and cardiovascular diseases.

Inhibiting and/or modulating the activity of CDKs, particularly CDK1, makes these compounds of formula and compositions containing these compounds useful in treating diseases medicated by kinase activity, particularly as anti-tumor agents in treating cancers.

DETAILED DESCRIPTION OF THE INVENTION

As pointed out herein, the compounds of formula I are potential anti-proliferation agents and are useful for mediating and/or inhibiting the activity of CDKs, particularly CDK1, thus providing anti-tumor agents for treatment of cancer or other diseases associated with uncontrolled or abnormal cell proliferation.

Among the preferred compounds of formula I are the compounds of the formula:

I-A wherein $R_1'$ is hydrogen, a lower alky, or lower alkoxy-lower alkyl and $R_4$ is as above, or pharmaceutically acceptable salts thereof, and compounds of the formula:

I-B wherein $R_1''$ is $R'_2-(X')_n-$;

n and $R_4$ are as above, and

X' is lower alkylene, hydroxyloweralkylene, cyclolower alkylene, hydroxy lower alkylene, mono- or di-halo lower alkylene;

$R_2'$ is is an aryl ring, cycloalkyl ring containing from 2 to 6 carbon atoms, a 4 to 6 membered heterocycloalkyl ring containing from 3 to 5 carbon atoms and from 1 to 2 hetero atoms selected from the group consisting of oxygen, nitrogen and sulfur, a 5 or 6 membered heteroaromatic ring containing from 1 to 2 hetero atoms selected from the group consisting of oxygen, sulfur and nitrogen;

$R_5'$ and $R_6'$ are independently selected from the group consisting of hydroxy, lower alkyl sulfone, hydroxy-lower alkyl, hydrogen, lower alkyl, halogen, perfluoro lower alkyl, lower alkoxy, amino, mono- or di-lower alkyl amino;

or N-oxides of compounds where $R'_2$ contains a nitrogen in the heteroaromatic ring, sulfones where $R'_2$ contains a sulfur in the hetero ring or heteroaromatic ring;

or pharmaceutically acceptable salts thereof.

In compounds I and I-B, where $R_1$, $R_1"$, $R_2$ and X are substituents containing an aryl moiety, the preferred aryl moiety is phenyl. As used herein the halogen includes all four halogens such as chlorine, fluorine, bromine and iodine.

As used in the specification, the term "lower alkyl", alone or in combination, means a monovalent straight or branched-chain saturated hydrocarbon alkyl group containing from one to six carbon atoms, such as methyl, ethyl, n-propyl, isopropyl, n-butyl, sec-butyl, isobutyl, tert-butyl, n-pentyl, n-hexyl and the like.

The term "cycloalkyl" means a cyclolower alkyl substituent which designates a monovalent unsubstituted 3- to 6-membered saturated carbocyclic hydrocarbon ring. Among the preferred cycloalkyl substituents are cyclopropyl, cyclobutyl, cyclohexyl, etc.

The term "lower alkoxy" means a straight-chain or branched-chain alkoxy group formed from lower alkyl containing form one to six carbon atoms, such as methoxy, ethoxy, n-propoxy, isopropoxy, n-butoxy, tert-butoxy and the like.

The term "aryl" means a monovalent mono- or bicyclic unsubstituted aromatic hydrocarbon ring such as phenyl or naphthyl, with phenyl being preferred.

The term "heterocycloalkyl" refers to a 4 to 6 membered monocyclic saturated ring containing 3 to 4 carbon atoms and one or two hetero atoms selected from the group consisting of oxygen, nitrogen or sulfur. Among the preferred heterocyclic alkyl groups are included morpholinyl, tetrahydro, thiopyranyl or tetrahydro pyranyl.

The term "heteroaromatic ring" refers to a monovalent 5 or 6 membered monocyclic heteroaromatic ring containing from 4 to 5 carbon atoms and from 1 to 2 hetero atoms selected from the group consisting of oxygen, nitrogen or sulfur. Among the preferred heteroaromatic groups are included thiophenyl, thioazole, pyridinyl, furanyl, etc.

The term "lower alkylene" designates a divalent saturated straight or branch chain hydrocarbon substituent containing from one to six carbon atoms.

The term "carboxy lower alkylene" denotes a lower alkylene substituent as designated hereinbefore substituted, preferably monosubstituted, with a carboxy radical.

The term "hydroxy lower alkylene" designates a lower alkylene substituent substituted, preferably monosubstituted, with a hydroxy group where an amido lower alkylene is used, this designates a lower alkylene substituent as set forth hereinbefore substituted with an amido substituent.

The term "mono- or di-halo lower alkylene substituents" designate a lower alkylene substituent which is either monosubstituted or disubstituted on one or two carbon atoms in the lower alkylene chain.

The term "amino lower alkylene" designates a lower alkylene substituent which is substituted; preferably monosubstituted, with an amino group.

The term "amido lower alkylene" designates a lower alkylene substituent as hereinbefore defined substituted on one position with an amido group. The amino group on the amino lower alkylene may be substituted by 1 or 2 lower alkyl groups. In the case of one lower alkyl group substitution, the term "mono-lower alkyl amino" is used. In the case of two lower alkyl substituents on the nitrogen atom of the amine group, the substituent is a "di-lower alkyl amino group."

The term "aryloxy" designates an aryloxy substituent where aryl is as above. The preferred aryl group is phenyl and the preferred aryloxy is phenoxy.

The term "perfluoro-lower alkyl" means any lower alkyl group wherein all the hydrogens of the lower alkyl group are substituted or replaced by fluorine. Among the preferred perfluoro-lower alkyl groups are trifluoromethyl, pentafluoroethyl, heptafluoropropyl, etc with trifluoromethyl being especially preferred.

The term "pharmaceutically acceptable salts" refers to conventional acid-addition salts or base-addition salts that retain the biological effectiveness and properties of the compounds of formulas I, II, III, IV and V and are formed from suitable non-toxic organic or inorganic acids, or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et al., *Pharmaceutical Dosage Forms and Drug Delivery Systems* (6th Ed. 1995) at pp. 196 and 1456-1457.

In accordance with this invention, the compounds of formula I can be prepared from a compound of the formula:

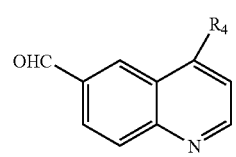

II wherein $R_4$ is as above.

The compound of formula II is converted to the compound of formula I via the following reaction scheme.

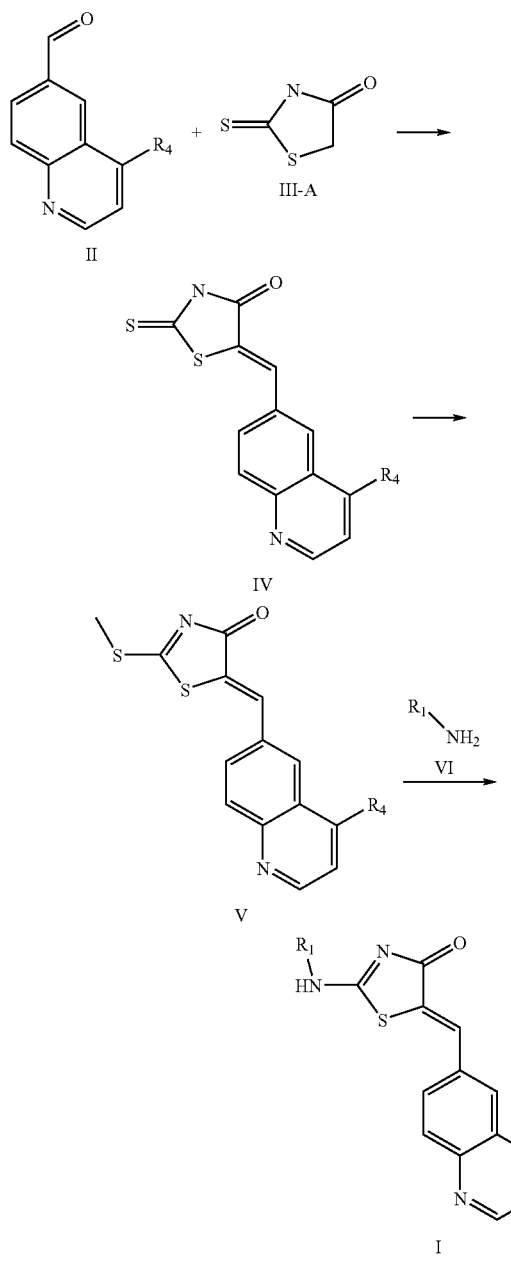

wherein

R₁ and R₄ are as above.

In accordance with this invention, the compound of formula II is reacted with the compound of formula III-A [rhodanine (2-thio-4-thiazolin-4-one)] via a Knoevenegel reaction to produce the compound of formula IV. Any of the conditions conventional in carrying out Knoevenegel reaction can be utilized in carrying out this condensation. Generally, this reaction is carried out at reflux temperature in the presence of alkali metal acetate and acetic acid. In the next step of this synthesis, the resulting substituted thiazolidine of formula IV is treated with a methylating agent to methylate the thio group on the compound of formula IV to produce the compound of formula V. The preferred methylating agent is iodomethane. This reaction is carried out in an organic amine base such as diisopropylethylamine (DIEA).

In carrying out this reaction, temperature and pressure are not critical and this reaction can be carried out at room temperature and atmospheric pressure. In fact in carrying out this reaction, any of the conditions conventional in methylating a thio group can be used.

In the next step of this synthesis, the compound of formula V is reacted with the compound of formula VI to produce the compound of formula I. The compound of formula VI is an amine and any means conventionally used in amine substitution by a methylthio group can be used in carrying out this reaction. In accordance with one embodiment this substitution is carried out by reacting the compound of formula VI with the compound of formula V in the presence of a conventional solvent such as acetonitrile. Generally, this reaction is carried out in the presence of an amine base such as diisopropylethylamine.

On the other hand, the compound of formula I can be prepared by reacting the compound of formula II with a compound of the formula:

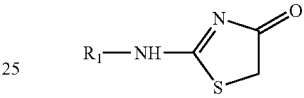

wherein R₁ is as above.

The reaction of the compound of formula VII with the compound of formula II to produce the compound of formula I, is carried out in a high boiling organic solvent such as benzene or toluene at high temperature from 100° C. to 200° C. in a closed system. In this manner, this reaction is carried out under high temperatures and pressure. The compound of formula VII can be directly formed by direct replacement thorough reacting the compound of the formula $$R_1-NH_2 \qquad VI$$

wherein R₁ is as above with a compound of the formula III-A. The replacement reaction is generally carried out in the presence of mercuric chloride. This reaction is carried out in an inert organic solvent. Any conventional inert organic solvent such as acetonitrile, methylene chloride, etc. can be utilized. In carrying out this reaction, an amine base, such as diisopropylethylamine, is used. In carrying out this reaction, temperature and pressure are not critical and this reaction can be carried out at room temperature and atmospheric pressure. In carrying out this reaction, any conventional method of replacing a sulfide group with an amine can be utilized.

In the compound of formula VI where R₁ is X and X is a hydroxy lower alkylene, these compounds can be prepared from the corresponding amino acids or amino acid esters by reduction with an alkali metal borohydride. On the other hand, these hydroxy lower alkylene compounds can be prepared for the corresponding cyano carboxylic acid esters by reduction with lithium aluminum hydride. Reduction reduces the cyano group to an amino group and the ester to a hydroxy group. This reduction should take place before reacting the compound of formula VI with the compound of formula V.

On the other hand, where in the compound of formula VI, R₁ is R₂X— and X is a carboxy lower alkylene, amido lower alkylene or imido lower alkylene, these compounds can be directly converted to the compound of formula I by reacting the corresponding compound of formula VI with the compound of formula V or the compound of formula III-A as described above.

Where the rings (P) or (R) is an N-oxide of a nitrogen atom in a nitrogen containing ring which forms the rings (P) or (R), these N-oxides can be formed from a tertiary ring nitrogen atom by oxidation. Any conventional method of oxidizing a tertiary nitrogen atom to an N-oxide can be utilized. The preferred oxidizing agent is metachloroperbenzoic acid (MCPBA).

In accordance with this invention, the compound of formula II can be produced by the following reaction scheme:

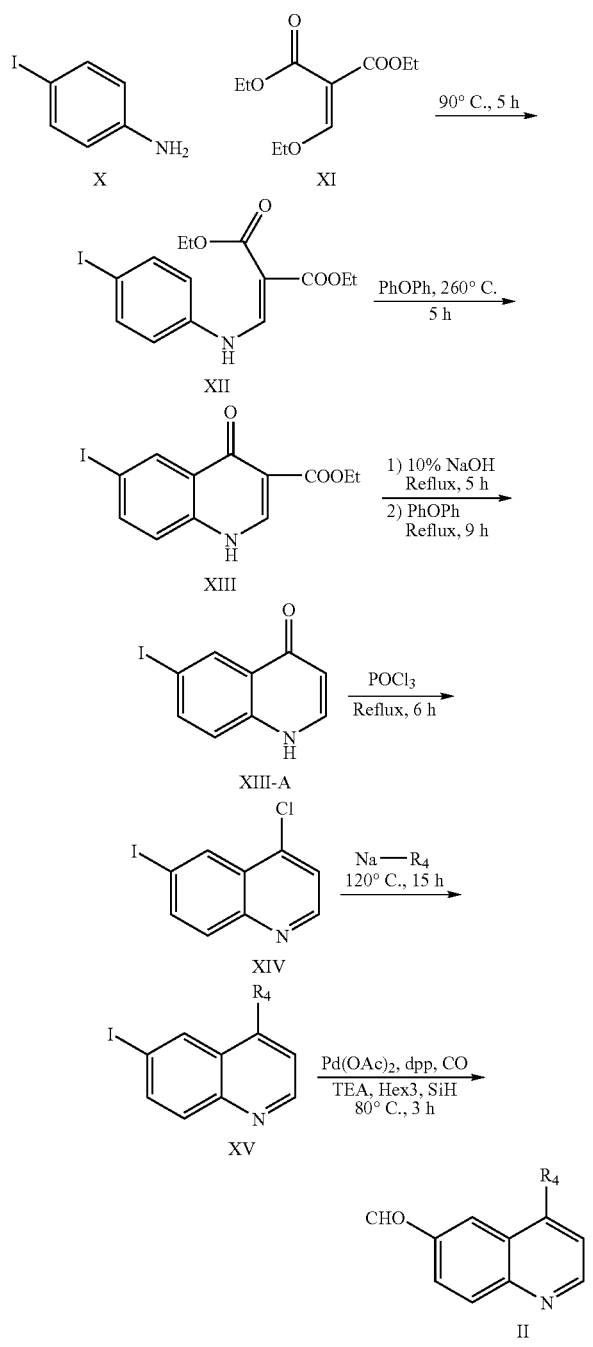

wherein $R_4$ is as above.

The ether ester of formula XI is condensed with iodoaniline, the compound of formula X, to produce the substituted amine of formula XIII. This reaction is conventional condensation reaction wherein substitution of an alpha beta unsaturated ether by an amine is achieved by condensation of the amine with an ether. Generally this reaction is carried out at temperatures of from 80° C. to 200° C. in a high boiling inert organic solvent. Any conventional high boiling inert organic solvent can be utilized in carrying out this reaction. Among the conventional high boiling inert organic solvent solvents that can be utilized for carrying out this reaction include toluene, benzene, etc. Generally, this reaction is carried out by refluxing for long periods of time, i.e. above five hours.

The compound of formula XII is converted to the compound of formula XIII by cyclization of the ester group in the compound of formula XIII. This cyclization is carried out by heating compound of formula XII temperatures of at least 200° C. generally from 200° C. to 300° C. in the presence of high boiling ether such as biphenyl ether. Compound of formula XIII is converted to the compound of formula XIII-A in two steps. In the first step, the compound of XIII is hydrolized with an aqueous alkali medal hydroxide such as sodium hydroxide or potassium hydroxide in an aqueous medium to give the carboxylic acid product. Similarly, this reaction is carried out under reflux conditions. In the second step of this reaction, the carboxylic acid product is heated to a temperature of 200° C. thoroughly from about 200° C. to 300° C. in the presence of a high boiling ether solvent such as biphenyl ether. In this manner, the compound of formula XIII-A is produced. An oxo group in the compound of formula XIII-A can be converted to the chlorinated compound of formula XIV by treatment with a chlorinating agent such as phosphorous oxychloride. In this manner, the reaction mixture can be refluxed to convert the oxo group into a halide with good yields. Any of the conditions conventional in converting the mercapto group to halide groups can be used in carrying out this reaction.

The compound of formula XIV is converted to the compound of formula XV by reacting the halogenated site of the compound of formula XIV with a sodium salt of the $R_4$ substituent one wishes to place at the 4-position of the compound of formula I. This reaction is carried out by heating the salt and the compound of formula XIV under high pressure in their corresponding alcohol solvent medium. Any conventional method of reacting a halogen group with a sodium salt can be utilized to carry out this reaction. In the last step of this synthesis, the compound of formula XV is converted to the compound of formula II using formylation reaction to convert the iodo group to the CHO substituent on the phenyl ring. This reaction can be carried out by reacting the compound of formula XV with carbon monoxide in the presence of diphenylpropyl phosphine (dpp) in the presence of a base utilizing a palladium acetate catalyst. In carrying out this reaction the carbon monoxide is added to the reaction medium under pressure generally from 70 to 80 psi at temperatures from 40° C. to 120° C. Any conventional method of converting a halide group to the aldehyde on a phenyl ring by the means of reaction with carbon monoxide can be utilized to convert the compound of formula XV to the compound of formula II.

In this reaction, $R_4$ is preferably —$(O)_k(CH_2CH_2O)_y$—$R_{10}$ or

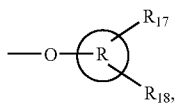

since these substituents easily form sodium salts which can react with the compound of formula XIV to produce compounds of formulae V, II, I, I-A, and I-B where $R_4$ is the above substituents.

In compound I and I-B where n is 1. When x is cyclolower alkylene, the preferred cyclolower alkylene is cyclopropylene. In the compounds of formula 1, I-A and I-B where the substituents for $R_1$ and $R_2$ are aryl rings the preferred ring is a phenyl which can be unsubstituted or substituted with this substituents defined as $R_5'$ and $R_6'$.

One embodiment of the compound of formula I-A are those compounds where $R_1$ is hydrogen. Among these class of compounds are those compounds where $R_4'$ is $—(O)_k(CH_2CH_2O)_y—R_{10}$ or $—O—(CH_2) R_{14}$. In the embodiment of the compounds of formula I-A where R' is hydrogen are those compounds where $R_4'$ is $—O—(CH_2) R_{14}$. In this embodiment, the compounds where $R_{14}$ is perfluorolower alkyl are preferred with the compounds where $R_{14}$ is trifluoromethyl group being especially preferred.

Another embodiment of this invention are the compounds of formula I-B where n is 1 and X' is a cyclolower alkylene group particularly cyclopropyl. Among the preferred compounds of this embodiment of formula I-B where X' is a cyclolower alkylene, are those compounds $R_2'$ is phenyl or halo-phenyl. In this preferred embodiment compounds where 4 is halo

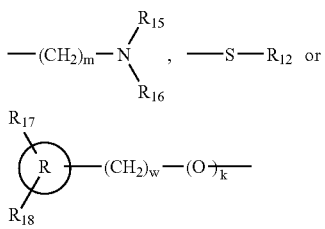

are especially preferred. With respect to those compounds of formula I-B where X is cyclolower alkylene particularly cyclopropyl, $R_2'$ is phenyl or halo-phenyl and $R_4$ is

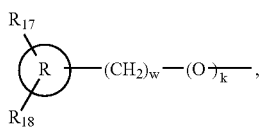

the preferred ring is phenyl, cycloalkyl or cycloheteroalkyl.

In accordance with another embodiment of the compound of formula I-B where n is I are those compounds where X is a lower alkylene substituent. This embodiment includes compounds where $R_1$ contains a phenyl ring which can be phenyl or substituted phenyl. In this class of compounds $R_4$ can be $—(O)_k(CH_2CH_2O)_y—R_{10}$, $—S—R_{12}$ or $—O—(CH_2)_t R_{14}$ Another class of compounds of formula I-B are those compounds where n is 1, X is a loweralkylene substituent and the ring P which forms $R_1'$ is a heteroaromatic ring. Among this class of compounds are included, those compounds where $R_4$ is $—(O)_k(CH_2CH_2O)_y—R_{10}$, halo or

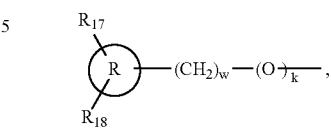

Again the preferred R ring of the substituent $R_4$ includes phenyl, cycloalkyl and cycloheteroalkyl rings. Another embodiment of compound of formula I-B, where n is 1 are those compounds where $R_1'$ is phenyl. Among the preferred compound included within this class of compounds are those compounds where $R_4$ is $—(O)_k(CH_2CH_2O)_y—R_{10}$ or

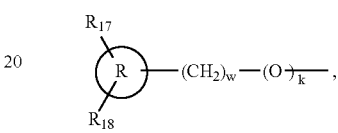

Another embodiment of the compound of formula I-B where n is 1 are those compounds where X' is a dihalo loweralkylene substituent. In this class of compounds is included those compounds where $R_1'$ is a heteroaromatic ring. In this preferred class of compounds $R_4$ is preferably $—(O)_k(CH_2CH_2O)_y—R_{10}$.

Pharmaceutical compositions according to the invention may, alternatively or in addition to a compound of Formula I, comprise as an active ingredient pharmaceutically acceptable prodrugs, pharmaceutically active metabolites, and pharmaceutically acceptable salts of such compounds and metabolites. Such compounds, prodrugs, multimers, salts, and metabolites are sometimes referred to herein collectively as "active agents" or "agents."

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the active agents of the invention may be used to treat diseases mediated by modulation or regulation of the protein kinases CDK1. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of CDK1 protein kinase includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The present invention is further directed to methods of modulating or inhibiting protein kinase CDK1 activity, for example in mammalian tissue, by administering the inventive agent. The activity of agents as anti-proliferatives is easily measured by known methods, for example by using whole cell cultures in an MTT assay. The activity of the inventive agents as modulators of CDK1 protein kinase activity may be measured by any of the methods available to those skilled in the art, including in vivo and/or in vitro assays. Examples of suitable assays for activity measurements include those described in International Publication No. WO 99/21845; Parast et al., Biochemistry, 37, 16788-16801 (1998); Connell-Crowley and Harpes, Cell Cycle: Materials and Methods, (Michele Pagano, ed. Springer, Berlin, Germany)(1995); International Publication No. WO 97/34876; and International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I and an inert, pharmaceutically acceptable carrier or diluent. In one embodiment of the pharmaceutical compositions, efficacious levels of the inventive agents are provided so as to provide therapeutic benefits involving anti-proliferative ability. By "efficacious levels" is meant levels in which proliferation is inhibited, or controlled. These compositions are prepared in unit-dosage form appropriate for the mode of administration, e.g., parenteral or oral administration.

An inventive agent can be administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methyl methacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent can be dissolved in an aqueous solution of an organic or inorganic acid. If a soluble salt form is not available, the agent may be dissolved in a suitable cosolvent or combinations of cosolvents.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage determination tests in view of the experimental data for an agent.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically. For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores.

EXAMPLES

Example 1

5-(4-Methoxy-quinolin-6-ylmeth-(Z)-ylidine)-2-[(thiophen-2-ylmethyl)-amino]-thiazol-4-one

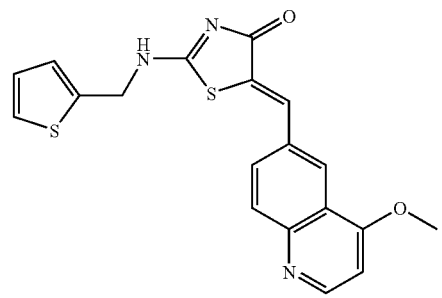

a) Preparation of 2-[(4-bromo-phenylamino)-methylene]-malonic acid diethyl ester

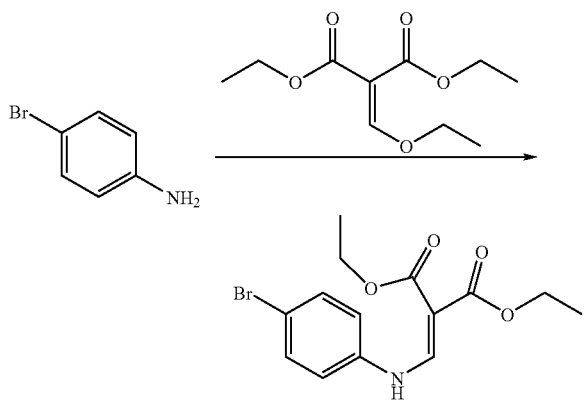

A mixture of 4-bromoaniline (100 g, 563.9 mmol) and 2-ethoxymethylene-malonic acid diethyl ester (126.9 g, 575 mmol) was heated to 90° C. Then, the resulting brown mixture was stirred for 5 h. After cooling to room temperature, the reaction mixture was diluted with ethanol (~200 mL) and cooled down in an ice-water bath to afford a hard solid. This mixture was then heated to break down the hard solid and also to remove most of the impurities. After cooling the suspension in the refrigerator, the solids were collected by filtration and washed with cold ethanol. After drying in air, 168 g (87% yield) of 2-[(4-bromo-phenylamino)-methylene]-malonic acid diethyl ester was isolated as a white solid: mp 100-102° C. (lit. 100-101° C.).

b) Preparation of 6-bromo-4-hydroxy-quinoline-3-carboxylic acid ethyl ester

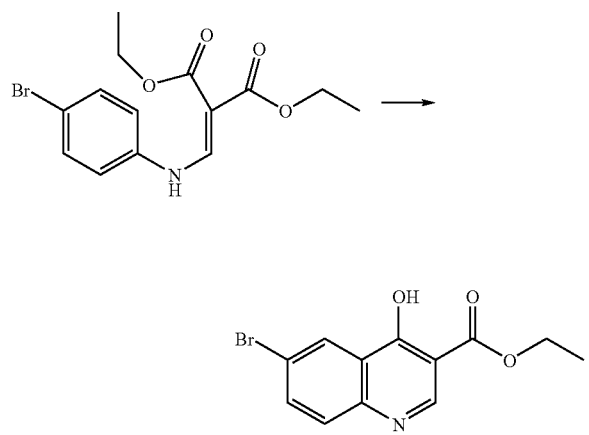

The solid 2-[(4-bromo-phenylamino)-methylene]-malonic acid diethyl ester (157 g, 458.8 mmol) was added to a hot diphenyl ether (260 g) and the mixture was heated to reflux for 5 h to afford a brown suspension. Then, the mixture was cooled to 100° C. and diluted with ethanol (~200 mL). This suspension was refluxed for 10 min and then cooled to room temperature. The solids were collected by filtration and washed with diethyl ether. After drying in air, 132.59 g (97.6% yield) of 6-bromo-4-hydroxy-quinoline-3-carboxylic acid ethyl ester was isolated as a white solid: EI-HRMS m/e calcd for $C_8H_6N_2O$ (M$^+$) 146.0480, found 146.0478.

c) Preparation of 6-bromo-4-hydroxy-quinoline-3-carboxylic acid

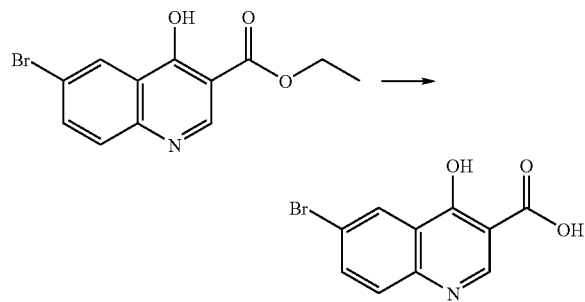

A suspension of 6-bromo-4-hydroxy-quinoline-3-carboxylic acid ethyl ester (102.59 g, 337.7 mmol) in 10% potassium hydroxide in water (689 mL) was heated to reflux for 5 h to afford a light brown solution. After cooling to room temperature, the undissolved solid particles were removed by filtration and the filtrate was extracted with dichloromethane to remove any neutral impurities. The aqueous layer was neutralized with 3.0N hydrochloric acid to afford a white precipitate. Then, the solids were collected by filtration and washed with water. After drying in air, 91 g (98% yield) of 6-bromo-4-hydroxy-quinoline-3-carboxylic acid was isolated as a white solid: EI-HRMS m/e calcd for $C_{10}H_6BrNO_3$ (M$^+$) 266.9531, found 266.9521.

d) Preparation of 6-bromo-quinolin-4-ol

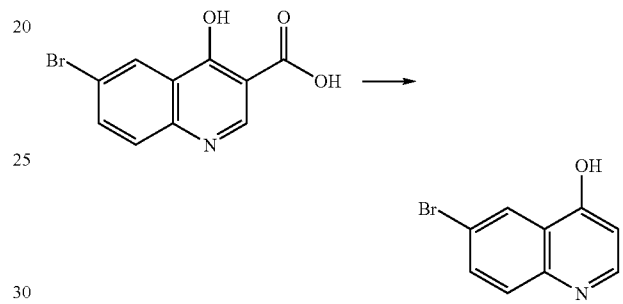

The solid 6-bromo-4-hydroxy-quinoline-3-carboxylic acid (102.59 g, 337.7 mmol) was added to hot diphenyl ether (508 g) and then the mixture was heated to reflux for 9 h to afford a light brown suspension. After cooling to room temperature, the mixture was diluted with methanol (20 mL) and diethyl ether (300 mL). Then, the solids were collected by filtration and washed with diethyl ether. After drying in air, 72.43 g (95% yield) of 6-bromo-quinolin-4-ol was isolated as a white solid: EI-HRMS m/e calcd for $C_9H_6BrNO$ (M$^+$) 222.9633, found 222.9630.

e) Preparation of 6-bromo-4-chloro-quinoline

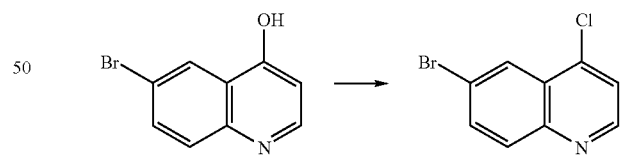

The solid 6-bromo-quinolin-4-ol (52 g, 232.1 mmol) was added to phosphorus oxychloride (213.5 mL) and then the mixture was heated to reflux for 6 h to afford a light brown solution. After cooling to room temperature, the excess phosphorus oxychloride was removed under the vacuum. The remaining residue was poured into an ice-containing beaker (2 L). Then, it was slowly neutralized with solid potassium carbonate and the resulting solids were collected by filtration and washed with water. After drying in air, 55.46 g (98.5% yield) of 6-bromo-4-chloro-quinoline was isolated as a light yellow solid: EI-HRMS m/e calcd for $C_9H_5BrClN$ (M$^+$) 240.9294, found 240.9297.

f) Preparation of 6-bromo-4-methoxy-quinoline

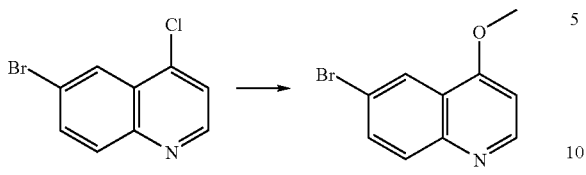

To a solution of 6-bromo-4-chloro-quinoline (12.12 g, 50 mmol) in methanol (200 mL) was added sodium methoxide (13.50 g, 250 mmol) at room temperature. Then, the reaction mixture was heated to 120° C. for 15 h in a sealed reaction flask. After cooling to room temperature, the methanol was removed under the vacuum and the residue was diluted with water. Then, the solids were collected by filtration and washed with water. After drying in air, 10.8 g (90.8% yield) of 6-bromo-4-methoxy-quinoline was isolated as a white solid which can be crystallized from acetonitrile: EI-HRMS m/e calcd for $C_{10}H_8BrNO$ ($M^+$) 236.9789, found 236.9784.

g) Preparation of 4-methoxy-quinoline-6-carbaldehyde

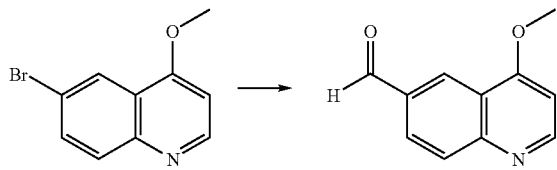

To a solution of 6-bromo-4-methoxy-quinoline (8.91 g, 37.42 mmol) in THF (tetrahydrofuran) (155 mL) was added dropwise a 2.5M solution of n-butyllithium in hexanes (16.46 mL, 4.16 mmol, 1.1 equiv.) at −70° C. During the addition, the temperature of the reaction mixture was raised slightly to −60° C. and it gave a very dark brown solution. The resulting colored solution was stirred for 30 min at this temperature. Then, a solution of dimethylformamide (5.78 mL, 74.84 mmol) in THF (10 mL) was added dropwise. After addition, the mixture was allowed to warm to room temperature and stirred for 15 h. Then, the mixture was diluted with saturated ammonium chloride solution and the two layers were separated. The aqueous layer was extracted with ethyl acetate (3×150 mL). The combined organic extracts were washed with brine solution and dried over anhydrous magnesium sulfate. Filtration of the drying agent and removal of the solvent under the vacuum gave the crude brown solid. This solid was dissolved in acetonitrile (~50 mL) at hot condition and then stored in the refrigerator overnight. The solids were collected by filtration and washed with diethyl ether. After drying in air, 4.47 g (64% yield) of 4-methoxy-quinoline-6-carbaldehyde was isolated as a white solid: EI-HRMS m/e calcd for $C_{11}H_9NO_2$ ($M^+$) 187.0633, found 187.0638.

h) Preparation of 2-[(thiophen-2-ylmethyl)-amino]-thiazol-4-one

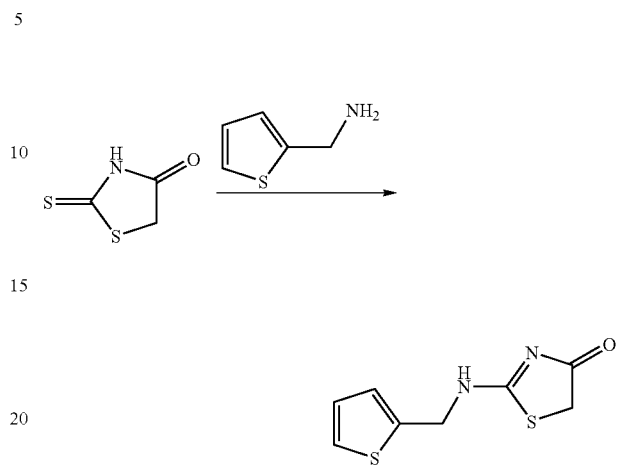

To a suspension of thiophen-2-yl-methylamine (22.63 g, 200 mmol) and rhodanine (2-thio-4-thiazolin-4-one) (13.32 g, 100 mmol) in acetonitrile (200 mL) was added DIEA (N,N-diisopropylethylamine) (34.8 mL, 45.0 mmol) at room temperature. Then, it gave a clear solution within 2 min and this solution was cooled to 0° C. To this, mercuric chloride (27.15 g, 100 mmol) was added in three portions within a period of 15 min. After addition, the suspension was allowed to warm to room temperature and stirred for 2 days. The resulting black solids were filtered through a plug of celite and washed with dichloromethane (500 mL) and methanol (1.0 L). The combined solvents were removed under the vacuum and the crude residue was diluted with water (250 mL) and ethyl acetate (250 mL). The two layers were separated and the aqueous layer was extracted with dichloromethane (2×250 mL). The two organic extracts were washed separately with brine solution and dried over anhydrous magnesium sulfate. Filtration of the drying agent and removal of the solvent under the vacuum gave the crude solid. This solid was dissolved in acetonitrile (~100 mL) at hot condition and then stored in the refrigerator overnight. The solids were collected by filtration and washed with cold acetonitrile (20 mL). After drying in air, 12.32 g (58% yield) of 2-[(thiophen-2-ylmethyl)-amino]-thiazol-4-one was isolated as a white amorphous solid: EI-HRMS m/e calcd for $C_8H_8N_2OS_2$ ($M^+$) 212.0078, found 212.0083.

i) Preparation of 5-(4-methoxy-quinolin-6-ylmeth-(Z)-ylidine)-2-[(thiophen-2-ylmethyl)-amino]-thiazol-4-one

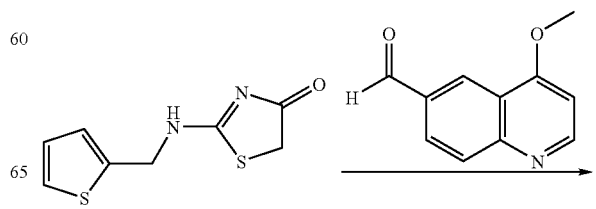

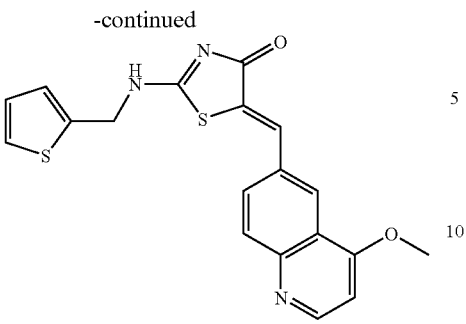

To a suspension of 2-[(thiophen-2-ylmethyl)-amino]-thiazol-4-one (95 mg, 0.45 mmol) and 4-methoxy-quinoline-6-carbaldehyde (100.6 mg, 0.48 mmol) in toluene (2 mL) in a microwave tube were added benzoic acid (11.3 mg, 0.09 mmol) and piperidine (9.3 uL, 0.09 mmol) at room temperature. The microwave tube was sealed and heated to 150° C. in a closed microwave for 1 h. Then, the mixture was cooled to room temperature and diluted with toluene. The solids were collected by filtration and washed with toluene and dichloromethane. After drying in air, 125 mg (73% yield) of 5-(4-methoxy-quinolin-6-ylmeth-(Z)-ylidine)-2-[(thiophen-2-ylmethyl)-amino]-thiazol-4-one was isolated as a brown solid: mp 258-262° C.; HRES(+) m/e calcd for $C_{19}H_{15}N_3O_2S_2$ (M+H)$^+$382.0679, found 382.0681.

Example 2

5-(4-Methoxy-quinolin-6-ylmeth-(Z)-ylidine)-2-((1R,2S)-2-phenyl-cyclopropylamino)-thiazol-4-one

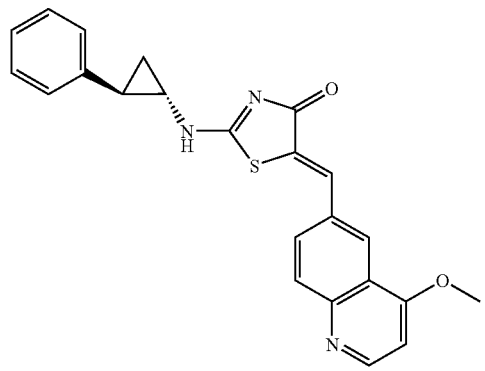

a) Preparation of 2-((1R,2S)-2-phenyl-cyclopropylamino)-thiazol-4-one

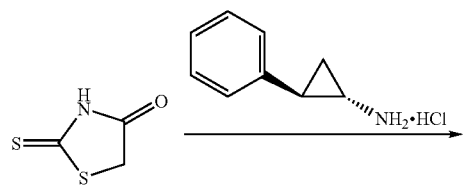

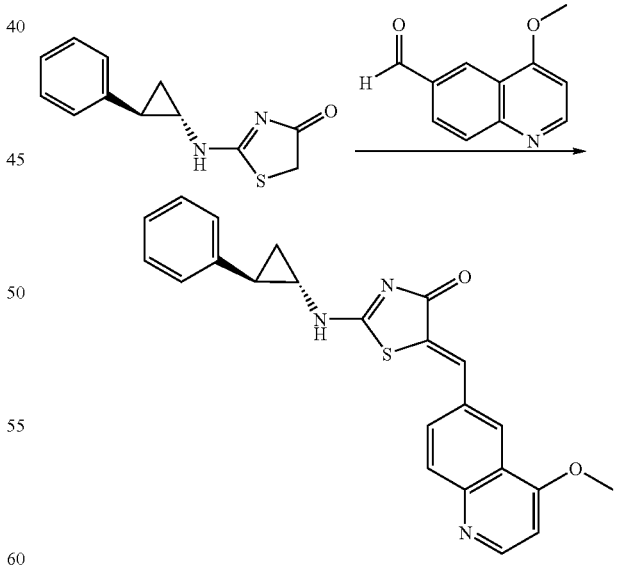

To a suspension of (1R,2S)-2-phenyl-cyclopropylamine hydrochloride (0.85 g, 5 mmol) and rhodanine (2-thio-4-thiazolin-4-one) (0.68 g, 5 mmol) in acetonitrile (20 mL) was added DIEA (N,N-diisopropylethylamine) (2.61 mL, 15 mmol) at room temperature. Then, this solution was cooled to 0° C. and mercuric chloride (1.35 g, 5 mmol) was added in two portions within a period of 10 min. After addition, the suspension was allowed to warm to room temperature and stirred for 2 days. The resulting black solids were filtered through a plug of celite and washed with ethyl acetate (500 mL). The filtrates were removed under the vacuum and the crude residue was diluted with water (100 mL) and ethyl acetate (100 mL). The two layers were separated and the aqueous layer was extracted with ethyl acetate (2×100 mL). The combined organic extracts were washed with brine solution and dried over anhydrous magnesium sulfate. Filtration of the drying agent and removal of the solvent under the vacuum gave the crude residue which was purified by using a Biotage silica gel column chromatography to obtain 0.474 g (42% yield) of 2-((1R,2S)-2-phenyl-cyclopropylamino)-thiazol-4-one as a white amorphous solid: EI-HRMS m/e calcd for $C_{12}H_{12}N_2OS$ (M$^+$) 232.0670, found 232.0665.

b) Preparation of 5-(4-methoxy-quinolin-6-ylmeth-(Z)-ylidine)-2-((1R,2S)-2-phenyl-cyclopropylamino)-thiazol-4-one To a suspension of 2-((1R,2S)-2-phenyl-cyclopropylamino)-thiazol-4-one (103.4 mg, 0.445 mmol) and 4-methoxy-quinoline-6-carbaldehyde (100 mg, 0.53 mmol) in toluene (2 mL) in a microwave tube were added benzoic acid (5.4 mg, 0.045 mmol) and piperidine (4.5 uL, 0.045 mmol) at room temperature. The microwave tube was sealed and heated to 150° C. in a closed microwave for 1 h. Then, the mixture was cooled to room temperature and diluted with toluene. The solids were collected by filtration and washed with toluene and dichloromethane. After drying in air, 120 mg (67% yield) of 5-(4-methoxy-quinolin-6-ylmeth-(Z)-ylidine)-2-((1R,2S)-2-phenyl-cyclopropylamino)-thiazol-4-one was isolated as a dark brown solid: mp 251-253° C.; HRES(+) m/e calcd for $C_{23}H_{19}N_3O_2S$ (M+H)$^+$ 402.1271, found 402.1274.

Example 3

5-(4-Ethoxy-quinolin-6-ylmeth-(Z)-ylidine)-2-(2-hydroxy-1-(R)-phenyl-ethylamino)-thiazol-4-one

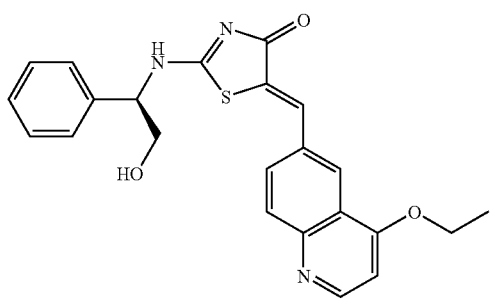

a) Preparation of 6-bromo-4-ethoxy-quinoline

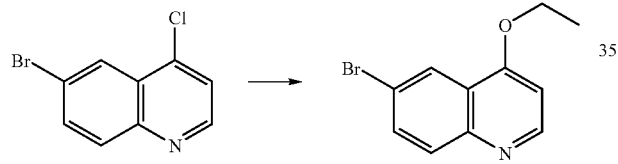

To a solution of 6-bromo-4-chloroquinoline (17 g, 70.10 mmol) in ethanol (400 mL) was added sodium ethoxide (23.85 g, 350.5 mmol) at room temperature. Then, the reaction mixture was heated to 120° C. for 15 h in a sealed reaction flask. After cooling to room temperature, the ethanol was removed under the vacuum and the residue was diluted with water. The aqueous suspension was neutralized with 3.0N hydrochloric acid until the precipitate formed and later it was diluted with saturated sodium bicarbonate solution. Then, the solids were collected by filtration and washed with water. After drying in air, 15.94 g (90.2% yield) of 6-bromo-4-ethoxy-quinoline was isolated as a white solid which can be crystallized from acetonitrile: EI-HRMS m/e calcd for $C_{11}H_{10}BrNO$ (M$^+$) 250.9946, found 250.9946.

b) Preparation of 4-ethoxy-quinoline-6-carbaldehyde

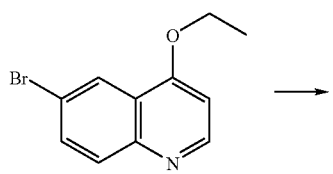

-continued

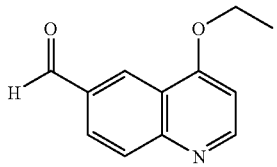

To a solution of 6-bromo-4-ethoxy-quinoline (0.53 g, 2.1 mmol) in THF (tetrahydrofuran) (21 mL) was added dropwise a 2.5M solution of n-butyllithium in hexanes (0.92 mL, 2.3 mmol, 1.1 equiv.) at −70° C. During the addition, the temperature of the reaction mixture was raised slightly to −65° C. and it gave a very dark brown solution. The resulting colored solution was stirred for 30 min at this temperature. Then, a solution of dimethylformamide (0.324 mL, 4.2 mmol) in THF (2 mL) was added dropwise. After addition, the mixture was allowed to warm to room temperature and stirred for 15 h. Then, the mixture was diluted with saturated ammonium chloride solution and the two layers were separated. The aqueous layer was extracted with ethyl acetate (3×50 mL). The combined organic extracts were washed with brine solution and dried over anhydrous magnesium sulfate. Filtration of the drying agent and removal of the solvent under the vacuum gave the crude brown solid which was purified by using a Biotage silica gel column chromatography to afford 0.370 g (88% yield) of 4-ethoxyquinoline-6-carbaldehyde as a white solid: EI-HRMS m/e calcd for $C_{12}H_{11}NO_2$ (M$^+$) 201.0790, found 201.0787 c) Preparation of 2-(2-hydroxy-1-(R)-phenyl-ethylamino)-5-(4-ethoxy-quinolin-6-ylmeth-(Z)-ylidine)-thiazol-4-one

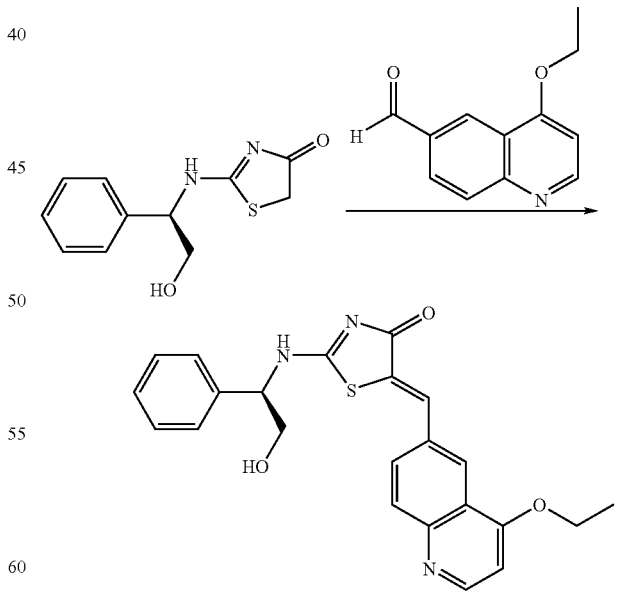

To a suspension of 2-(2-hydroxy-1-(R)-phenyl-ethylamino)-thiazol-4-one (preparation was described in example 3a) (1.15 g, 4.87 mmol) and 4-ethoxy-quinoline-6-carbaldehyde (1.077 g, 5.35 mmol) in toluene (25 mL) in a microwave tube were added benzoic acid (59.73 mg, 0.487 mmol) and piperidine (49.12 uL, 0.496 mmol) at room temperature. The microwave tube was sealed and heated to 150° C. in a closed microwave for 30 min. Then, the mixture was cooled to room temperature and diluted with toluene. The solids were collected by filtration and washed with toluene and acetonitrile. After drying in air, 650 mg (31.8% yield) of 5-(4-ethoxyquinolin-6-ylmeth-(Z)-ylidine)-2-(2-hydroxy-1-(R)-phenyl-ethylamino)-thiazol-4-one was isolated as a light gray solid: HRES(+) m/e calcd for $C_{23}H_{21}N_3O_3S$ (M+H)$^+$420.1377, found 420.1379.

Example 4

5-(4-Ethoxy-quinolin-6-ylmeth-(Z)-ylidine)-2-[(thiophen-2-ylmethyl)-amino]-thiazol-4-one

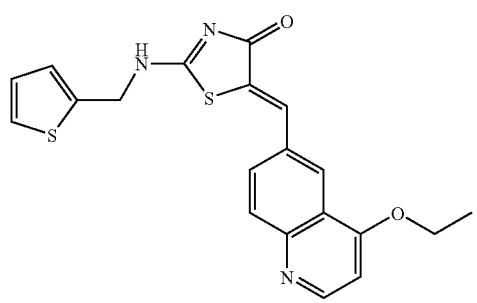

a) Preparation of 5-(4-ethoxy-quinolin-6-ylmeth-(Z)-ylidine)-2-[(thiophen-2-ylmethyl)-amino]-thiazol-4-one

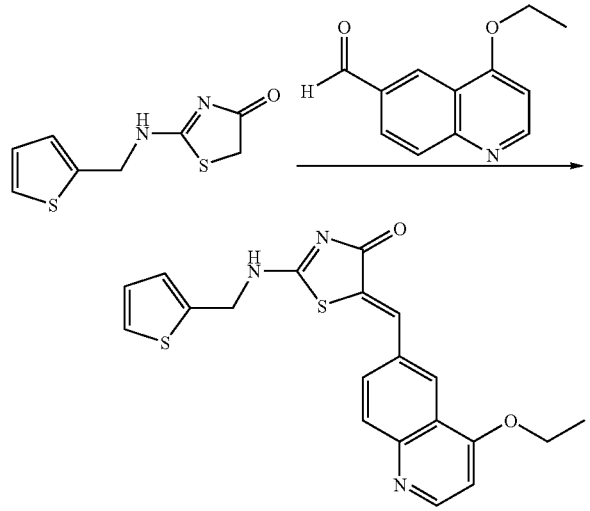

To a suspension of 2-[(thiophen-2-ylmethyl)-amino]-thiazol-4-one (preparation was described in example 1 h) (48 mg, 0.23 mmol) and 4-ethoxy-quinoline-6-carbaldehyde (54.57 mg, 0.27 mmol) in toluene (1 mL) in a microwave tube were added benzoic acid (2.78 mg, 0.023 mmol) and piperidine (2.3 uL, 0.023 mmol) at room temperature. The microwave tube was sealed and heated to 150° C. in a closed microwave for 1 h. Then, the mixture was cooled to room temperature and diluted with toluene. The solids were collected by filtration and washed with toluene and diethyl ether. After drying in air, 60 mg (67% yield) of 5-(4-ethoxy-quinolin-6-ylmeth-(Z)-ylidine)-2-[(thiophen-2-ylmethyl)-amino]-thiazol-4-one was isolated as a brown solid: mp 226-228° C.; HRES(+) m/e calcd for $C_{20}H_{17}N_3O_2S_2$ (M+H)$^+$396.0835, found 396.0835.

Example 5

5-(4-Ethoxy-quinolin-6-ylmeth-(Z)-ylidine)-2-((1R,2S)-2-phenyl-cyclopropylamino)-thiazol-4-one

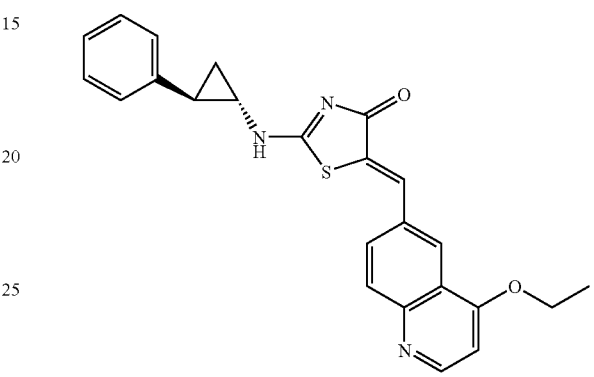

a) Preparation of 5-(4-ethoxy-quinolin-6-ylmeth-(Z)-ylidine)-2-((1R,2S)-2-phenyl-cyclopropylamino)-thiazol-4-one

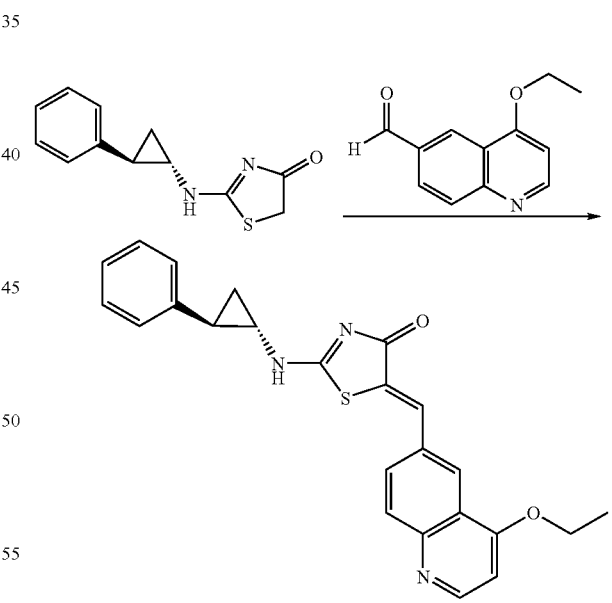

To a suspension of 2-((1R,2S)-2-phenyl-cyclopropylamino)-thiazol-4-one (preparation was described in example 2a) (50 mg, 0.215 mmol) and 4-ethoxy-quinoline-6-carbaldehyde (51.92 mg, 0.258 mmol) in toluene (1 mL) in a microwave tube was added benzoic acid (2.64 mg, 0.022 mmol) and piperidine (2.2 uL, 0.022 mmol) at room temperature. The microwave tube was sealed and heated to 150° C. in a closed microwave for 1 h. Then, the mixture was cooled to room temperature and diluted with toluene. The solids were collected by filtration and washed with toluene and dichloromethane. After drying in air, 65 mg (73% yield) of 5-(4-ethoxy-quinolin-6-ylmeth-(Z)-ylidine)-2-((1R,2S)-2-phenyl-cyclopropylamino)-thiazol-4-one was isolated as a dark brown solid: mp 266-268° C.; HRES(+) m/e calcd for $C_{24}H_{21}N_3O_2S$ (M+H)$^+$416.1427, found 416.1429.

Example 6

5-(4-Chloro-quinolin-6-ylmeth-(Z)-ylidine)-2-[(thiophen-2-ylmethyl)-amino]-thiazol-4-one

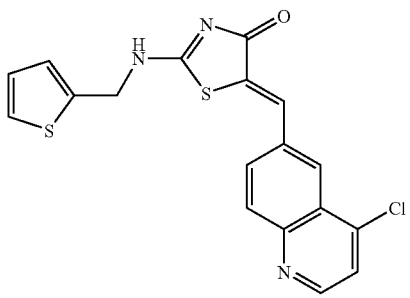

a) Preparation of 4-chloro-quinoline-6-carbaldehyde

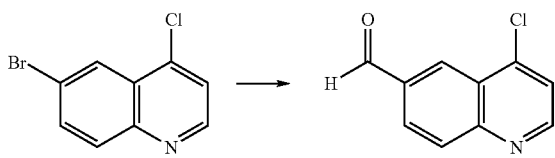

To a solution of 6-bromo-4-chloro-quinoline (3.0 g, 12.37 mmol) in THF (60 mL) was added dropwise a 2.5M solution of n-butyllithium in hexanes (5.95 mL, 14.84 mmol, 1.1 equiv.) at −70° C. During the addition, the color of the solution was turned to red and it was stirred for 1 h at this temperature. Then, a solution of dimethylformamide (1.91 mL, 24.74 mmol) in THF (10 mL) was added dropwise. After addition, the mixture was allowed to warm to room temperature and stirred for 2 h. Then, the mixture was diluted with saturated ammonium chloride solution and the two layers were separated. The aqueous layer was extracted with ethyl acetate (3×100 mL). The combined organic extracts were washed with brine solution and dried over anhydrous magnesium sulfate. Filtration of the drying agent and removal of the solvent under the vacuum gave the crude brown solid which was purified by using a Biotage silica gel column chromatography to obtain 0.6 g (25% yield) of 4-chloro-quinoline-6-carbaldehyde as a white solid: EI-HRMS m/e calcd for $C_{10}H_6ClNO$ (M$^+$) 187.0633, found 187.0638.

b) Preparation of 5-(4-chloro-quinolin-6-ylmeth-(Z)-ylidine)-2-[(thiophen-2-ylmethyl)-amino]-thiazol-4-one

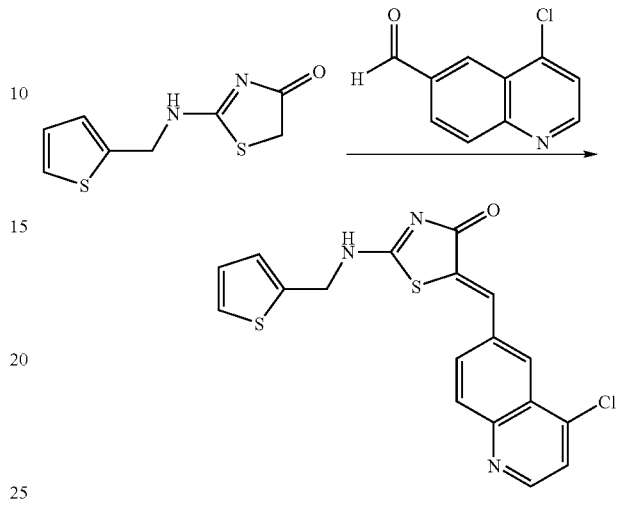

To a suspension of 2-[(thiophen-2-ylmethyl)-amino]-thiazol-4-one (preparation described in example 1 h) (92 mg, 0.43 mmol) and 4-chloro-quinoline-6-carbaldehyde (99.57 mg, 0.52 mmol) in toluene (2 mL) in a microwave tube were added benzoic acid (5.3 mg, 0.043 mmol) and piperidine (4.37 uL, 0.044 mmol) at room temperature. The microwave tube was sealed and heated to 150° C. in a closed microwave for 1 h. Then, the mixture was cooled to room temperature and diluted with toluene. The solids were collected by filtration and washed with toluene and diethyl ether. After drying in air, 6 mg (3.6% yield) of 5-(4-chloro-quinolin-6-ylmeth-(Z)-ylidine)-2-[(thiophen-2-ylmethyl)-amino]-thiazol-4-one was isolated as an yellow solid: HRES(+) m/e calcd for $C_{18}H_{12}ClN_3OS_2$ (M+H)$^+$386.0183, found 386.088.

Example 7

5-(4-Chloro-quinolin-6-ylmeth-(Z)-ylidine)-2-((1R,2S)-2-phenyl-cyclopropylamino)-thiazol-4-one

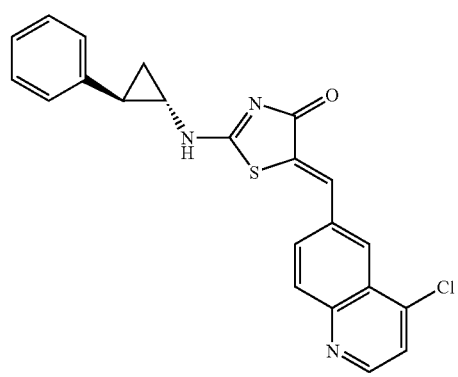

a) Preparation of 5-(4-chloro-quinolin-6-ylmeth-(Z)-ylidine)-2-((1R,2S)-2-phenyl-cyclopropylamino)-thiazol-4-one

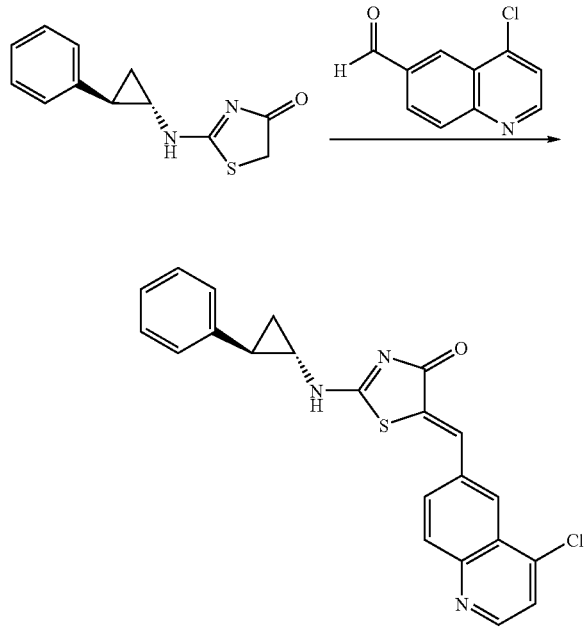

To a suspension of 2-((1R,2S)-2-phenyl-cyclopropylamino)-thiazol-4-one (preparation described in example 2a) (101 mg, 0.435 mmol) and 4-chloro-quinoline-6-carbaldehyde (100 mg, 0.52 mmol) in toluene (2 mL) in a microwave tube were added benzoic acid (5.4 mg, 0.044 mmol) and piperidine (4.4 uL, 0.044 mmol) at room temperature. The microwave tube was sealed and heated to 150° C. in a closed microwave for 1 h. Then, the mixture was cooled to room temperature and diluted with toluene. The solids were collected by filtration and washed with toluene and diethyl ether. After drying in air, 9 mg (5% yield) of 5-(4-chloro-quinolin-6-ylmeth-(Z)-ylidine)-2-((1R,2S)-2-phenyl-cyclopropylamino)-thiazol-4-one was isolated as a dark brown solid: HRES(+) m/e calcd for $C_{22}H_{16}ClN_3OS$ (M+H)$^+$ 406.0776, found 406.0779.

Example 8

2-(2-Hydroxy-1-(R)-phenyl-ethylamino)-5-(4-methoxy-quinolin-6-ylmeth-(Z)-ylidine)-thiazol-4-one

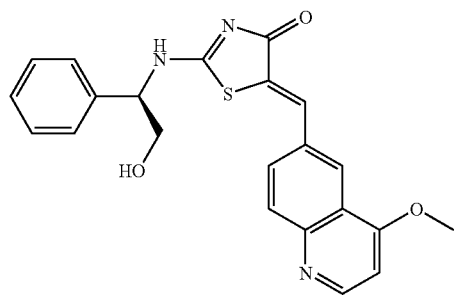

a) Preparation of 2-(2-hydroxy-1-(R)-phenyl-ethylamino)-thiazol-4-one

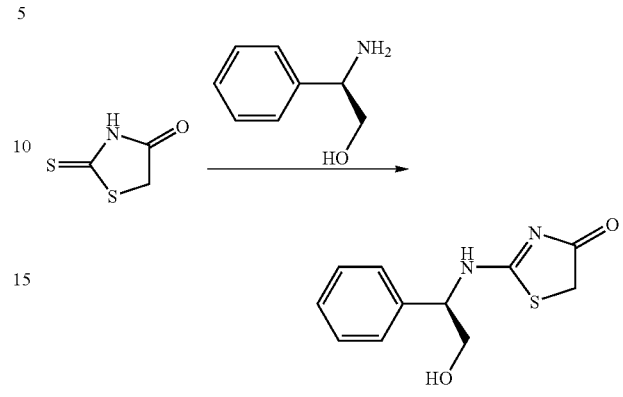

To a suspension of (R)-(−)-2-phenylglycinol (15.34 g, 111.82 mmol) and rhodanine (14.65 g, 110 mmol) in acetonitrile (200 mL) was added DIPEA (20.03 mL, 115 mmol) at room temperature. Then, it gave a clear solution within 2 min and this solution was cooled to 0° C. To this, mercuric chloride (31.22 g, 115 mmol) was added in three portions within a period of 15 min. After addition, the suspension was allowed to warm to room temperature and stirred for 2 days. The resulting black solids were filtered through a plug of celite and washed with dichloromethane (500 mL) and methanol (1.0 L). The combined solvents were removed under the vacuum and the crude residue was diluted with water (250 mL) and ethyl acetate (250 mL). The two layers were separated and the aqueous layer was extracted with dichloromethane (2×250 mL). The two organic extracts were washed separately with brine solution and dried over anhydrous magnesium sulfate. Filtration of the drying agent and removal of the solvent under the vacuum gave the crude yellow solid. This solid was dissolved in acetonitrile (~100 mL) at hot condition and then stored in the refrigerator overnight. The solids were collected by filtration and washed with cold acetonitrile. After drying in air, 12.99 g (50% yield) of 2-(2-hydroxy-1-(R)-phenyl-ethylamino)-thiazol-4-one was isolated as a white amorphous solid: EI-HRMS m/e calcd for $C_{11}H_{12}N_2O_2S$ (M-H$_2$O) 218.0514, found 218.0511.

b) Preparation of 2-(2-hydroxy-1-(R)-phenyl-ethylamino)-5-(4-methoxy-quinolin-6-ylmeth-(Z)-ylidine)-thiazol-4-one

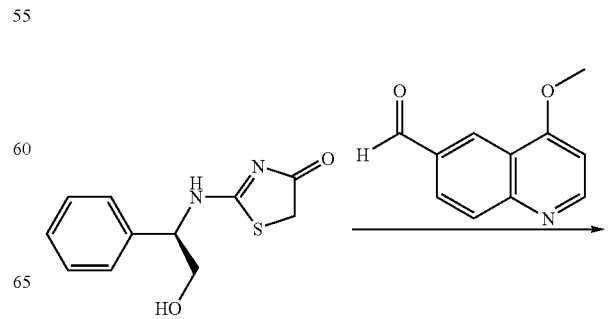

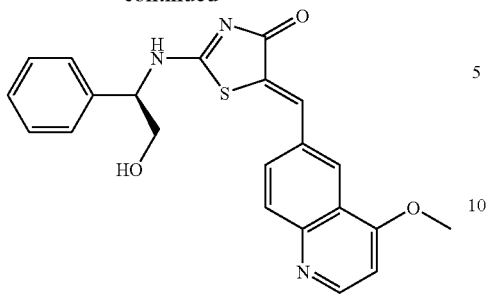

To a suspension of 2-(2-hydroxy-1-(R)-phenyl-ethylamino)-thiazol-4-one (105.2 mg, 0.44 mmol) and 4-methoxy-quinoline-6-carbaldehyde (100 mg, 0.53 mmol) in toluene (2 mL) in a microwave tube were added benzoic acid (5.5 mg, 0.045 mmol) and piperidine (4.5 uL, 0.045 mmol) at room temperature. The microwave tube was sealed and heated to 150° C. in a closed microwave for 1 h. Then, the mixture was cooled to room temperature and diluted with toluene. The solids were collected by filtration and washed with toluene. Then, it was crystallized from acetonitrile at hot condition. After cooling in the refrigerator overnight, the solids were collected by filtration and washed with cold acetonitrile. After drying in air, 32 mg (17.7% yield) of 2-(2-hydroxy-1-(R)-phenyl-ethylamino)-5-(4-methoxy-quinolin-6-ylmeth-(Z)-ylidine)-thiazol-4-one was isolated as a brown solid: HRES(+) m/e calcd for $C_{22}H_{19}N_3O_3S$ (M+H)$^+$ 406.1220, found 406.1219.

Example 9

5-(4-Cyclohexylmethoxy-quinolin-6-ylmeth-(Z)-ylidine)-2-[(thiophen-2-ylmethyl)-amino]-thiazol-4-one

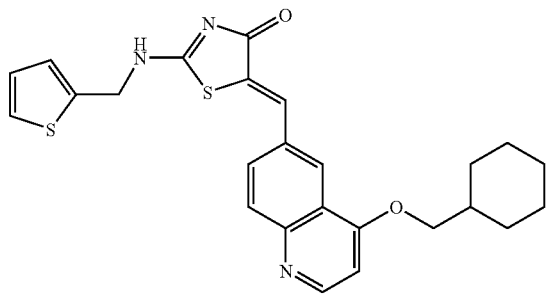

a) Preparation of 6-bromo-4-cyclohexylmethoxy-quinoline

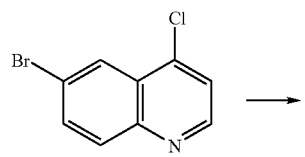

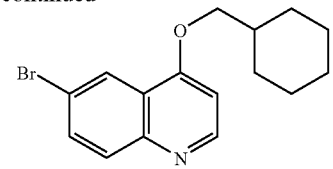

To a solution of 6-bromo-4-chloro-quinoline (0.550 g, 2.27 mmol) in cyclohexylmethanol (5 mL) was added a solution of sodium cyclohexylmethoxide (11.34 mmol, prepared from cyclohexylmethanol and sodium) at room temperature. Then, the reaction mixture was heated to 120° C. for 15 h in a sealed reaction flask. After cooling to room temperature, the reaction mixture was diluted with water and the solvent was removed under the vacuum. Then, the remaining aqueous solution was neutralized with 3.0N hydrochloric acid and the organic compound was extracted into ethyl acetate (3×50 mL). The combined extracts were washed with brine solution and dried over anhydrous magnesium sulfate. After filtration of the drying agent, the filtrate was removed under the vacuum and the residue was purified by using a Biotage silica gel column chromatography to afford 0.518 g (71% yield) of 6-bromo-4-cyclohexylmethoxy-quinoline as a light yellow oil: EI-HRMS m/e calcd for $C_{16}H_{18}BrNO$ (M$^+$) 320.2304, found 320.2314.

b) Preparation of 4-cyclohexylmethoxy-quinoline-6-carbaldehyde

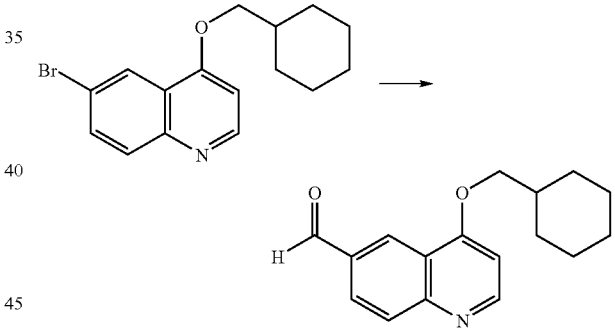

To a solution of 6-bromo-4-cyclohexylmethoxy-quinoline (0.510 g, 1.59 mmol) in THF (10 mL) was added dropwise a 2.5M solution of n-butyllithium in hexanes (0.765 mL, 1.92 mmol, 1.2 equiv.) at −70° C. During the addition, the color of the solution was turned into red and this solution was stirred for 1 h at this temperature. Then, a solution of dimethylformamide (0.246 mL, 3.19 mmol) in THF (1 mL) was added dropwise. After addition, the mixture was allowed to warm to room temperature and stirred for 2 h. Then, the mixture was diluted with saturated ammonium chloride solution and the two layers were separated. The aqueous layer was extracted with ethyl acetate (3×150 mL). The combined organic extracts were washed with brine solution and dried over anhydrous magnesium sulfate. Filtration of the drying agent and removal of the solvent under the vacuum gave the crude residue which was purified by using a Biotage silica gel column chromatography to afford 0.205 g (48% yield) of 4-cyclohexylmethoxy-quinoline-6-carbaldehyde as a white solid: EI-HRMS m/e calcd for $C_{17}H_{19}NO_2$ (M$^+$) 269.3513, found 269.3511.

c) Preparation of 5-(4-cyclohexylmethoxy-quinolin-6-ylmeth-(Z)-ylidine)-2-[(thiophen-2-ylmethyl)-amino]-thiazol-4-one

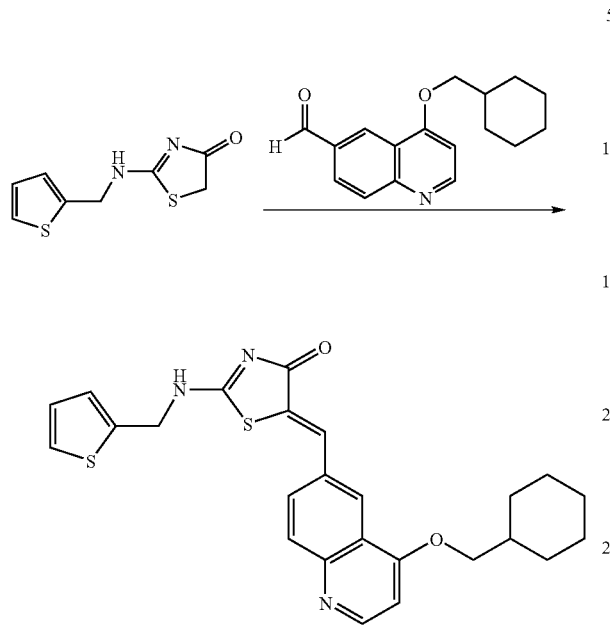

To a suspension of 2-[(thiophen-2-ylmethyl)-amino]-thiazol-4-one (preparation described in example 1 h) (35 mg, 0.165 mmol) and 4-cyclohexylmethoxy-quinoline-6-carbaldehyde (51.1 mg, 0.19 mmol) in toluene (1 mL) in a microwave tube were added benzoic acid (2.02 mg, 0.016 mmol) and piperidine (1.66 uL, 0.016 mmol) at room temperature. The microwave tube was sealed and heated to 150° C. in a closed microwave for 1 h. Then, the mixture was cooled to room temperature and diluted with toluene. The solids were collected by filtration and washed with toluene and diethyl ether. After drying in air, 21 mg (27.5% yield) of 5-(4-cyclohexylmethoxy-quinolin-6-ylmeth-(Z)-ylidine)-2-[(thiophen-2-ylmethyl)-amino]-thiazol-4-one was isolated as a brown solid: HRES(+) m/e calcd for $C_{25}H_{25}N_3O_2S_2$ (M+H)$^+$464.1461, found 464.1466.

Example 10

5-(4-Cyclohexylmethoxy-quinolin-6-ylmeth-(Z)-ylidine)-2-((1R,2S)-2-phenyl-cyclopropylamino)-thiazol-4-one

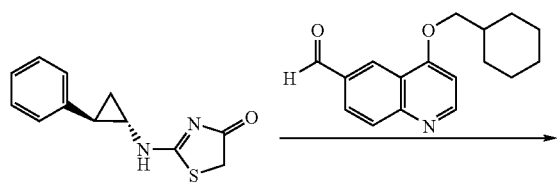

a) Preparation of 5-(4-cyclohexylmethoxy-quinolin-6-ylmeth-(Z)-ylidine)-2-((1R,2S)-2-phenyl-cyclopropylamino)-thiazol-4-one

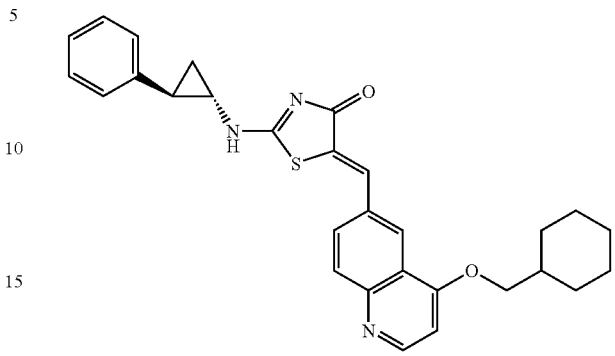

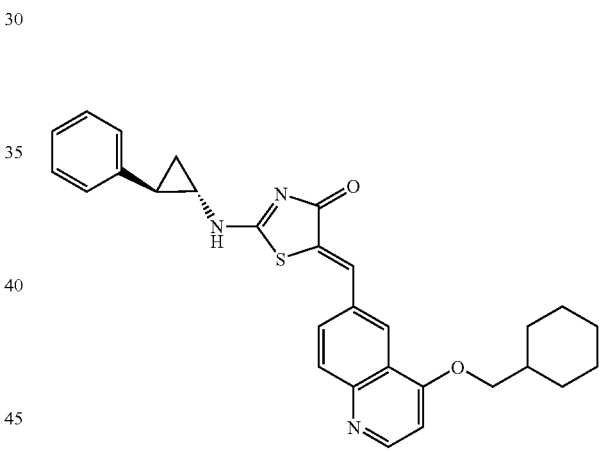

To a suspension of 2-((1R,2S)-2-phenyl-cyclopropylamino)-thiazol-4-one (preparation described in example 2a) (38 mg, 0.164 mmol) and 4-cyclohexylmethoxy-quinoline-6-carbaldehyde (53 mg, 0.197 mmol) in toluene (0.8 mL) in a microwave tube were added benzoic acid (2.01 mg, 0.016 mmol) and piperidine (1.65 uL, 0.016 mmol) at room temperature. The microwave tube was sealed and heated to 150° C. in a closed microwave for 1 h. Then, the mixture was cooled to room temperature and diluted with toluene. The solids were collected by filtration and washed with toluene and dichloromethane. After drying in air, 50 mg (63% yield) of 5-(4-cyclohexylmethoxy-quinolin-6-ylmeth-(Z)-ylidine)-2-((1R,2S)-2-phenyl-cyclopropylamino)-thiazol-4-one was isolated as a dark brown solid: mp 223-227° C.; HRES(+) m/e calcd for $C_{29}H_{29}N_3O_2S$ (M+H)$^+$484.2053, found 484.2059.

Example 11

5-(4-Cyclohexylmethoxy-quinolin-6-ylmeth-(Z)-ylidine)-2-(2-hydroxy-1-(R)-phenyl-ethylamino)-thiazol-4-one

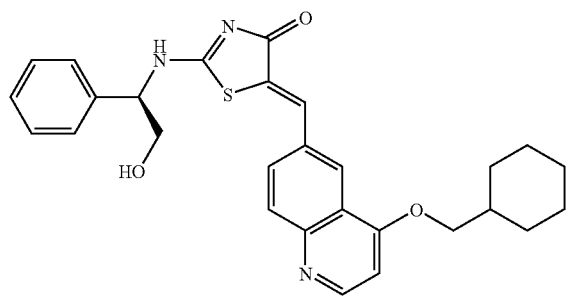

a) Preparation of 5-(4-cyclohexylmethoxy-quinolin-6-ylmeth-(Z)-ylidine)-2-(2-hydroxy-1-(R)-phenyl-ethylamino)-thiazol-4-one

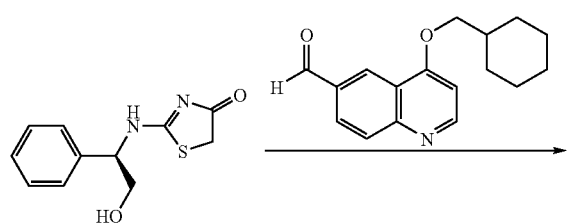

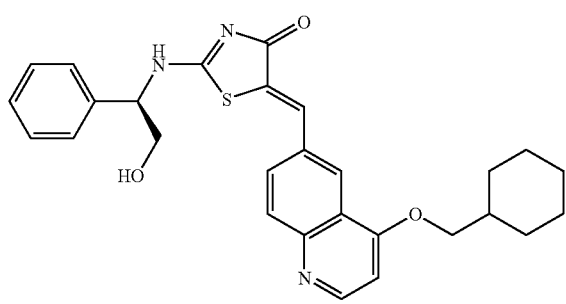

To a suspension of 2-(2-hydroxy-1-(R)-phenyl-ethylamino)-thiazol-4-one (preparation described in example 3a) (65 mg, 0.275 mmol) and 4-cyclohexylmethoxy-quinoline-6-carbaldehyde (92.59 mg, 0.34 mmol) in toluene (1 mL) in a microwave tube were added benzoic acid (3.37 mg, 0.027 mmol) and piperidine (2.77 uL, 0.028 mmol) at room temperature. The microwave tube was sealed and heated to 150° C. in a closed microwave for 1 h. Then, the mixture was cooled to room temperature and diluted with toluene. The solids were collected by filtration and washed with toluene and diethyl ether. Then, these solids were suspended in dichloromethane and heated the suspension with heat gun to remove any impurities. After cooling to room temperature, the solids were collected by filtration and washed with dichloromethane. After drying in air, 52 mg (38.8% yield) of 5-(4-cyclohexylmethoxy-quinolin-6-ylmeth-(Z)-ylidine)-2-(2-hydroxy-1-(R)-phenyl-ethylamino)-thiazol-4-one was isolated as a brown solid: HRES(+) m/e calcd for $C_{28}H_{29}N_3O_3S$ (M+H)$^+$488.2003, found 488.2002.

Example 12

5-(4-Diethylamino-quinolin-6-ylmeth-(Z)-ylidine)-2-((1R,2S)-2-phenyl-cyclopropylamino)-thiazol-4-one

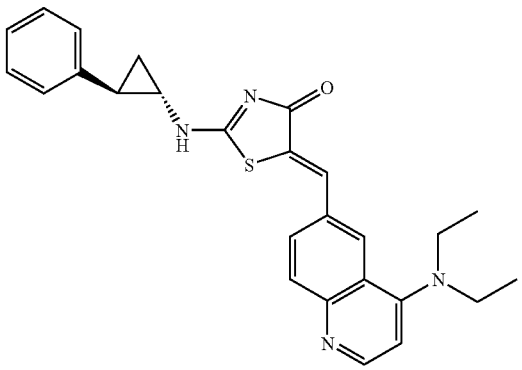

a) Preparation of (6-bromo-quinolin-4-yl)-diethylamine

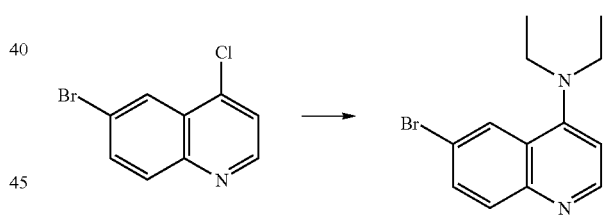

To a mixture of 6-bromo-4-chloro-quinoline (0.900 g, 3.71 mmol) and diethylamine (1.364 g, 18.56 mmol) in ethanol (10 mL) was added potassium carbonate (2.56 g, 18.56 mmol) at room temperature. Then, the reaction mixture was stirred for 15 h in a sealed tube. TLC analysis of the reaction mixture indicated the presence of lot of 6-bromo-4-chloro-quinoline and another 2 mL of diethylamine was added and heated to 100° C. and stirred for 15 h. After cooling to room temperature, the reaction mixture was diluted with water and the solvent was removed under the vacuum. Then, the product was extracted with ethyl acetate (3×50 mL). The combined extracts were washed with brine solution and dried over anhydrous magnesium sulfate. After filtration of the drying agent, the filtrate was removed under the vacuum and the residue was purified by using a Biotage silica gel column chromatography to afford 0.180 g (17.4% yield) of (6-bromo-quinolin-4-yl)-diethylamine as a light yellow oil: EI-LRMS m/e calcd for $C_{13}H_{15}BrN_2$ (M$^+$) 279.1, found 279.1.

b) Preparation of 4-(diethylamino)-quinoline-6-carbaldehyde

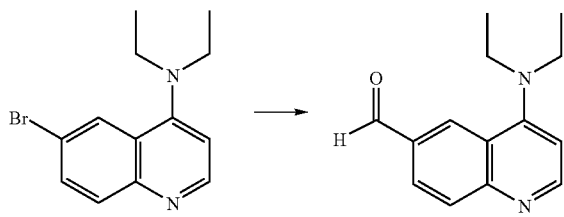

To a solution of (6-bromo-quinolin-4-yl)-diethylamine (0.510 g, 1.59 mmol) in THF (10 mL) was added dropwise a 2.5M solution of n-butyllithium in hexanes (0.765 mL, 1.92 mmol, 1.2 equiv.) at −70° C. During the addition, the color of the solution was turned into red and this solution was stirred for 1 h at this temperature. Then, a solution of dimethylformamide (0.246 mL, 3.19 mmol) in THF (1 mL) was added dropwise. After addition, the mixture was allowed to warm to room temperature and stirred for 2 h. Then, the mixture was diluted with saturated ammonium chloride solution and the two layers were separated. The aqueous layer was extracted with ethyl acetate (3×150 mL). The combined organic extracts were washed with brine solution and dried over anhydrous magnesium sulfate. Filtration of the drying agent and removal of the solvent under the vacuum gave the crude residue which was purified by using a Biotage silica gel column chromatography to afford 0.205 g (48% yield) of 4-(diethylamino)-quinoline-6-carbaldehyde as a white solid: EI-LRMS m/e calcd for $C_{14}H_{16}N_2O$ (M+) 229.1, found 229.1.

c) Preparation of 5-(4-diethylamino-quinolin-6-yl-meth-(Z)-ylidine)-2-((1R,2S)-2-phenyl-cyclopropylamino)-thiazol-4-one

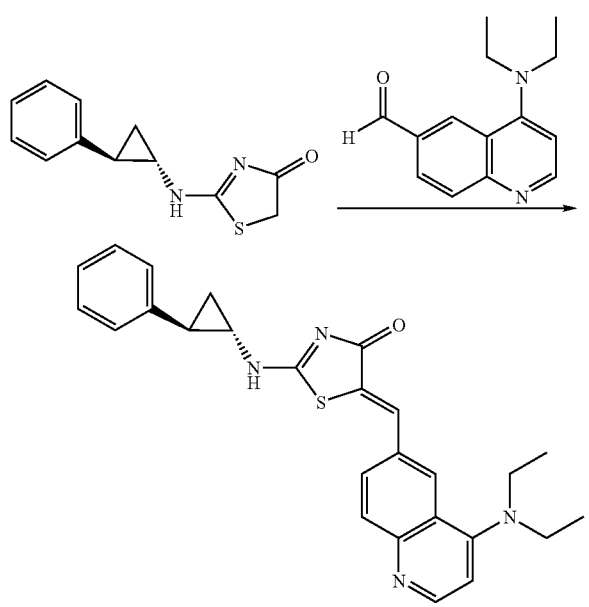

To a suspension of 2((1R,2S)-2-phenyl-cyclopropylamino)-thiazol-4-one (preparation described in example 2a) (50 mg, 0.216 mmol) and 4-(diethylamino)-quinoline-6-carbaldehyde (59.2 mg, 0.259 mmol) in toluene (1 mL) in a microwave tube were added benzoic acid (2.64 mg, 0.021 mmol) and piperidine (2.17 uL, 0.022 mmol) at room temperature. The microwave tube was sealed and heated to 150° C. in a closed microwave for 1 h. Then, the mixture was cooled to room temperature and diluted with toluene. The solids were collected by filtration and washed with toluene and dichloromethane. After dying in air, 62 mg (65% yield) of 5-[4-(diethylamino)-quinolin-6-ylmeth-(Z)-ylidine]-2-((1R,2S)-2-phenyl-cyclopropylamino)-thiazol-4-one was isolated as a brown solid: HRES (+) m/e calcd for $C_{26}H_{26}N_4OS$ (M+H)+443.1900, found 443.1899.

Example 13

5-(4-Morpholin-4-yl-quinolin-6-ylmeth-(Z)-ylidine)-2-((1R,2S)-2-phenyl-cyclopropylamino)-thiazol-4-one

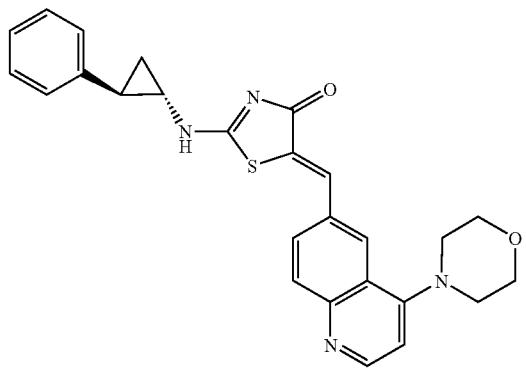

a) Preparation of 6-bromo-4-morpholin-4-yl-quinoline

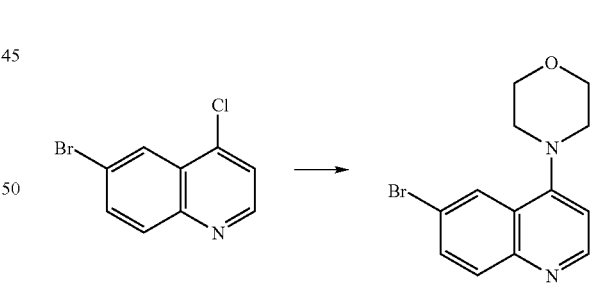

A mixture of 6-bromo-4-chloro-quinoline (1.0 g, 4.12 mmol) and morpholine (9.98 g, 114.6 mmol) was heated to 150° C. in a sealed tube and stirred for 2 days. Then, the brown suspension was diluted with water and extracted with ethyl acetate (3×50 mL). The combined extracts were washed with brine solution and dried over anhydrous magnesium sulfate. After filtration of the drying agent, the filtrate was removed under the vacuum and the residue was purified by using a Biotage silica gel column chromatography to afford 1.06 g (87.7% yield) of 6-bromo-4-morpholin-4-yl-quinoline as a light brown solid: EI-LRMS m/e calcd for $C_{13}H_{13}BrN_2O$ (M+) 293.1, found 293.1.

b) Preparation of 4-morpholin-4-yl-quinoline-6-carbaldehyde

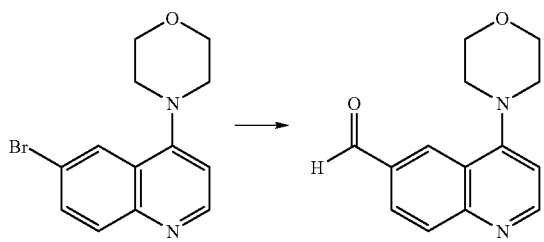

To a solution of 6-bromo-4-morpholin-4-ylquinoline (1.06 g, 3.62 mmol) in THF (22 mL) was added dropwise a 2.5M solution of n-butyllithium in hexanes (1.74 mL, 4.34 mmol, 1.2 equiv.) at −70° C. During the addition, the color of the solution was turned into red and this solution was stirred for 1 h at this temperature. Then, a solution of dimethylformamide (0.558 mL, 7.23 mmol) in THF (2 mL) was added dropwise. After addition, the mixture was allowed to warm to room temperature and stirred for 2 h. Then, the mixture was diluted with saturated ammonium chloride solution and the two layers were separated. The aqueous layer was extracted with ethyl acetate (3×50 mL). The combined organic extracts were washed with brine solution and dried over anhydrous magnesium sulfate. Filtration of the drying agent and removal of the solvent under the vacuum gave the crude residue which was purified by using a Biotage silica gel column chromatography to afford 0.390 g (44.5% yield) of 4-morpholin-4-yl-quinoline-6-carbaldehyde as a white solid: EI-LRMS m/e calcd for $C_{14}H_{14}N_2O_2$ (M$^+$) 243.1, found 243.1.

c) Preparation of 5-(4-morpholin-4-yl-quinolin-6-ylmeth-(Z)-ylidine)-2-((1R,2S)-2-phenyl-cyclopropylamino)-thiazol-4-one

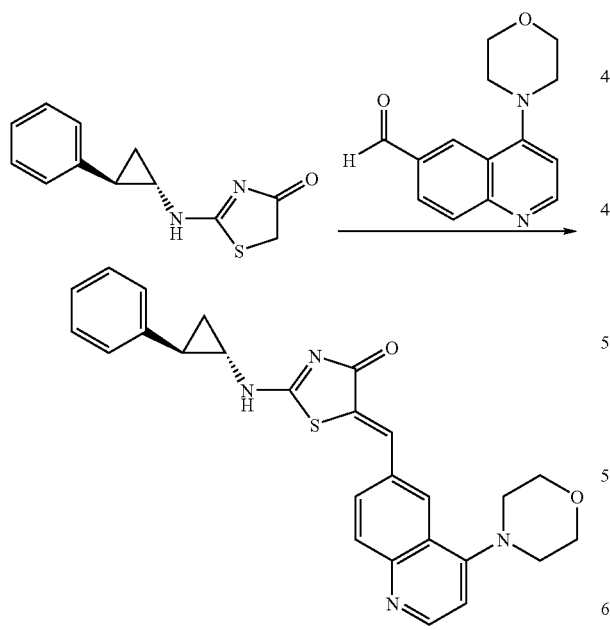

To a suspension of 2-((1R,2S)-2-phenyl-cyclopropylamino)-thiazol-4-one (preparation described in example 2a) (50 mg, 0.216 mmol) and 4-morpholin-4-yl-quinoline-6-carbaldehyde (59.2 mg, 0.259 mmol) in toluene (1 mL) in a microwave tube were added benzoic acid (2.64 mg, 0.021 mmol) and piperidine (2.17 uL, 0.022 mmol) at room temperature. The microwave tube was sealed and heated to 150° C. in a closed microwave for 1 h. Then, the mixture was cooled to room temperature and diluted with toluene. The solids were collected by filtration and washed with toluene and dichloromethane. After drying in air, 68 mg (69% yield) of 5-(4-morpholin-4-yl-quinolin-6-ylmeth-(Z)-ylidine)-2-((1R,2S)-2-phenyl-cyclopropylamino)-thiazol-4-one was isolated as a brown solid: HRES(+) m/e calcd for $C_{26}H_{24}N_4O_2S$ (M+H)$^+$ 457.1693, found 457.1694.

Example 14

5-(4-Morpholin-4-yl-quinolin-6-ylmeth-(Z)-ylidine)-2-(2-hydroxy-1-(R)-phenyl-ethylamino)-thiazol-4-one

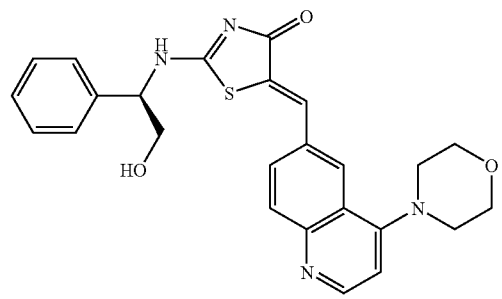

a) Preparation of 5-(4-morpholin-4-yl-quinolin-6-ylmeth-(Z)-ylidine)-2-(2-hydroxy-1-(R)-phenyl-ethylamino)-thiazol-4-one

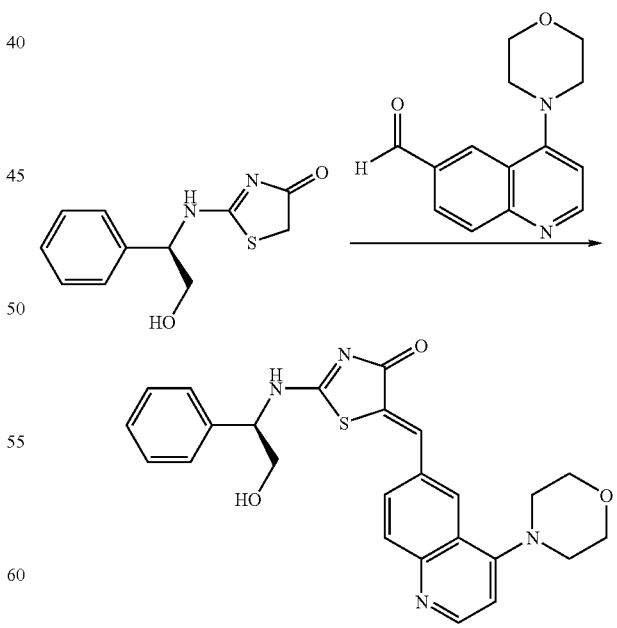

To a suspension of 2-(2-hydroxy-1-(R)-phenyl-ethylamino)-thiazol-4-one (preparation described in example 3a) (50 mg, 0.212 mmol) and 4-morpholin-4-yl-quinoline-6-carbaldehyde (61.64 mg, 0.254 mmol) in toluene (0.950 mL)

in a microwave tube were added benzoic acid (2.6 mg, 0.021 mmol) and piperidine (2.14 uL, 0.021 mmol) at room temperature. The microwave tube was sealed and heated to 150° C. in a closed microwave for 1 h. Then, the mixture was cooled to room temperature and diluted with toluene. The solids were collected by filtration and washed with toluene and diethyl ether. Then, these solids were dissolved in dichloromethane at hot condition and later removed the solvent under the vacuum. The residue was purified by preparative HPLC to afford 25 mg (25.7% yield) of 5-(4-morpholin-4-yl-quinolin-6-ylmeth-(Z)-ylidine)-2-(2-hydroxy-1-(R)-phenyl-ethylamino)-thiazol-4-one was isolated as a brown amorphous solid: LRES(+) m/e calcd for $C_{25}H_{24}N_4O_3S$ (M+H)$^+$461.2, found 461.2.

Example 15

5-(4-Morpholin-4-yl-quinolin-6-ylmeth-(Z)-ylidine)-2-[(thiophen-2-ylmethyl)-amino]-thiazol-4-one

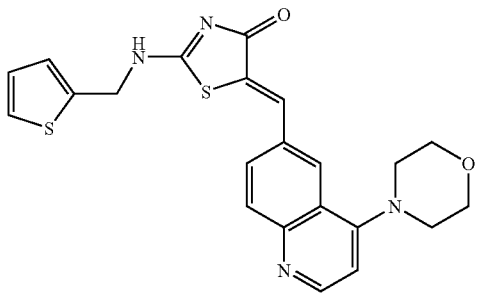

a) Preparation of 5-(4-morpholin-4-yl-quinolin-6-ylmeth-(Z)-ylidine)-2-[(thiophen-2-ylmethyl)-amino]-thiazol-4-one

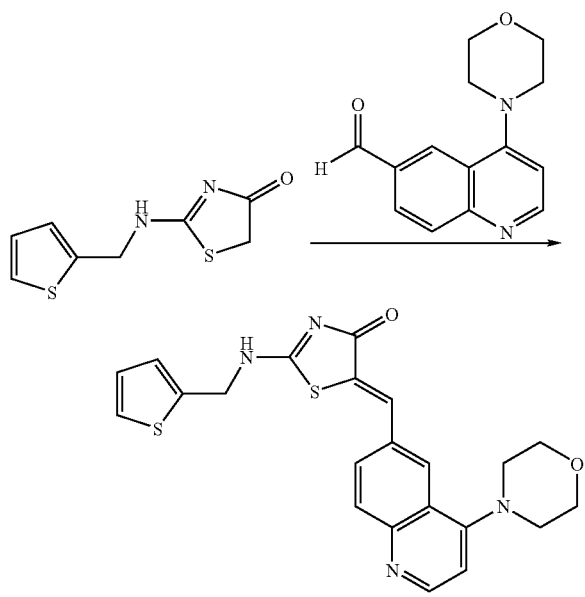

To a suspension of 2-[(thiophen-2-ylmethyl)-amino]-thiazol-4-one (preparation described in example 1 h) (50 mg, 0.236 mmol) and 4-morpholin-4-yl-quinoline-6-carbaldehyde (68.6 mg, 0.283 mmol) in toluene (0.950 mL) in a microwave tube were added benzoic acid (2.89 mg, 0.023 mmol) and piperidine (2.38 uL, 0.024 mmol) at room temperature. The microwave tube was sealed and heated to 150° C. in a closed microwave for 1 h. Then, the mixture was cooled to room temperature and diluted with toluene. The solids were collected by filtration and washed with toluene and dichloromethane. After drying in air, 46 mg (44.7% yield) of 5-(4-morpholin-4-yl-quinolin-6-ylmeth-(Z)-ylidine)-2-[(thiophen-2-ylmethyl)-amino]-thiazol-4-one was isolated as a brown solid: HRES(+) m/e calcd for $C_{22}H_{20}N_4O_2S_2$ (M+H)$^+$437.1101, found 437.1104.

Example 16

5-[4-(2-Methoxy-ethoxy)-quinolin-6-ylmeth-(Z)-ylidine]-2-((1R,2S)-2-phenyl-cyclopropylamino)-thiazol-4-one

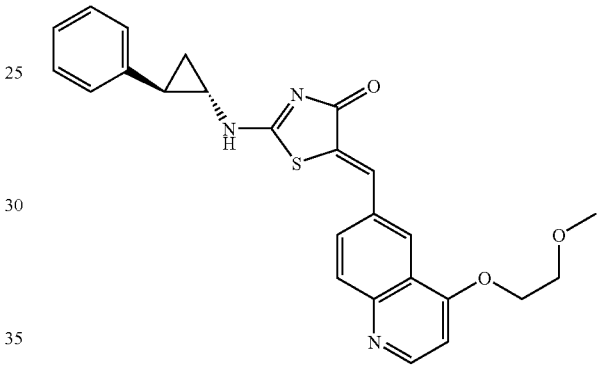

a) Preparation of 4-(2-methoxy-ethoxy)-quinoline-6-carbaldehyde

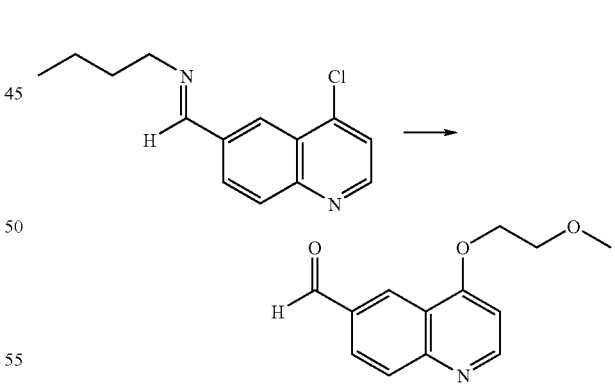

A mixture of butyl (4-chloro-quinolin-6-ylmethylene)-amine (preparation was described in example 27b) (250 mg, 1.01 mmol) and a solution of sodium (2-methoxy)-ethoxide in 2-methoxy-ethanol (2.5 mL, 10.0 mmol, 4.0M) were placed in a microwave tube and the mixture was heated to 120° C. for 30 min in a closed microwave. Then, the suspension was diluted with saturated ammonium chloride solution and the organic compound was extracted into ethyl acetate (3×50 mL). The combined extracts were washed with brine solution and dried over anhydrous magnesium sulfate. After filtration of the drying agent, the solvent was removed under the vacuum and the brown residue was dissolved in THF (2 mL) and 1 mL of HCl solution (3.0N) was added. The resulting solution was stirred for 1 h at room temperature. Then, it was neutralized with potassium carbonate solution and extracted with ethyl acetate (2×50 mL). The combined extracts were washed with brine solution and dried over anhydrous magnesium sulfate. After filtration of the drying agent, the solvent was removed under the vacuum and the brown residue was purified by using a Biotage silica gel column chromatography to obtain 160 mg (68.3% yield) of 4-(2-methoxy-ethoxy)-quinoline-6-carbaldehyde as a brown solid: EI-LRMS m/e calcd for $C_{13}H_{13}NO_3$ (M$^+$) 232.1, found 232.1.

b) Preparation of 5-[4-(2-methoxy-ethoxy)-quinolin-6-ylmeth-(Z)-ylidine]-2-((1R,2S)-2-phenyl-cyclopropylamino)-thiazol-4-one

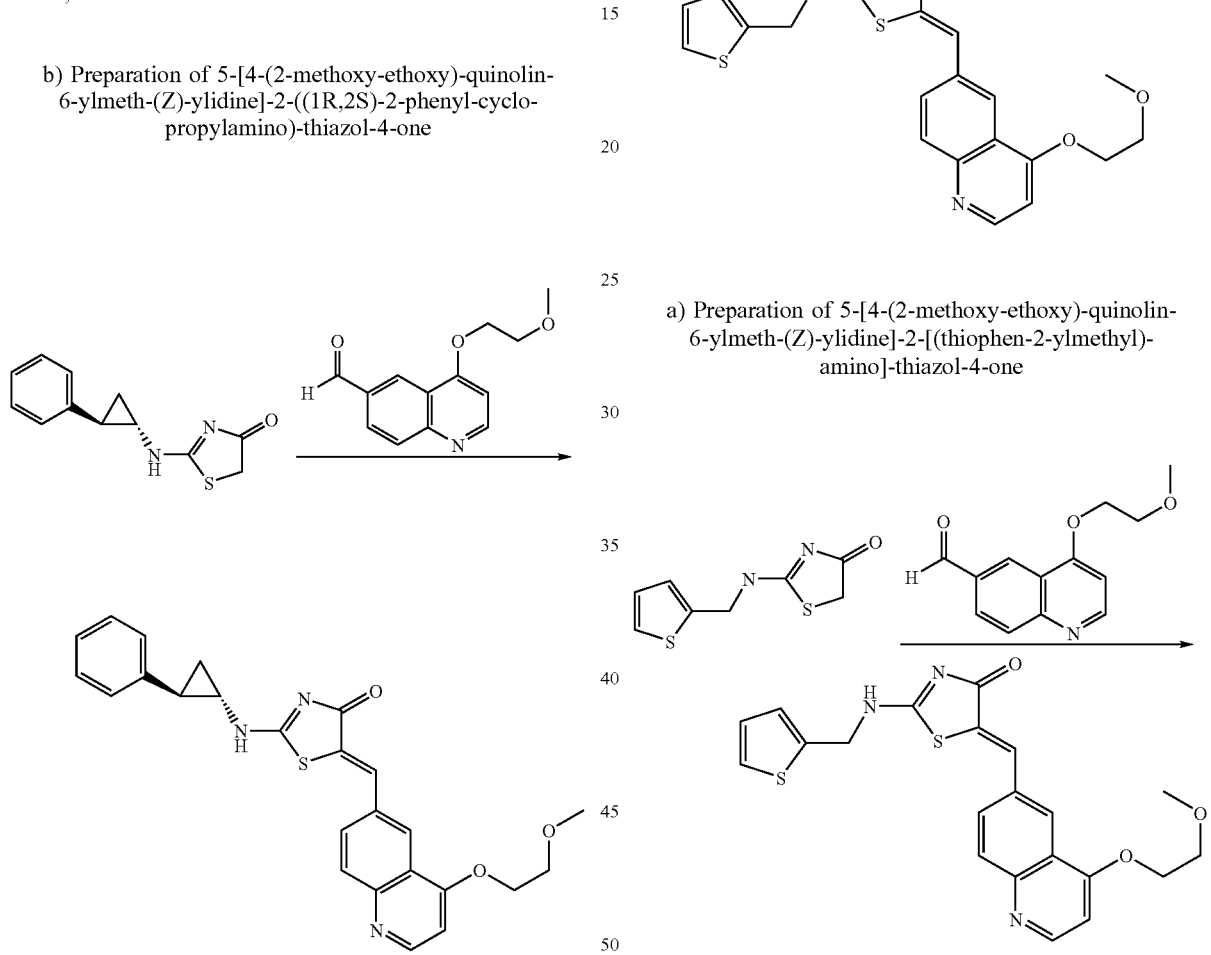

To a suspension of 2-((1R,2S)-2-phenyl-cyclopropylamino)-thiazol-4-one (preparation described in example 2a) (100 mg, 0.43 mmol) and 4-(2-methoxy-ethoxy)-quinoline-6-carbaldehyde (109.4 mg, 0.47 mmol) in toluene (1.0 mL) in a microwave tube were added benzoic acid (5.27 mg, 0.043 mmol) and piperidine (4.34 uL, 0.043 mmol) at room temperature. The microwave tube was sealed and heated to 150° C. in a closed microwave for 1 h. Then, the mixture was cooled to room temperature and diluted with toluene. The solids were collected by filtration and washed with toluene and dichloromethane. After drying in air, 116.6 mg (60.8% yield) of 5-[4-(2-methoxy-ethoxy)-quinolin-6-ylmeth-(Z)-ylidine]-2-((1R,2S)-2-phenyl-cyclopropylamino)-thiazol-4-one was isolated as a gray solid: HRES(+) m/e calcd for $C_{25}H_{23}N_3O_3S$ (M+H)$^+$446.1533, found 446.1535.

Example 17

5-[4-(2-Methoxy-ethoxy)-quinolin-6-ylmeth-(Z)-ylidine]-2-[(thiophen-2-ylmethyl)-amino]-thiazol-4-one a) Preparation of 5-[4-(2-methoxy-ethoxy)-quinolin-6-ylmeth-(Z)-ylidine]-2-[(thiophen-2-ylmethyl)-amino]-thiazol-4-one To a suspension of 2-[(thiophen-2-ylmethyl)-amino]-thiazol-4-one (preparation described in example 1 h) (45 mg, 0.212 mmol) and 4-(2-methoxy-ethoxy)-quinoline-6-carbaldehyde (53.93 mg, 0.233 mmol) in toluene (0.500 mL) in a microwave tube were added benzoic acid (2.6 mg, 0.021 mmol) and piperidine (2.14 uL, 0.021 mmol) at room temperature. The microwave tube was sealed and heated to 150° C. in a closed microwave for 1 h. Then, the mixture was cooled to room temperature and diluted with toluene. The solids were collected by filtration and washed with toluene and dichloromethane. After drying in air, 61 mg (67.6% yield) of 5-[4-(2-methoxy-ethoxy)-quinolin-6-ylmeth-(Z)-ylidine]-2-[(thiophen-2-ylmethyl)-amino]-thiazol-4-one was isolated as a brown solid: HRES(+) m/e calcd for $C_{21}H_{19}N_3O_3S_2$ (M+H)$^+$426.0941, found 426.0941.

Example 18

5-[4-(2-Methoxy-ethoxy)-quinolin-6-ylmeth-(Z)-ylidine]-2-(2-hydroxy-1-(R)-phenyl-ethylamino)-thiazol-4-one

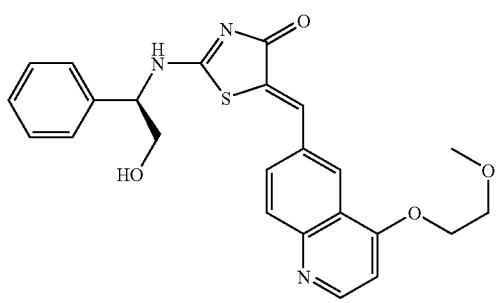

a) Preparation of 5-[4-(2-methoxy-ethoxy)-quinolin-6-ylmeth-(Z)-ylidine]-2-(2-hydroxy-1-(R)-phenyl-ethylamino)-thiazol-4-one

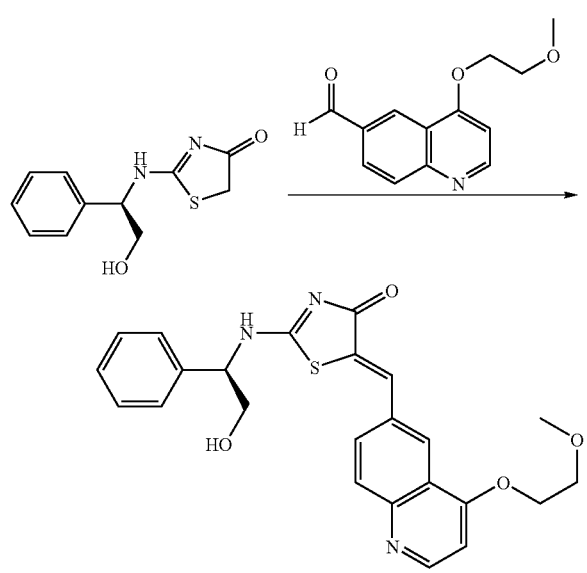

To a suspension of 2-(2-hydroxy-1-(R)-phenyl-ethylamino)-thiazol-4-one (preparation described in example 3a) (100 mg, 0.423 mmol) and 4-(2-methoxy-ethoxy)-quinoline-6-carbaldehyde (107.6 mg, 0.465 mmol) in toluene (1.0 mL) in a microwave tube were added benzoic acid (5.2 mg, 0.042 mmol) and piperidine (4.3 uL, 0.042 mmol) at room temperature. The microwave tube was sealed and heated to 150° C. in a closed microwave for 1 h. Then, the mixture was cooled to room temperature and diluted with dichloromethane. The solids were collected by filtration and washed with toluene and dichloromethane. After drying in air, 63 mg (33.1% yield) of 5-[4-(2-methoxy-ethoxy)-quinolin-6-ylmeth-(Z)-ylidine]-2-(2-hydroxy-1-(R)-phenyl-ethylamino)-thiazol-4-one was isolated as a light orange solid: HRES(+) m/e calcd for $C_{24}H_{23}N_3O_4S$ $(M+H)^+$ 450.1482, found 450.1481.

Example 19

2-Amino-5-(4-methoxy-quinolin-6-ylmeth-(Z)-ylidine)-thiazol-4-one as trifluoroacetate salt

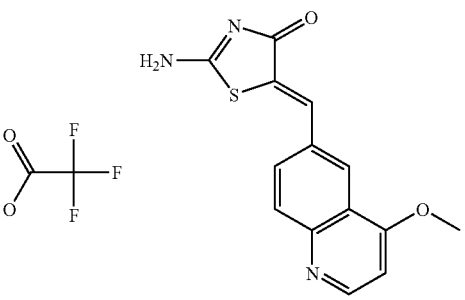

a) Preparation of (4-oxo-4,5-dihydro-thiazol-2-yl)-carbamic acid tert-butyl ester

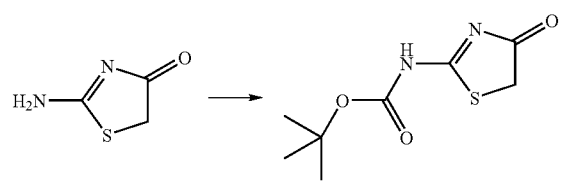

To a suspension of pseudothiohydantoin (10.13 g, 84.61 mmol) in acetonitrile (150 mL) were added Boc anhydride (20.32 g, 93.07 mmol) and DMAP (11.37 g, 93.07 mmol) at room temperature. The resulting mixture was stirred for 15 h at room temperature. Then, the precipitated solid particles were filtered and the solids were washed with dichloromethane. The filtrate was removed under the vacuum and the residue was purified by using a Biotage silica gel column chromatography to obtain 2.75 g (15% yield) of (4-oxo-4,5-dihydro-thiazol-2-yl)-carbamic acid tert-butyl ester as a white solid: EI-LRMS m/e calcd for $C_8H_{12}N_2O_3S$ $(M^-)$ 215.1, found 215.1.

b) Preparation of [5-(4-methoxy-quinolin-6-ylmeth-(Z)-ylidine)-4-oxo-4,5-dihydro-thiazol-2-yl]-carbamic acid tert-butyl ester

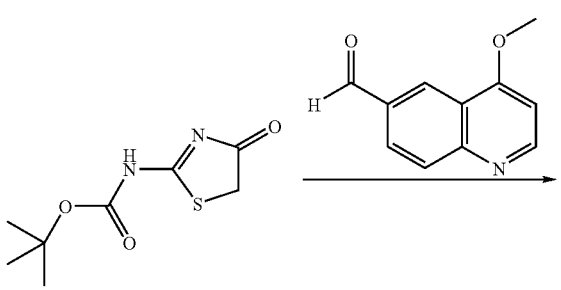

-continued

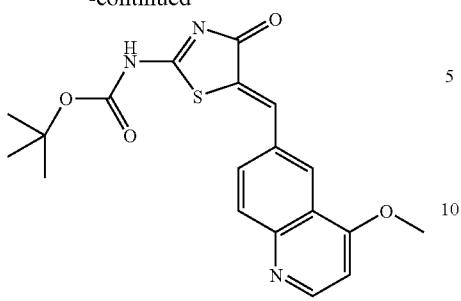

To a suspension of (4-oxo-4,5-dihydro-thiazol-2-yl)-carbamic acid tert-butyl ester (129 mg, 0.6 mmol) and 4-methoxy-quinoline-6-carbaldehyde (125 mg, 0.66 mmol) in toluene (1.5 mL) in a microwave tube were added benzoic acid (7.3 mg, 0.06 mmol) and piperidine (5.9 uL, 0.06 mmol) at room temperature. The microwave tube was sealed and heated to 150° C. in a closed microwave for 30 min. Then, the mixture was cooled to room temperature and diluted with toluene. The solids were collected by filtration and washed with toluene. After drying in air, 124 mg (53.6% yield) of [5-(4-methoxy-quinolin-6-ylmeth-(Z)-ylidine)$_4$-oxo-4,5-dihydro-thiazol-2-yl]-carbamic acid tert-butyl ester was isolated as a brown solid: LRES(+) m/e calcd for $C_{19}H_{19}N_3O_4S$ 386.0, found 386.0.

c) Preparation of 2-amino-5-(4-methoxy-quinolin-6-ylmeth-(Z)-ylidine)-thiazol-4-one as trifluoroacetate salt

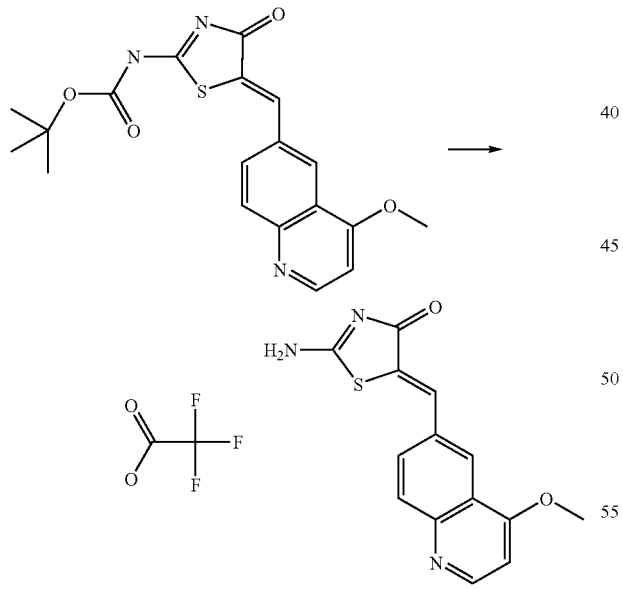

To a suspension of [5-(4-methoxy-quinolin-6-ylmeth-(Z)-ylidine)-4-oxo-4,5-dihydro-thiazol-2-yl]-carbamic acid tert-butyl ester (93 mg, 0.24 mmol) in dichloromethane (5 mL) was added trifluoroacetic acid (1 mL) at room temperature. The mixture was stirred for 2 h at room temperature and then the solvents were removed under the vacuum. The residue was purified by preparative HPLC to afford 12 mg (17% yield) of 2-amino-5-(4-methoxy-quinolin-6-ylmeth-(Z)-ylidine)-thiazol-4-one as trifluoroacetate salt as an yellow amorphous solid: EI-HRMS m/e calcd for $C_{14}H_{11}N_3O_2S$ $(M)^+$285.0572, found 285.0571.

Example 20

2-Amino-5-[4-(2-methoxy-ethoxy)-quinolin-6-yl-meth-(Z)-ylidine]-thiazol-4-one as trifluoroacetate salt

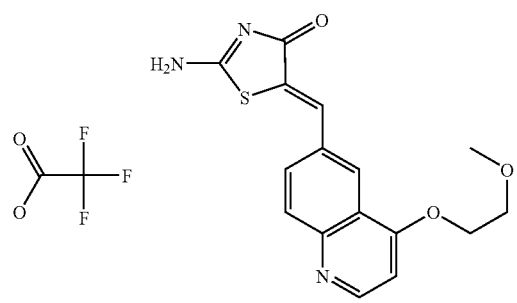

a) Preparation of [5-(4-(2-methoxy-ethoxy)-quinolin-6-ylmeth-(Z)-ylidine)-4-oxo-4,5-dihydro-thiazol-2-yl]-carbamic acid tert-butyl ester

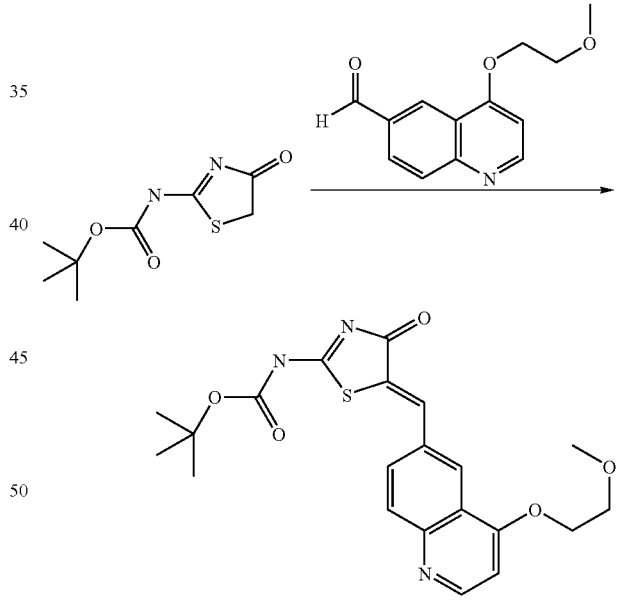

To a suspension of (4-oxo-4,5-dihydro-thiazol-2-yl)-carbamic acid tert-bytul ester (preparation was described in example 4a) (150 mg, 0.65 mmol) and 4-(2-methoxy-ethoxy)-quinoline-6-carbaldehyde (165 mg, 0.71 mmol) in toluene (2 mL) in a microwave tube were added benzoic acid (7.9 mg, 0.065 mmol) and piperidine (6.4 uL, 0.065 mmol) at room temperature. The microwave tube was sealed and heated to 150° C. in a closed microwave for 30 min. Then, the mixture was cooled to room temperature and diluted with toluene. The solids were collected by filtration and washed with toluene. After drying in air, 124 mg (70.3% yield) of [5-(4-(2-methoxy-ethoxy)-quinolin-6-ylmeth-(Z)- ylidine)-4-oxo-4,5-dihydro-thiazol-2-yl]-carbamic acid tert-butyl ester was isolated as a brown solid: LRMS-ES(+) m/e calcd for $C_{21}H_{23}N_3O_5S$ (M+H)$^+$430.1, found 430.1.

b) Preparation of 2-amino-5-[4-(2-methoxy-ethoxy)-quinolin-6-ylmeth-(Z)-ylidine]-thiazol-4-one as trifluoroacetate salt

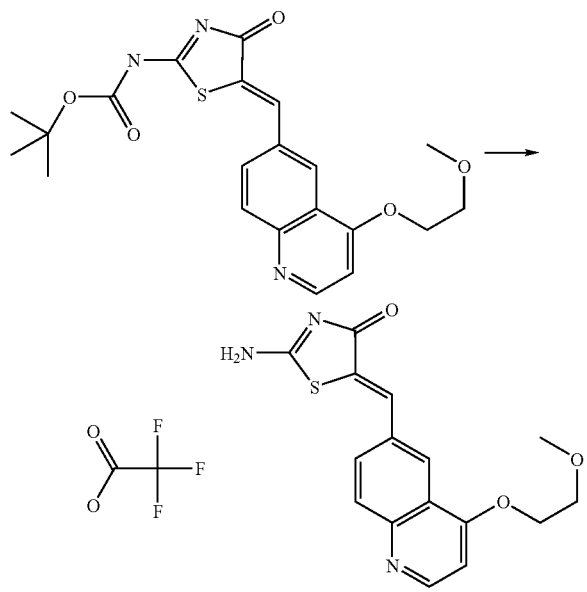

To a suspension of [5-(4-(2-methoxy-ethoxy)-quinolin-6-ylmeth-(Z)-ylidine)-4-oxo-4,5-dihydro-thiazol-2-yl]-carbamic acid tert-butyl ester (124 mg, 0.28 mmol) in dichloromethane (5 mL) was added trifluoroacetic acid (1 mL) at room temperature. The mixture was stirred for 2 h at room temperature and then the solvents were removed under the vacuum. The crude residue was suspended in toluene and ethyl acetate and triturated to obtain solids. The solids were collected by filtration and washed with ethyl acetate. Then, the yellow solids were purified by preparative HPLC to obtain 39 mg (42% yield) of 2-amino-5-[4-(2-methoxy-ethoxy)-quinolin-6-ylmeth-(Z)-ylidine]-thiazol-4-one as trifluoroacetate salt as an yellow amorphous solid: EI-HRMS m/e calcd for $C_{16}H_{15}N_3O_3S$ (M)$^+$329.0834, found 329.0832.

Example 21

2-(2-Chloro-benzylamino)-5-(4-ethoxy-quinolin-6-ylmeth-(Z)-ylidine)-thiazol-4-one

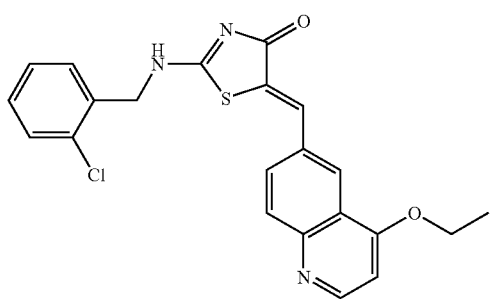

a) Preparation of 2-(2-chloro-benzylamino)-thiazol-4-one

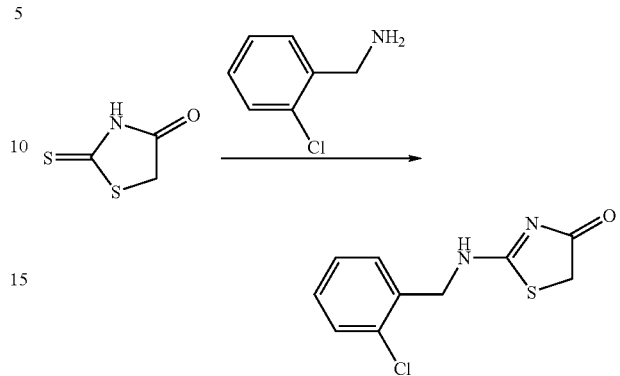

To a suspension of 2-chloro-benzylamine (7.88 g, 55 mmol) and Rhodanine (6.65 g, 50 mmol) in acetonitrile (150 mL) was added DIPEA (19.15 mL, 110 mmol) at room temperature. Then, this solution was cooled to 0° C. and mercuric chloride (13.5 g, 50 mmol) was added in three portions within a period of 15 min. After addition, the suspension was allowed to warm to room temperature and stirred for 3 days. The resulting black solids were filtered through a plug of celite and washed with dichloromethane (1 L) and methanol (500 mL). The combined solvents were removed under the vacuum and the crude residue was diluted with water (150 mL) and ethyl acetate (150 mL). After shaking, lot of solids formed which was collected by filtration to obtain 1.25 g of the desired product. Then, the two layers were separated and the ethyl acetate layer was washed with brine solution and dried over anhydrous magnesium sulfate. After filtration of the drying agent, the ethyl acetate solution was removed partially and the remaining solution was stored in the refrigerator. Then, the precipitated solids were collected by filtration to afford 2.67 g of the desired product. Then, the aqueous layer was again extracted with dichloromethane (2×150 mL). The combined dichloromethane extracts were washed with brine solution and dried over anhydrous magnesium sulfate. Filtration of the drying agent and removal of the solvent under the vacuum gave the crude residue which was purified by using a Biotage silica gel column chromatography to obtain 4.2 g (total product 8.12 g, 67.5% yield) of 2-(2-chloro-benzylamino)-thiazol-4-one as a white amorphous solid: EI-HRMS m/e calcd for $C_{10}H_9ClN_2OS$ (M$^+$) 240.0124, found 240.0122.

b) Preparation of 2-(2-chloro-benzylamino)-5-(4-ethoxy-quinolin-6-ylmeth-(Z)-ylidine)-thiazol-4-one

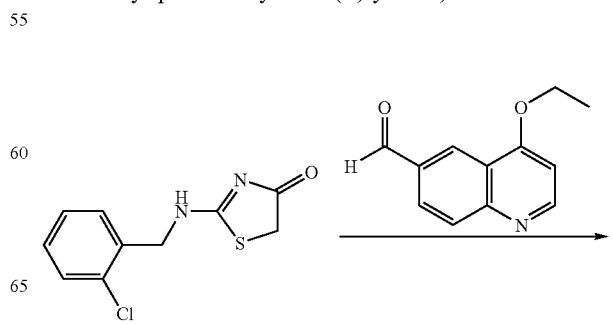

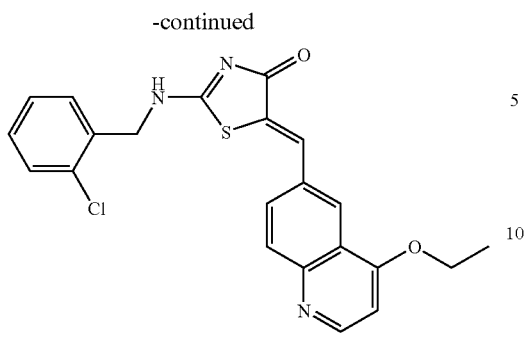

To a suspension of 2-(2-chloro-benzylamino)-thiazol-4-one (120 mg, 0.5 mmol) and 4-ethoxy-quinoline-6-carbaldehyde (120 mg, 0.6 mmol) in toluene (3 mL) in a microwave tube were added benzoic acid (7.5 mg, 0.06 mmol) and piperidine (5.9 uL, 0.06 mmol) at room temperature. The microwave tube was sealed and heated to 150° C. in a closed microwave for 30 min. Then, the mixture was cooled to room temperature and diluted with toluene. The solids were collected by filtration and washed with toluene. After drying in air, 110 mg (50% yield) of 2-(2-chloro-benzylamino)-5-(4-ethoxy-quinolin-6-ylmeth-(Z)-ylidine)-thiazol-4-one was isolated as an yellow solid. HRES(+) m/e calcd for $C_{22}H_{18}ClN_3O_2S$ (M+H)$^+$424.0881, found 424.0882.

Example 22

2-(2-Chloro-6-methyl-benzylamino)-5-(4-ethoxy-quinolin-6-ylmeth-(Z)-ylidine)-thiazol-4-one

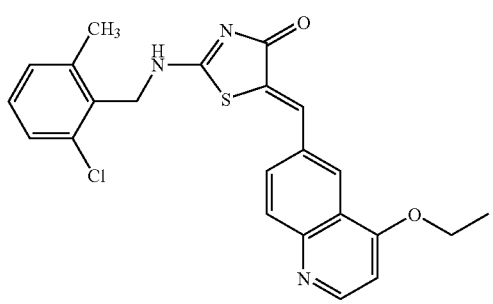

a) Preparation of 2-(2-chloro-6-methyl-benzylamino)-thiazol-4-one

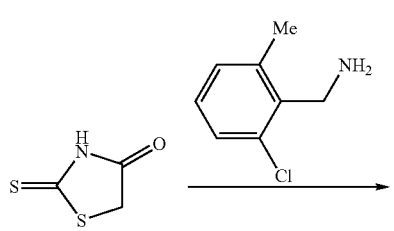

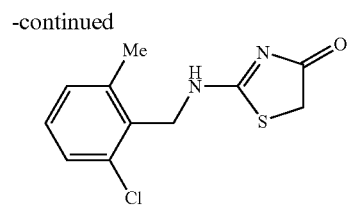

To a solution of 2-chloro-6-methyl-benzylamine (650 mg, 4.2 mmol) and Rhodanine (559 mg, 4.2 mmol) in acetonitrile (25 mL) was added DIPEA (1.74 mL, 10 mmol) at room temperature. Then, this solution was cooled to 0° C. and mercuric chloride (1.22 g, 4.5 mmol) was added in one portion. After addition, the suspension was allowed to warm to room temperature and stirred for 3 days. The resulting black solids were filtered through a plug of celite and washed with dichloromethane (500 mL) and methanol (250 mL). The combined solvents were removed under the vacuum and the crude residue was dissolved in ethyl acetate (25 mL) at hot condition and the solution was stored in the refrigerator overnight. Then, the solids were collected by filtration and washed with ethyl acetate. After drying in air, 305 mg (28.5% yield) of 2-(2-chloro-6-methyl-benzylamino)-thiazol-4-one was isolated as a white amorphous solid: EI-HRMS m/e calcd for $C_{11}H_{11}ClN_2OS$ (M$^+$) 254.0281, found 254.0282.

b) Preparation of 2-(2-chloro-6-methyl-benzylamino)-5-(4-ethoxy-quinolin-6-ylmeth-(Z)-ylidine)-thiazol-4-one

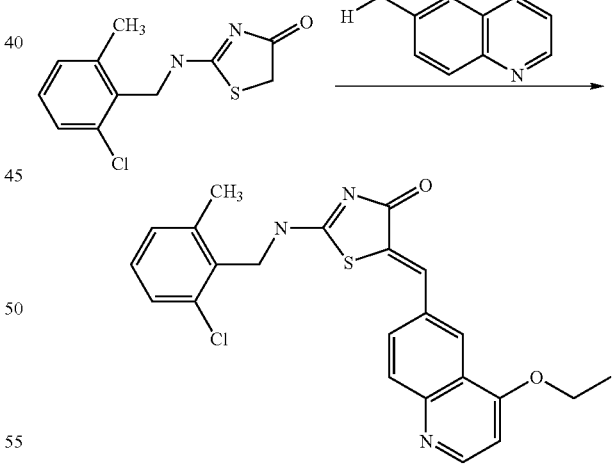

To a suspension of 2-(2-chloro-6-methyl-benzylamino)-thiazol-4-one (63 mg, 0.25 mmol) and 4-ethoxyquinoline-6-carbaldehyde (60 mg, 0.3 mmol) in toluene (2 mL) in a microwave tube were added benzoic acid (3.5 mg, 0.03 mmol) and piperidine (3 uL, 0.03 mmol) at room temperature. The microwave tube was sealed and heated to 150° C. in a closed microwave for 30 min. Then, the mixture was cooled to room temperature and diluted with toluene. The solids were collected by filtration and washed with toluene. After drying in air, 60 mg (50% yield) of 2-(2-chloro-6- methyl-benzylamino)-5-(4-ethoxy-quinolin-6-ylmeth-(Z)-ylidine)-thiazol-4-one was isolated as a light green solid. HRES(+) m/e calcd for $C_{23}H_{20}ClN_3O_2S$ (M+H)$^+$438.1038, found 438.1040.

Example 23

5-(4-Ethoxy-quinolin-6-ylmeth-(Z)-ylidine)-2-[(3-methyl-thiophen-2-ylmethyl)-amino]-thiazol-4-one

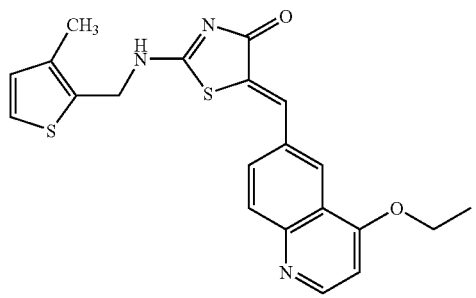

a) Preparation of 2-[(3-methyl-thiophen-2-ylmethyl)-amino]-thiazol-4-one

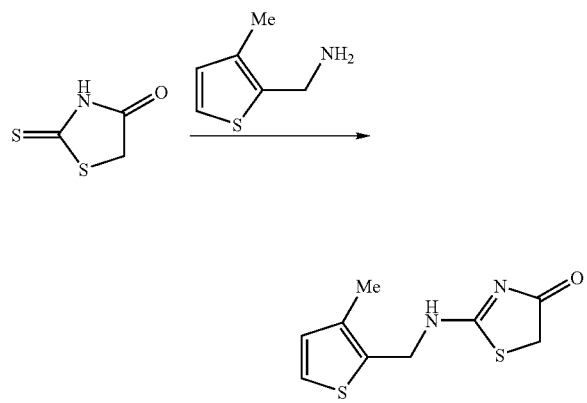

To a solution of 3-methyl-thiophen-2-ylmethylamine (700 mg, 5.5 mmol) and Rhodanine (732 mg, 5.5 mmol) in acetonitrile (30 mL) was added DIPEA (1.91 mL, 11 mmol) at room temperature. Then, this solution was cooled to 0° C. and mercuric chloride (1.52 g, 5.6 mmol) was added in one portion. After addition, the suspension was allowed to warm to room temperature and stirred for 3 days. The resulting black solids were filtered through a plug of celite and washed with acetonitrile (200 mL) and ethyl acetate (250 mL). The filtrates were removed under the vacuum and the crude residue was dissolved in dichloromethane (150 mL) and washed with water and brine solution. After drying over magnesium sulfate, the filtrate was removed under the vacuum and the residue was dissolved in dichloromethane (10 mL) and diluted with hexanes (10 mL). After overnight storage in the refrigerator, the solids were collected by filtration and washed with dichloromethane. After drying in air, 390 mg (31.5% yield) of 2-[(3-methyl-thiophen-2-ylm-ethyl)-amino]-thiazol-4-one was isolated as a light yellow amorphous solid: EI-HRMS m/e calcd for $C_9H_{10}N_2OS_2$ (M$^+$) 226.0235, found 226.0232.

b) Preparation of 5-(4-ethoxy-quinolin-6-ylmeth-(Z)-ylidine)-2-[(3-methyl-thiophen-2-ylmethyl)-amino]-thiazol-4-one

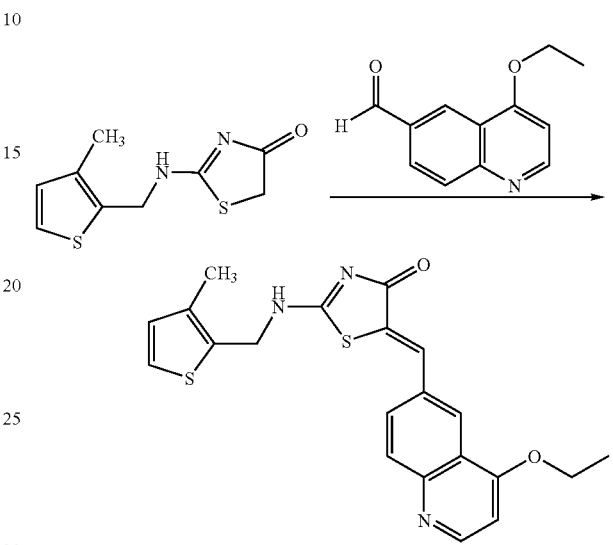

To a suspension of 2-[(3-methyl-thiophen-2-ylmethyl)-amino]-thiazol-4-one (57 mg, 0.25 mmol) and 4-ethoxy-quinoline-6-carbaldehyde (60 mg, 0.3 mmol) in toluene (2 mL) in a microwave tube were added benzoic acid (3.5 mg, 0.03 mmol) and piperidine (3 uL, 0.03 mmol) at room temperature. The microwave tube was sealed and heated to 150° C. in a closed microwave for 30 min. Then, the mixture was cooled to room temperature and diluted with toluene and the mixture was heated with heat gun. After cooling to room temperature, the solids were collected by filtration and washed with toluene. After drying in air, 50 mg (50% yield) of 2-[(3-methyl-thiophen-2-ylmethyl)-amino]-5-(4-ethoxy-quinolin-6-ylmeth-(Z)-ylidine)-thiazol-4-one was isolated as a green solid. HRES(+) m/e calcd for $C_{21}H_{19}N_3O_2S_2$ (M+H)$^+$410.0992, found 410.0995.

Example 24

5-(4-Phenoxy-quinolin-6-ylmeth-(Z)-ylidine)-2-[(thiophen-2-ylmethyl)-amino]-thiazol-4-one

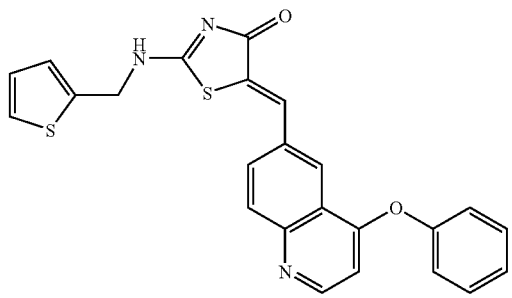

a) Preparation of 6-bromo-4-phenoxy-quinoline

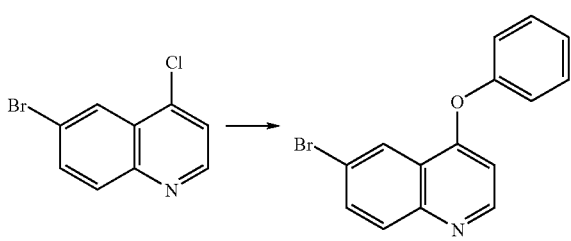

A mixture of 6-bromo-4-chloro-quinoline (1.5 g, 6.18 mmol) and sodium phenoxide (2.32 g, 24.74 mmol) in phenol (8.65 g) was heated to 150° C. in a sealed tube and stirred for 15 h. Then, the suspension was diluted with water and extracted with ethyl acetate (3×50 mL). The combined extracts were washed with 1.0N sodium hydroxide (3×50 mL), brine solution and dried over anhydrous magnesium sulfate. After filtration of the drying agent, the filtrate was removed under the vacuum and the residue was purified by using a Biotage silica gel column chromatography to afford 1.33 g (71.6% yield) of 6-bromo-4-phenoxy-quinoline as a light brown solid: EI-HRMS m/e calcd for $C_{15}H_{10}BrNO$ (M+) 298.9946, found 298.9946.

b) Preparation of 4-phenoxy-quinoline-6-carbaldehyde

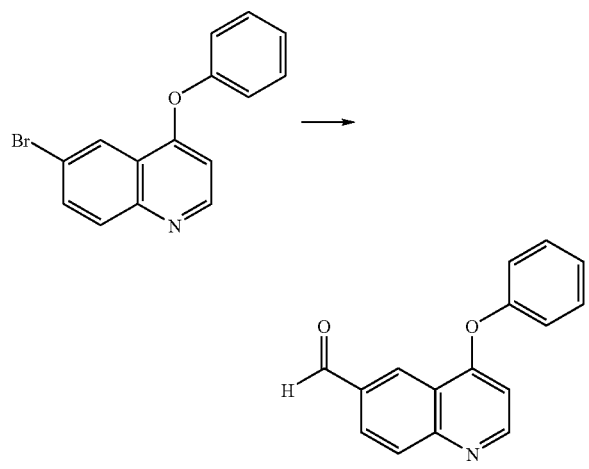

To a solution of 6-bromo-4-phenoxy-quinoline (1.12 g, 3.73 mmol) in THF (15 mL) was added dropwise a 2.5M solution of n-butyllithium in hexanes (1.64 mL, 4.10 mmol, 1.1 equiv.) at −70° C. During the addition, the color of the solution was turned into brown and this solution was stirred for 20 min at this temperature. Then, a neat dimethylformamide (0.576 mL, 7.46 mmol) was added dropwise. After addition, the mixture was allowed to warm to room temperature and stirred for 2 h. Then, the mixture was diluted with saturated ammonium chloride solution and the two layers were separated. The aqueous layer was extracted with ethyl acetate (2×75 mL). The combined organic extracts were washed with brine solution and dried over anhydrous magnesium sulfate. Filtration of the drying agent and removal of the solvent under the vacuum gave the crude residue which was purified by using a Biotage silica gel column chromatography to afford 0.250 g (27% yield) of 4-phenoxy-quinoline-6-carbaldehyde as a white solid: mp 112-115° C.; EI-HRMS m/e calcd for $C_{16}H_{11}NO_2$ (M+) 249.0790, found 249.0787.

c) Preparation of 5-(4-phenoxy-quinolin-6-ylmeth-(Z)-ylidine)-2-[(thiophen-2-ylmethyl)-amino]-thiazol-4-one

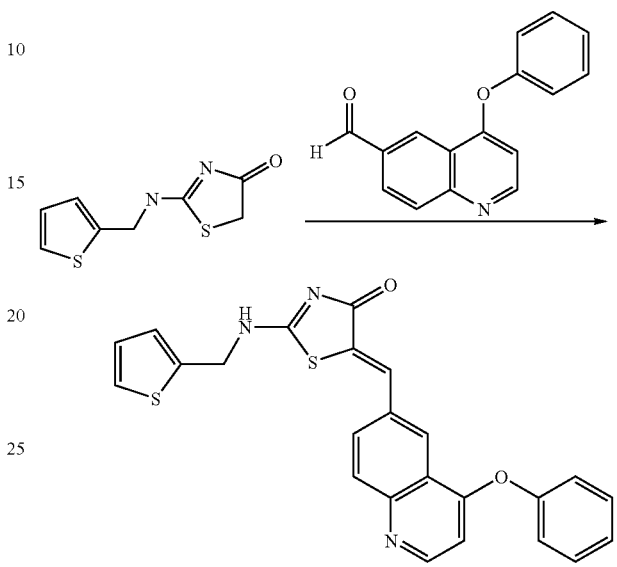

To a suspension of 2-[(thiophen-2-ylmethyl)-amino]-thiazol-4-one (preparation described in example 1 h) (60 mg, 0.283 mmol) and 4-phenoxy-quinoline-6-carbaldehyde (77.6 mg, 0.311 mmol) in toluene (1.0 mL) in a microwave tube were added benzoic acid (3.47 mg, 0.028 mmol) and piperidine (2.85 uL, 0.029 mmol) at room temperature. The microwave tube was sealed and heated to 150° C. in a closed microwave for 30 min. Then, the mixture was cooled to room temperature and diluted with toluene. The solids were collected by filtration and washed with toluene and acetonitrile. After drying in air, 41 mg (32.7% yield) of 5-(4-phenoxy-quinolin-6-ylmeth-(Z)-ylidine)-2-[(thiophen-2-ylmethyl)-amino]-thiazol-4-one was isolated as a brown solid: mp 239-240.5° C.; HRES(+) m/e calcd for $C_{24}H_{17}N_3O_2S_2$ $(M+H)^+$ 444.0835, found 444.0837.

Example 25

2-Amino-5-(4-phenoxy-quinolin-6-ylmeth-(Z)-ylidine)-thiazol-4-one

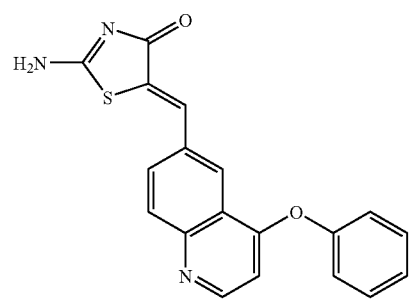

a) Preparation of [5-(4-phenoxy-quinolin-6-ylmeth-(Z)-ylidine)-4-oxo-4,5-dihydro-thiazol-2-yl]-carbamic acid tert-butyl ester

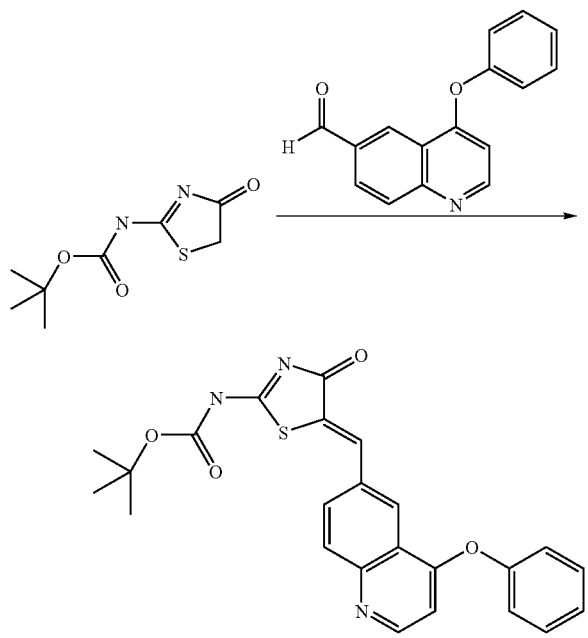

To a suspension of (4-oxo-4,5-dihydro-thiazol-2-yl)-carbamic acid tert-bytul ester (preparation was described in example 4a) (150 mg, 0.694 mmol) and 4-phenoxy-quinoline-6-carbaldehyde (190 mg, 0.76 mmol) in toluene (2.5 mL) in a microwave tube were added benzoic acid (8.52 mg, 0.069 mmol) and piperidine (7.01 uL, 0.071 mmol) at room temperature. The microwave tube was sealed and heated to 150° C. in a closed microwave for 30 min. Then, the mixture was cooled to room temperature and diluted with toluene. The solids were collected by filtration and washed with toluene, acetonitrile and dichloromethane. After drying in air, 128 mg (41.2% yield) of [5-(4-phenoxy-quinolin-6-ylmeth-(Z)-ylidine)-4-oxo-4,5-dihydro-thiazol-2-yl]-carbamic acid tert-butyl ester was isolated as a brown solid: LRES(+) m/e calcd for $C_{24}H_{21}N_3O_4S$ 448.1, found 448.1.

b) Preparation of 2-amino-5-(4-phenoxy-quinolin-6-ylmeth-(Z)-ylidine)-thiazol-4-one

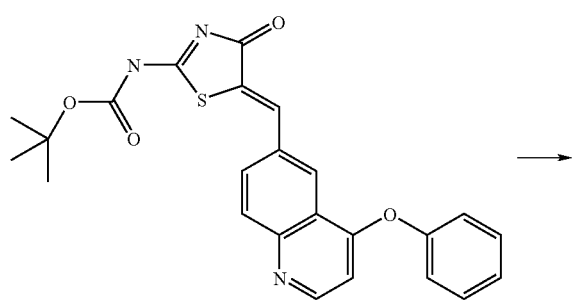

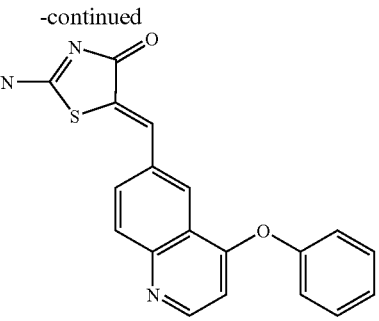

To a suspension of [5-(4-phenoxy-quinolin-6-ylmeth-(Z)-ylidine)$_4$-oxo-4,5-dihydro-thiazol-2-yl]-carbamic acid tert-butyl ester (121.3 mg, 0.27 mmol) in dichloromethane (5 mL) was added trifluoroacetic acid (1 mL) at room temperature. The mixture was stirred for 4 h at room temperature and then the mixture was diluted with diethyl ether to afford a suspension. The solids were collected by filtration and washed with diethyl ether. Then, the solids were purified by preparative HPLC to obtain the final compound as a trifluoroacetate salt. The salt was dissolved in water and neutralized with saturated sodium bicarbonate solution. Then, the solids were collected by filtration and washed with water. After drying in air, 55 mg (44% yield) of 2-amino-5-(4-phenoxy-quinolin-6-ylmeth-(Z)-ylidine)-thiazol-4-one was isolated as a light brown solid: HRES(+) m/e calcd for $C_{19}H_{13}N_3O_2S$ (M+H)$^+$348.0801, found 348.0800.

Example 26

2-(2-Chloro-4-fluoro-benzylamino)-5-(4-ethoxy-quinolin-6-ylmeth-(Z)-ylidine)-thiazol-4-one

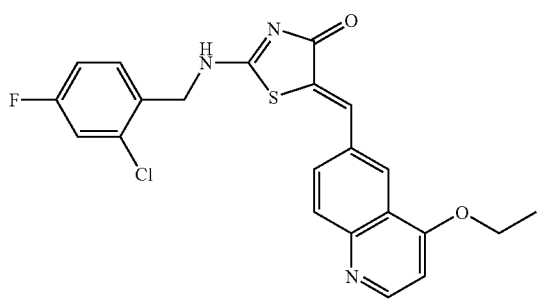

a) Preparation of 2-(2-chloro-4-fluoro-benzylamino)-thiazol-4-one

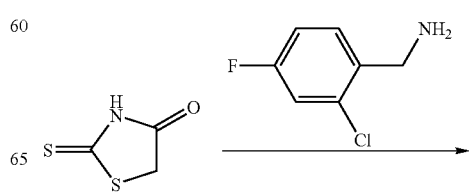

-continued

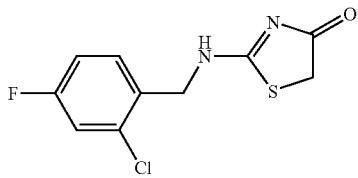

To a solution of 2-chloro-4-fluoro-benzylamine (4.5 g, 28.19 mmol) and Rhodanine (3.75 g, 28.2 mmol) in acetonitrile (170 mL) was added DIPEA (9.82 mL, 56.4 mmol) at room temperature. Then, this solution was cooled to 0° C. and mercuric chloride (8.42 g, 31.02 mmol) was added in two portions within 10 min. After addition, the suspension was allowed to warm to room temperature and stirred for 3 days. The resulting black solids were filtered through a plug of celite and washed with acetonitrile (1.0 L) and ethyl acetate (500 mL). The combined filtrates were removed under the vacuum and the crude residue was dissolved in ethyl acetate (150 mL) and washed with water and brine solution. After drying over magnesium sulfate, the filtrate was removed under the vacuum and the residue was dissolved in ethyl acetate (50 mL) at hot condition. After cooling in the refrigerator overnight, the solids were collected by filtration and washed with hexanes. After drying in air, 1.2 g (16.5% yield) of 2-(2-chloro-4-fluoro-benzylamino)-thiazol-4-one was isolated as a white amorphous solid: EI-HRMS m/e calcd for $C_{10}H_8FN_2OS_2$ (M$^+$) 258.0030, found 258.0027.

b) Preparation of 2-(2-chloro-4-fluoro-benzylamino)-5-(4-ethoxy-quinolin-6-ylmeth-(Z)-ylidine)-thiazol-4-one To a suspension of 2-(2-chloro-4-fluoro-benzylamino)-thiazol-4-one (130 mg, 0.5 mmol) and 4-ethoxy-quinoline-6-carbaldehyde (120 mg, 0.6 mmol) in toluene (4 mL) in a microwave tube were added benzoic acid (7.5 mg, 0.06 mmol) and piperidine (6 uL, 0.06 mmol) at room temperature. The microwave tube was sealed and heated to 150° C. in a closed microwave for 30 min. Then, the mixture was cooled to room temperature and diluted with toluene (2 mL) and acetonitrile (2 mL) and the mixture was heated with heat gun. After cooling to room temperature, the solids were collected by filtration and washed with toluene. After drying in air, 98 mg (44.5% yield) of 2-(2-chloro-4-fluoro-benzylamino)-5-(4-ethoxy-quinolin-6-ylmeth-(Z)-ylidine)-thiazol-4-one was isolated as a gray solid. HRES(+) m/e calcd for $C_{22}H_{17}ClFN_3O_2S$ (M+H)$^+$442.0787, found 442.0787.

Example 27

5-(4-Phenoxy-quinolin-6-ylmeth-(Z)-ylidine)-2-((1R,2S)-2-phenyl-cyclopropylamino)-thiazol-4-one

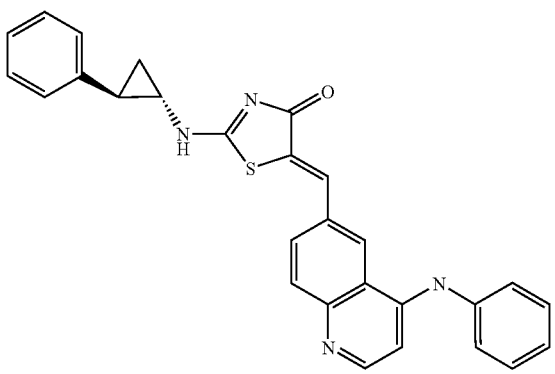

a) Preparation of 5-(4-phenoxy-quinolin-6-ylmeth-(Z)-ylidine)-2-((1R,2S)-2-phenyl-cyclopropylamino)-thiaol-4-one

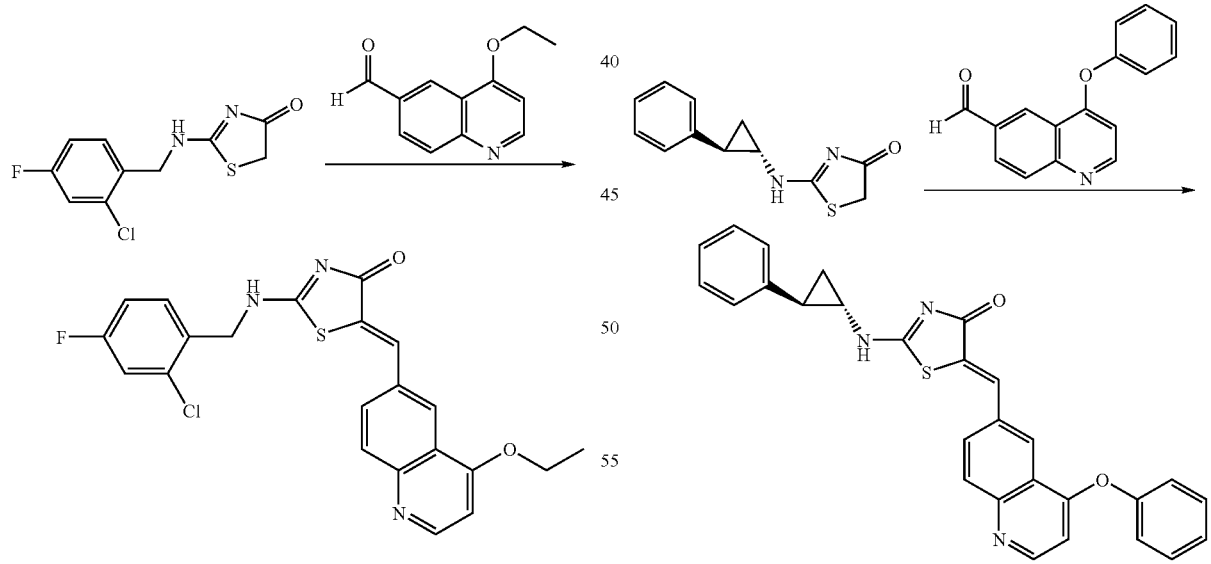

To a suspension of 2-((1R,2S)-2-phenyl-cyclopropylamino)-thiazol-4-one (preparation described in example 2a) (100 mg, 0.43 mmol) and 4-phenoxy-quinoline-6-carbaldehyde (117.9 mg, 0.473 mmol) in toluene (2 mL) in a microwave tube were added benzoic acid (5.28 mg, 0.043 mmol) and piperidine (4.34 uL, 0.043 mmol) at room temperature. The microwave tube was sealed and heated to 150° C. in a closed microwave for 30 min. Then, the mixture was cooled to room temperature and diluted with toluene. The solids were collected by filtration and washed with toluene, acetonitrile and dichloromethane. After drying in air, 106.6 mg (53.4% yield) of 5-(4-phenoxy-quinolin-6-ylmeth-(Z)-ylidine)-2-((1R,2S)-2-phenyl-cyclopropylamino)-thiazol-4-one was isolated as a brown solid: HRES (+) m/e calcd for $C_{28}H_{21}N_3O_2S$ (M+H)$^+$464.1427, found 464.1417.

Example 28

5-(4-Butoxy-quinolin-6-ylmeth-(Z)-ylidine)-2-((1R,2S)-2-phenyl-cyclopropylamino)-thiazol-4-one

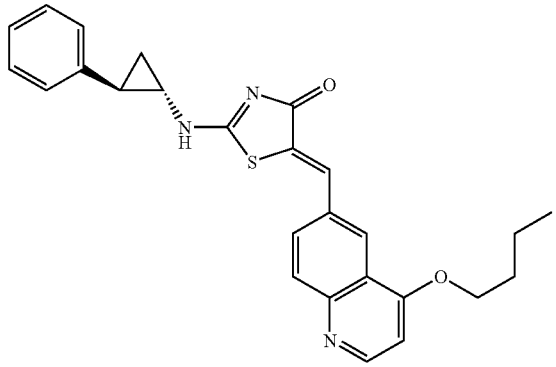

a) Preparation of 4-chloro-quinoline-6-carbaldehyde

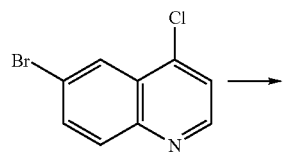

To a solution of 6-bromo-4-chloro-quinoline (3.0 g, 12.37 mmol) in THF (60 mL) was added dropwise a 2.5M solution of n-butyllithium in hexanes (5.95 mL, 14.84 mmol, 1.1 equiv.) at −70° C. During the addition, the color of the solution was turned to red and then it was stirred for 1 h at this temperature. Then, a solution of dimethylformamide (1.91 mL, 24.74 mmol) in THF (10 mL) was added dropwise. After addition, the mixture was allowed to warm to room temperature and stirred for 2 h. The mixture was diluted with saturated ammonium chloride solution and the two layers were separated. The aqueous layer was extracted with ethyl acetate (2×100 mL). The combined organic extracts were washed with brine solution and dried over anhydrous magnesium sulfate. Filtration of the drying agent and removal of the solvent under the vacuum gave the crude brown solid which was purified by using a Biotage silica gel column chromatography to obtain 0.6 g (25% yield) of 4-chloro-quinoline-6-carbaldehyde as a white solid: EI-HRMS m/e calcd for $C_{10}H_6ClNO$ (M$^+$) 187.0633, found 187.0638.

b) Preparation of butyl (4-chloro-quinolin-6-ylmethylene)-amine

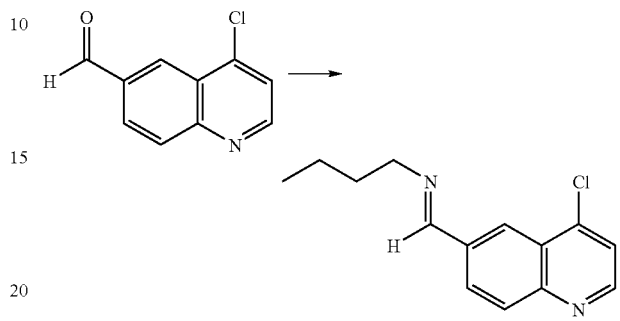

To a suspension of 4-chloro-quinoline-6-carbaldehyde (3.59 g, 18.73 mmol) in heptanes (36 mL) was added n-butylamine(1.51 g, 20.60 mmol, 1.1 equiv.) at room temperature. The reaction mixture was stirred for 5 h at room temperature by this time all solids were dissolved and gave a light brown solution containing a little oily stuff on the wall of flask. Then, 4 mL of THF was added and the clear solution was stirred for another 15 h. This solution was diluted with ethyl acetate (50 mL) and washed with brine solution and dried over anhydrous magnesium sulfate. After filtration of the drying agent, the solvents were removed under the vacuum and the remaining residue was dried under high vacuum to afford 4.62 g (~100% yield) of butyl (4-chloro-quinolin-6-ylmethylene)-amine as a brown oil which was used directly for the next substitution reaction. LRMS(+) m/e calcd for $C_{14}H_{15}ClN_2$ (M+H)$^+$247.7, found 247.2.

c) Preparation of 4-butoxy-quinoline-6-carbaldehyde

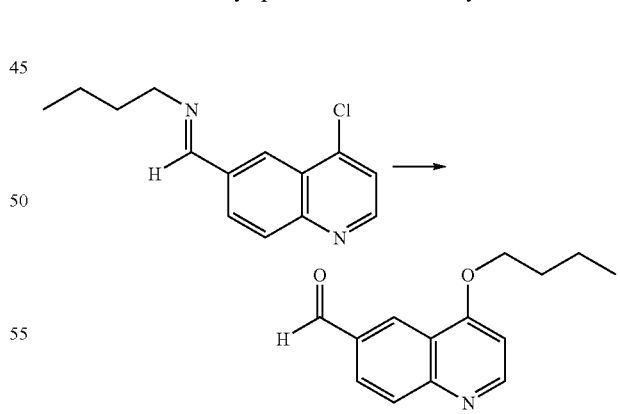

A mixture of butyl (4-chloro-quinolin-6-ylmethylene)-amine (322 mg, 1.3 mmol) and a solution of sodium butoxide in butanol (3 mL, 6.0 mmol, 2.0M) were placed in a microwave tube and the mixture was heated to 120° C. for 30 min in a closed microwave. Then, the suspension was diluted with 3.0N hydrochloric acid (3 mL) and the solvent was removed under the vacuum. The residue was diluted with water and the organic compound was extracted into d) Preparation of 5-(4-butoxy-quinolin-6-ylmeth-(Z)-ylidine)-2-((1R,2S)-2-phenyl-cyclopropylamino)-thiazol-4-one

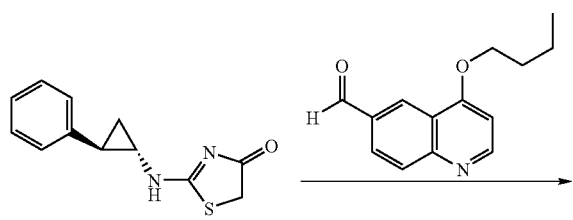

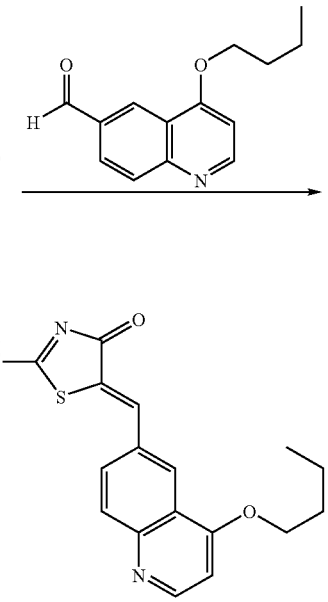

To a suspension of 2-((1R,2S)-2-phenyl-cyclopropylamino)-thiazol-4-one (preparation described in example 2a) (30 mg, 0.13 mmol) and 4-butoxy-quinoline-6-carbaldehyde (32.5 mg, 0.14 mmol) in toluene (0.500 mL) in a microwave tube were added benzoic acid (1.6 mg, 0.013 mmol) and piperidine (1.3 uL, 0.013 mmol) at room temperature. The microwave tube was sealed and heated to 150° C. in a closed microwave for 30 min. Then, the mixture was cooled to room temperature and diluted with toluene. The solids were collected by filtration and washed with toluene, acetonitrile and dichloromethane. After drying in air, 37.3 mg (65% yield) of 5-(4-butoxy-quinolin-6-ylmeth-(Z)-ylidine)-2-((1R,2S)-2-phenyl-cyclopropylamino)-thiazol-4-one was isolated as a brown solid: HRES(+) m/e calcd for $C_{26}H_{25}N_3O_2S$ (M+H)$^+$444.1740, found 444.1735.

Example 29

2-Amino-5-(4-butoxy-quinolin-6-ylmeth-(Z)-ylidine)-thiazol-4-one

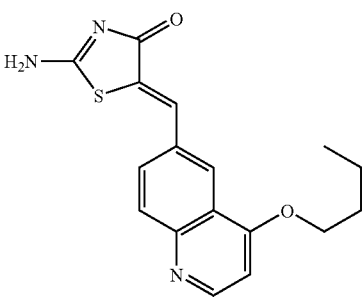

a) Preparation of [5-(4-butoxy-quinolin-6-ylmeth-(Z)-ylidine)$_4$-oxo-4,5-dihydro-thiazol-2-yl]-carbamic acid tert-butyl ester To a suspension of (4-oxo-4,5-dihydro-thiazol-2-yl)-carbamic acid tert-bytul ester (preparation was described in example 4a) (90 mg, 0.42 mmol) and 4-butoxy-quinoline-6-carbaldehyde (95.38 mg, 0.42 mmol) in toluene (1.66 mL) in a microwave tube were added benzoic acid (5.11 mg, 0.042 mmol) and piperidine (4.2 uL, 0.042 mmol) at room temperature. The microwave tube was sealed and heated to 150° C. in a closed microwave for 30 min. Then, the mixture was cooled to room temperature and diluted with toluene. The solids were collected by filtration and washed with toluene, acetonitrile and dichloromethane. After drying in air, 77.9 mg (43.8% yield) of [5-(4-butoxy-quinolin-6-ylmeth-(Z)-ylidine)$_4$-oxo-4,5-dihydro-thiazol-2-yl]-carbamic acid tert-butyl ester was isolated as a brown solid.

b) Preparation of 2-amino-5-(4-butoxy-quinolin-6-ylmeth-(Z)-ylidine)-thiazol-4-one a) Preparation of 2-[(5-methyl-pyrazin-2-ylmethyl)-amino]-thiazol-4-one

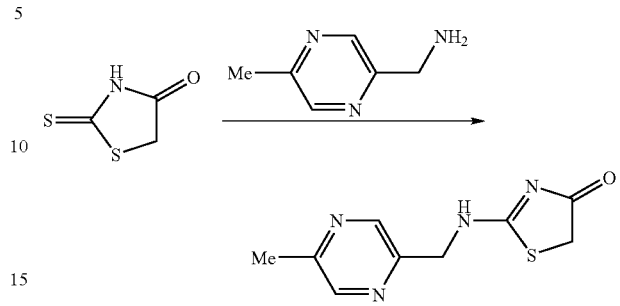

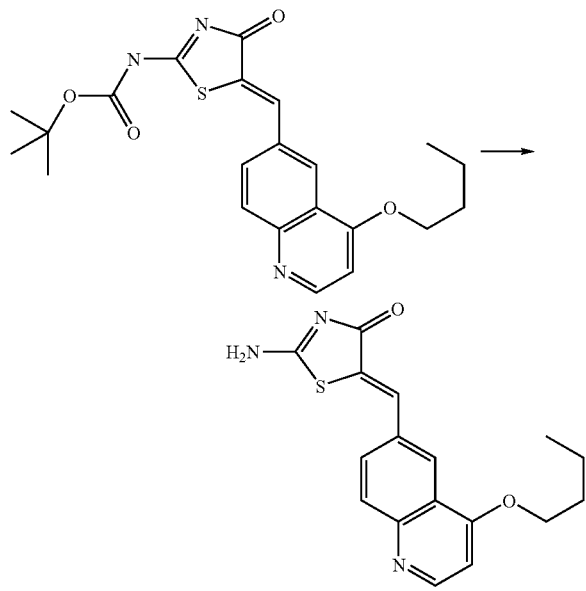

To a solution of 2-(aminomethyl)-5-methyl-pyrazine (3.69 g, 30 mmol) and Rhodanine (3.59 g, 27 mmol) in acetonitrile (100 mL) was added DIPEA (10.45 mL, 60 mmol) at room temperature. Then, this solution was cooled to 0° C. and mercuric chloride (8.15 g, 30 mmol) was added in two portions within 10 min. After addition, the suspension was allowed to warm to room temperature and stirred for 3 days. The resulting black solids were filtered through a plug of celite and washed with acetonitrile (1.0 L) and ethyl acetate (500 mL). The combined solvents were removed under the vacuum and the crude residue was dissolved in acetonitrile (25 mL) at hot condition. After cooling in the refrigerator overnight, the solids were collected by filtration and washed with acetonitrile. After drying in air, 1.5 g (25% yield) of 2-[(5-methyl-pyrazin-2-ylmethyl)-amino]-thiazol-4-one was isolated as a white solid: HRES(+) m/e calcd for $C_9H_{10}N_4OS$ (M+H)$^+$223.0648, found 223.0648.

To a suspension of [5-(4-butoxy-quinolin-6-ylmeth-(Z)-ylidine)-4-oxo-4,5-dihydro-thiazol-2-yl]-carbamic acid tert-butyl ester (72.9 mg, 0.17 mmol) in dichloromethane (3 mL) was added trifluoroacetic acid (0.532 mL) at room temperature. The mixture was stirred for 4 h at room temperature and then the mixture was diluted with diethyl ether to afford a suspension. The solids were collected by filtration and washed with diethyl ether. Then, this solid was purified by preparative HPLC to obtain the final compound as a trifluoroacetate salt. The salt was dissolved in water and neutralized with saturated sodium bicarbonate solution. Then, the solids were collected by filtration and washed with water. After drying in air, 4.5 mg (6% yield) of 2-amino-5-(4-butoxy-quinolin-6-ylmeth-(Z)-ylidine)-thiazol-4-one was isolated as a light brown solid: EI-HRMS m/e calcd for $C_{17}H_{17}N_3O_2S$ (M)$^+$327.1041, found 327.1038.

b) Preparation of 2-[(5-methyl-pyrazin-2-ylmethyl)-amino]-5-(4-ethoxy-quinolin-6-ylmeth-(Z)-ylidine)-thiazol-4-one Example 30

2-[(5-Methyl-pyrazin-2-ylmethyl)-amino]-5-(4-ethoxy-quinolin-6-ylmeth-(Z)-ylidine)-thiazol-4-one

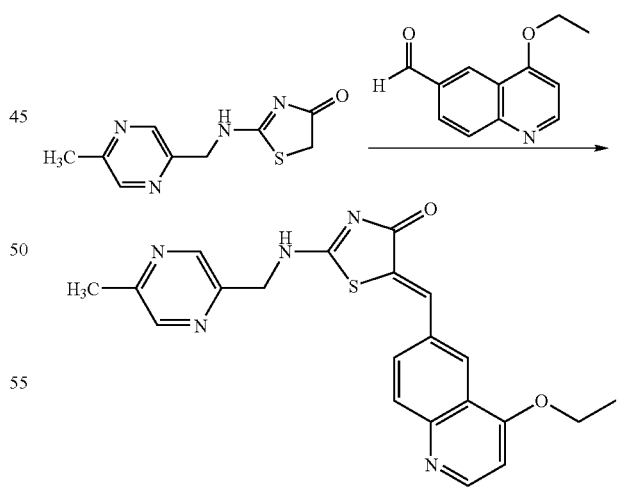

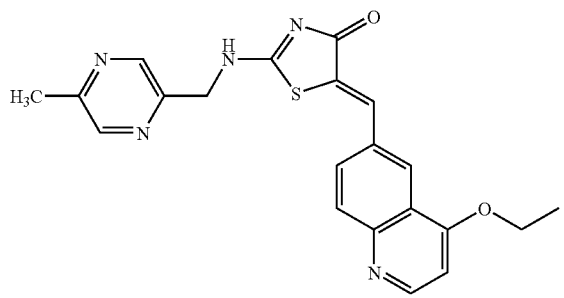

To a suspension of 2-[(5-methyl-pyrazin-2-ylmethyl)-amino]-thiazol-4-one (112 mg, 0.5 mmol) and 4-ethoxy-quinoline-6-carbaldehyde (120 mg, 0.6 mmol) in toluene (4 mL) in a microwave tube were added benzoic acid (7.5 mg, 0.06 mmol) and piperidine (6 uL, 0.06 mmol) at room temperature. The microwave tube was sealed and heated to 150° C. in a closed microwave for 30 min. Then, the mixture was cooled to room temperature and diluted with toluene and acetonitrile and the mixture was heated with heat gun. After cooling to room temperature, the solids were collected by filtration and washed with acetonitrile. After drying in air, 43 mg (21% yield) of 2-[(5-methyl-pyrazin-2-ylmethyl)-amino]-5-(4-ethoxy-quinolin-6-ylmeth-(Z)-ylidine)-thiazol-4-one was isolated as a green solid. HRES(+) m/e calcd for $C_{21}H_{19}N_5O_2S$ (M+H)$^+$406.1332, found 406.1331.

Example 31

5-(4-Ethoxy-quinolin-6-ylmeth-(Z)-ylidine)-2-[2-(4-hydroxy-phenyl)-ethylamino]-thiazol-4-one

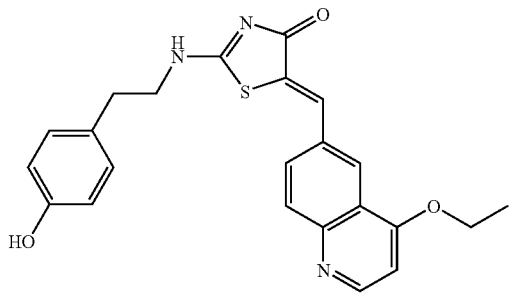

a) Preparation of 2-[2-(4-hydroxy-phenyl)-ethylamino]-thiazol-4-one

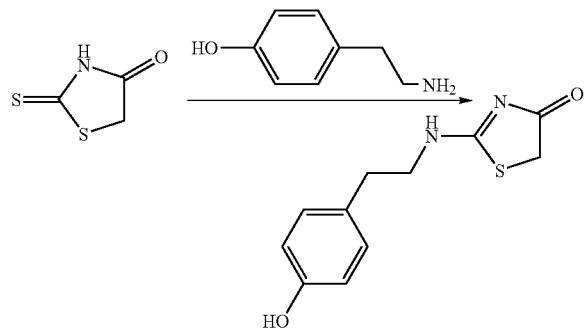

To a suspension of (4-hydroxy-phenyl)-ethylamine (3.14 g, 22.2 mmol) and Rhodanine (2.96 g, 22.2 mmol) in ethanol (314 mL) was added DIPEA (4.76 mL, 26.64 mmol) at room temperature. Then, this solution was cooled to 0° C. and mercuric chloride (6.05 g, 22.2 mmol) was added in two portions within a period of 10 min. After addition, the suspension was allowed to warm to room temperature and stirred for 15 h. The resulting black solids were filtered through a plug of celite and washed with dichloromethane (200 mL) and methanol (500 mL). The combined solvents were removed under the vacuum and the crude residue was diluted with water (150 mL) and ethyl acetate (150 mL). The two layers were separated and the aqueous layer was extracted with ethyl acetate (2×100 mL). The combined organic extracts were washed with brine solution and dried over anhydrous magnesium sulfate. Filtration of the drying agent and removal of the solvent under the vacuum gave the crude residue which was purified by using Biotage silica gel column chromatography to afford 1.0 g (19% yield) of 2-[2-(4-hydroxy-phenyl)-ethylamino]-thiazol-4-one as a white amorphous solid: HRES(+) m/e calcd for $C_{10}H_8ClFN_2OS$ (M+H)$^+$237.0692, found 237.0693.

b) Preparation of 5-(4-ethoxy-quinolin-6-ylmeth-(Z)-ylidine)-2-[2-(4-hydroxy-phenyl)-ethylamino]-thiazol-4-one

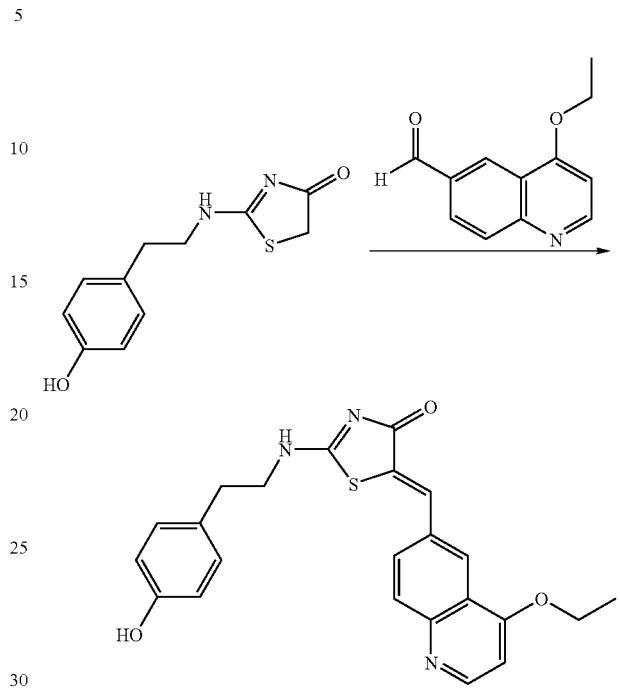

To a suspension of 2-[2-(4-hydroxyphenyl)-ethylamino]-thiazol-4-one (100 mg, 0.42 mmol) and 4-ethoxyquinoline-6-carbaldehyde (93.63 mg, 0.465 mmol) in dimethylformamide (2 mL) in a microwave tube were added benzoic acid (5.19 mg, 0.042 mmol) and piperidine (4.27 uL, 0.042 mmol) at room temperature. The microwave tube was sealed and heated to 150° C. in a closed microwave for 30 min. Then, the brown mixture was cooled to room temperature and diluted with acetonitrile to afford suspension. Then, the solids were collected by filtration and washed with acetonitrile. After drying in air, 25 mg (14% yield) of 5-(4-ethoxy-quinolin-6-ylmeth-(Z)-ylidine)-2-[2-(4-hydroxy-phenyl)-ethylamino]-thiazol-4-one was isolated as a off-white solid: HRES(+) m/e calcd for $C_{23}H_{21}N_3O_3S$ (M+H)$^+$420.1377, found 420.1378.

Example 32

5-[4-(2-Dimethylamino-ethoxy)-quinolin-6-ylmeth-(Z)-ylidine]-2-[2-(3-fluorophenyl)-ethylamino]-thiazol-4-one

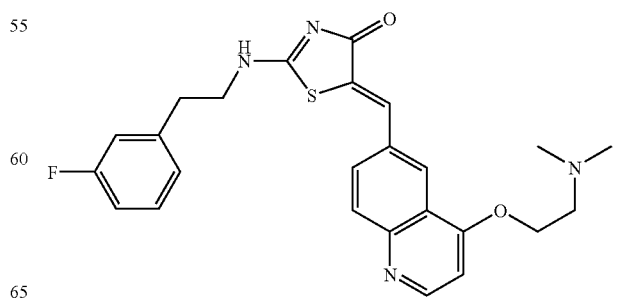

a) Preparation of 4-(2-dimethylamino-ethoxy)-quinoline-6-carbaldehyde

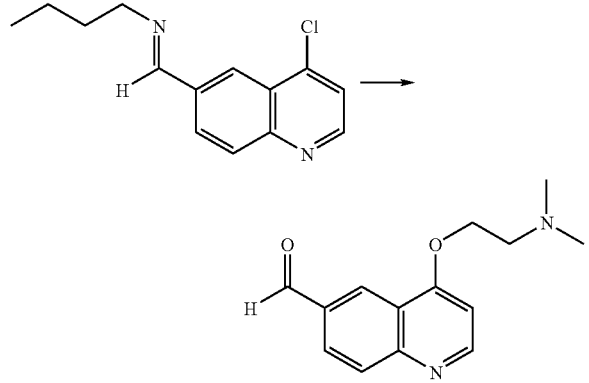

To a solution of 2-dimethyamino-ethanol (500 mg, 5.61 mmol) in DMF (N,N-dimethylformamide) (30 mL) was added sodium hydride (161.5 mg, 6.73 mmol, 1.2 equiv.) at 0° C. and stirred for 15 min at this temperature. Then, a solution of butyl (4-chloroquinolin-6-ylmethylene)-amine (preparation was described in example 27b) (553.6 mg, 2.24 mmol) in DMF (5 mL) was added at 0° C. After addition, the reaction mixture was allowed to warm to room temperature and stirred for 15 h. Then, the mixture was diluted with saturated ammonium chloride solution and the organic compound was extracted into ethyl acetate (3×50 mL). The combined extracts were washed with brine solution and dried over anhydrous magnesium sulfate. After filtration of the drying agent, the solvent was removed under the vacuum and the brown residue was dissolved in THF (4 mL) and 6 mL of HCl solution (3.0N) was added. The resulting solution was stirred for 3 h at room temperature. Then, it was neutralized with sodium bicarbonate solution and extracted with ethyl acetate (2×50 mL). The combined extracts were washed with brine solution and dried over anhydrous magnesium sulfate. After filtration of the drying agent, the solvent was removed under the vacuum and the brown residue was purified by using a Biotage silica gel column chromatography to obtain 155 mg (11.3% yield) of 4-(2-dimethylamino-ethoxy)-quinoline-6-carbaldehyde as a brown solid: EI-HRMS m/e calcd for $C_{14}H_{16}N_2O_2$ (M+) 244.1212, found 244.1213.

b) Preparation of 2-[(3-fluorophenyl)-ethylamino]-thiazol-4-one

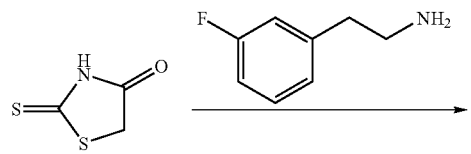

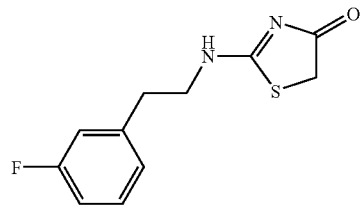

To a solution of (3-fluorophenyl)-ethylamine (3.06 g, 22 mmol) and rhodanine (2.66 g, 20 mmol) in acetonitrile (70 mL) was added DIEA (7.66 mL, 44 mmol) at room temperature. Then, this solution was cooled to 0° C. and mercuric chloride (5.97 g, 22 mmol) was added in two portions. After addition, the suspension was allowed to warm to room temperature and stirred for 3 days. The resulting black solids were filtered through a plug of celite and washed with dichloromethane (500 mL) and methanol (250 mL). The combined solvents were removed under the vacuum and the crude residue was dissolved in ethyl acetate (25 mL) at hot condition and stored in the refrigerator overnight. Then, the solids were collected by filtration and washed with ethyl acetate. After drying in air, 3.65 g (76.6% yield) of 2-[(3-fluorophenyl)-ethylamino]-thiazol-4-one was isolated as a white amorphous solid: HRES(+) m/e calcd for $C_{11}H_{11}FN_2OS$ (M+H)+ 239.0649, found 239.0647.

c) Preparation of 5-[4-(2-dimethylamino-ethoxy)-quinolin-6-ylmeth-(Z)-ylidine]-2-[2-(3-fluorophenyl)-ethylamino]-thiazol-4-one

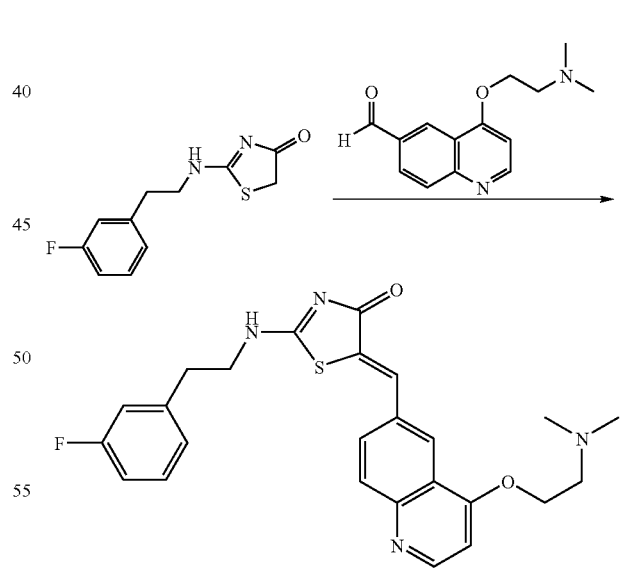

To a suspension of 2-[(3-fluorophenyl)-ethylamino]-thiazol-4-one (43.7 mg, 0.18 mmol) and 4-(2-dimethylamino-ethoxy)-quinoline-6-carbaldehyde (49.2 mg, 0.20 mmol) in toluene (0.6 mL) in a microwave tube were added benzoic acid (2.24 mg, 0.018 mmol) and piperidine (1.85 uL, 0.018 mmol) at room temperature. The microwave tube was sealed and heated to 150° C. in a closed microwave for 30 min. Then, the mixture was cooled to room temperature and diluted with toluene. The solids were collected by filtration and washed with acetonitrile. After drying in air, 38 mg (44.6% yield) of 5-[4-(2-dimethylamino-ethoxy)-quinolin-6-ylmeth-(Z)-ylidine]-2-[2-(3-fluorophenyl)-ethylamino]-thiazol-4-one was isolated as an yellow solid: HRES(+) m/e calcd for $C_{25}H_{25}FN_4O_2S$ $(M+H)^+ 465.1755$, found 465.1746.

Example 33

2-[2-(3-Fluorophenyl)-ethylamino]-5-[4-(2,2,2-trifluoro-ethoxy)-quinolin-6-ylmeth-(Z)-ylidine]-thiazol-4-one

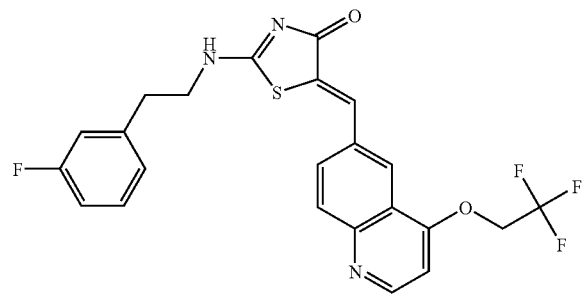

a) Preparation of 4-(2,2,2-trifluoro-ethoxy)-quinoline-6-carbaldehyde

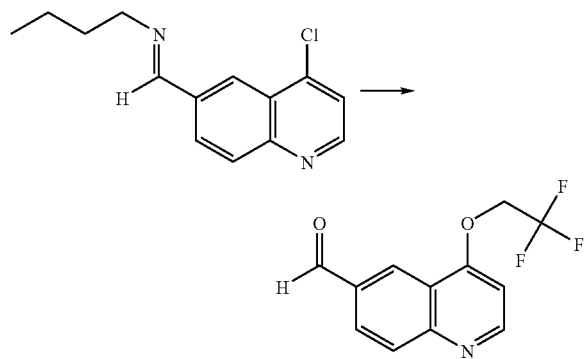

To a solution of 2,2,2-trifluoro-ethanol (250 mg, 2.47 mmol) in DMF (15 mL) was added sodium hydride (71.25 mg, 2.97 mmol, 1.2 equiv.) at 0° C. and stirred for 15 min at this temperature. Then, a solution of butyl (4-chloroquinolin-6-ylmethylene)-amine (preparation was described in example 27b) (244.2 mg, 0.99 mmol) in DMF (1.79 mL) was added at 0° C. After addition, the reaction mixture was allowed to warm to room temperature and stirred for 4 h. Then, the mixture was diluted with saturated ammonium chloride solution and the organic compound was extracted into ethyl acetate (3×50 mL). The combined extracts were washed with brine solution and dried over anhydrous magnesium sulfate. After filtration of the drying agent, the solvent was removed under the vacuum and the brown residue was dissolved in THF (5 mL) and 3 mL of HCl solution (3.0N) was added. The resulting solution was stirred for 4 h at room temperature. Then, it was neutralized with sodium bicarbonate solution to from suspension. The solids were collected by filtration and washed with water. After drying in air, 190 mg (30% yield) of 4-(2,2,2-trifluoro-ethoxy)-quinoline-6-carbaldehyde was isolated as a white solid: EI-HRMS m/e calcd for $C_{12}H_8F_3N_2O_2$ (M+) 255.0507, found 255.0505.

b) Preparation of 5-[4-(2,2,2-trifluoro-ethoxy)-quinolin-6-ylmeth-(Z)-ylidine]-2-[2-(3-fluorophenyl)-ethylamino]-thiazol-4-one

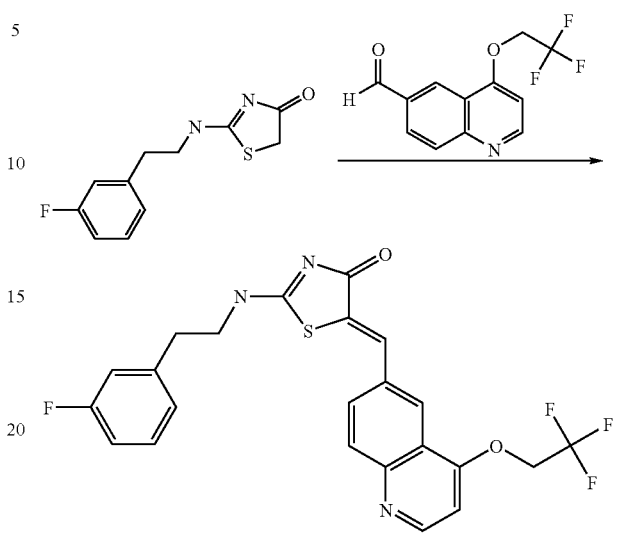

To a suspension of 2-[(3-fluorophenyl)-ethylamino]-thiazol-4-one (preparation was described in example 33b) (80 mg, 0.336 mmol) and 4-(2,2,2-trifluoro-ethoxy)-quinoline-6-carbaldehyde (94.32 mg, 0.37 mmol) in toluene (2 mL) in a microwave tube were added benzoic acid (4.12 mg, 0.033 mmol) and piperidine (3.39 uL, 0.034 mmol) at room temperature. The microwave tube was sealed and heated to 150° C. in a closed microwave for 30 min. Then, the mixture was cooled to room temperature and diluted with toluene. The solids were collected by filtration and washed with acetonitrile. After drying in air, 85 mg (53.2% yield) of 5-[4-(2,2,2-trifluoro-ethoxy)-quinolin-6-ylmeth-(Z)-ylidine]-2-[2-(3-fluorophenyl)-ethylamino]-thiazol-4-one was isolated as an yellow solid: HRES(+) m/e calcd for $C_{23}H_{17}F_3N_3O_2S$ $(M+H)^+ 476.1051$, found 476.1052.

Example 34

2-Amino-5-(4-ethylsulfanyl-quinolin-6-ylmeth-(Z)-ylidine)-thiazol-4-one

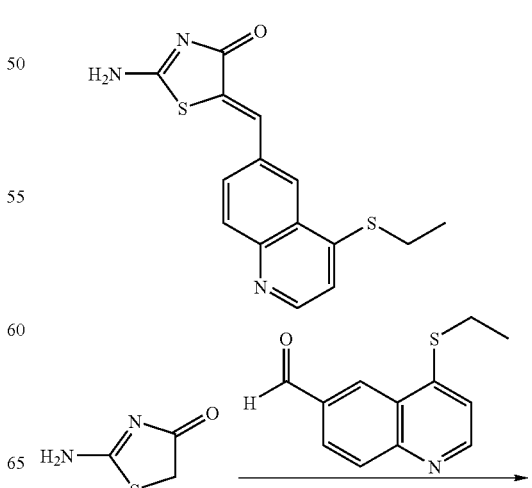

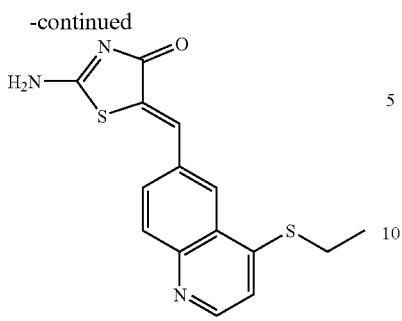

To a suspension of pseudothiohydantoin (81 mg, 0.70 mmol), 4-ethylsulfanyl-quinoline-6-carbaldehyde (example 36b, 152 mg, 0.70 mmol) and sodium acetate (164 mg, 2 mmol) in xylenes (5 mL) was added acetic acid (150 uL) at room temperature. Then, the mixture was refluxed for 15 h at this time lot of solids were formed. The mixture was cooled to room temperature and it was diluted with xylenes and acetonitrile. The solids were collected by filtration and washed with acetonitrile. Then, the solids were again dissolved in DMF at hot condition and diluted with water. This was neutralized with saturated potassium carbonate solution. Then, the resulting solids were collected by filtration and washed with water. After drying in air, 165 mg (75% yield) of 2-amino-5-(4-ethylsulfanyl-quinolin-6-ylmeth-(Z)-ylidine)-thiazol-4-one was isolated as a brown solid: HRES(+) m/e calcd for $C_{15}H_{13}N_3OS_2$ $(M+H)^+$ 316.0573, found 316.0573.

Example 35

5-(4-Ethylsulfanyl-quinolin-6-ylmeth-(Z)-ylidine)-2-((1R,2S)-2-phenyl-cyclopropylamino)-thiazol-4-one

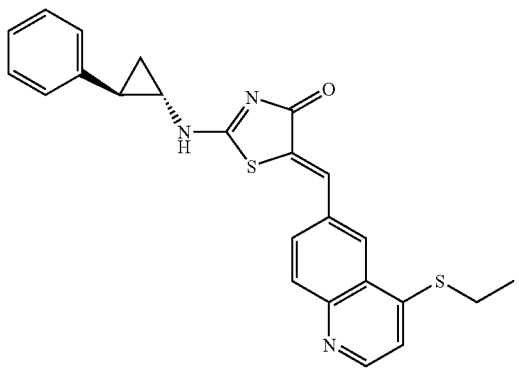

a) Preparation of 6-bromo-4-ethylsulfanyl-quinoline

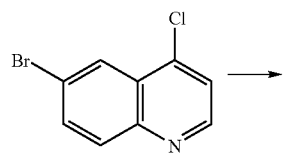

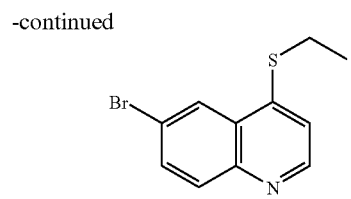

To a solution of 6-bromo-4-chloro-quinoline (1.5 g, 6.18 mmol) in DMF (60 mL) was added sodium thioethoxide (624 mg, 7.42 mmol) at 0° C. After addition, it was turned to a dark green solution which then turned to a yellow cloudy solution after 15 h at room temperature. Then, the mixture was diluted with water and extracted with ethyl acetate (3×50 mL). The combined extracts were washed with brine solution and dried over anhydrous magnesium sulfate. After filtration of the drying agent, the filtrate was removed under the vacuum and the residue was purified by using a Biotage silica gel column chromatography to afford 1.48 g (89.6% yield) of 6-bromo-4-ethylsulfanyl-quinoline as an yellow solid: EI-HRMS m/e calcd for $C_{11}H_{10}BrNS$ (M+) 266.9717, found 266.9715.

b) Preparation of 4-ethylsulfanyl-quinoline-6-carbaldehyde

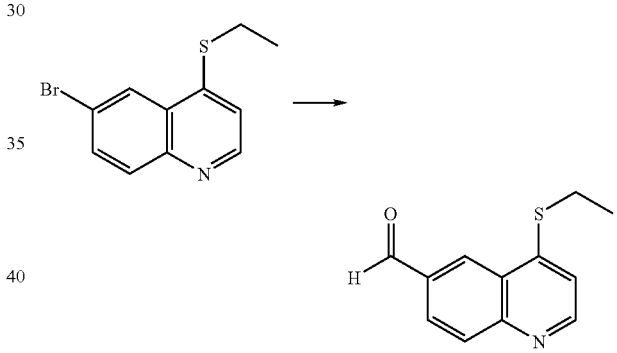

To a solution of 6-bromo-4-ethylsulfanyl-quinoline (1.48 g, 5.5 mmol) in THF (60 mL) was added dropwise a 2.5M solution of n-butyllithium in hexanes (2.42 mL, 6.07 mmol, 1.1 equiv.) at −70° C. During the addition, the color of the solution was turned into a dark brown and this solution was stirred for 1 h at this temperature. Then, a solution of dimethylformamide (0.848 mL, 11 mmol) in THF (5 mL) was added dropwise. After addition, the mixture was allowed to warm to room temperature and stirred for 2 h. Then, the mixture was diluted with saturated ammonium chloride solution and the two layers were separated. The aqueous layer was extracted with ethyl acetate (3×100 mL). The combined organic extracts were washed with brine solution and dried over anhydrous magnesium sulfate. Filtration of the drying agent and removal of the solvent under the vacuum gave the yellow solid which was dissolved in ethyl acetate (~10 mL) at hot condition and diluted with hexanes (~20 mL). After cooling in the refrigerator overnight, the solids were collected by filtration and washed with 10% ethyl acetate in hexanes. After drying in air, 0.614 g (51% yield) of 4-ethylsulfanyl-quinoline-6-carbaldehyde was isolated as a yellow solid: EI-HRMS m/e calcd for $C_{12}H_{11}NOS$ $(M^+)$ 217.0561, found 217.0554.

c) Preparation of 5-(4-ethylsulfanyl-quinolin-6-yl-meth-(Z)-ylidine)-2-((1R,2S)-2-phenyl-cyclopropylamino)-thiazol-4-one a) Preparation of 5-(4-ethylsulfanyl-quinolin-6-yl-meth-(Z)-ylidine)-2-[2-(3-fluoro-phenyl)-ethylamino]-thiazol-4-one

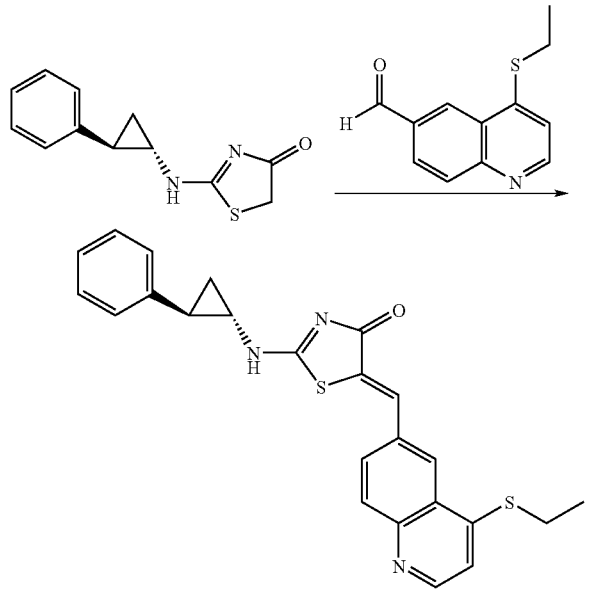

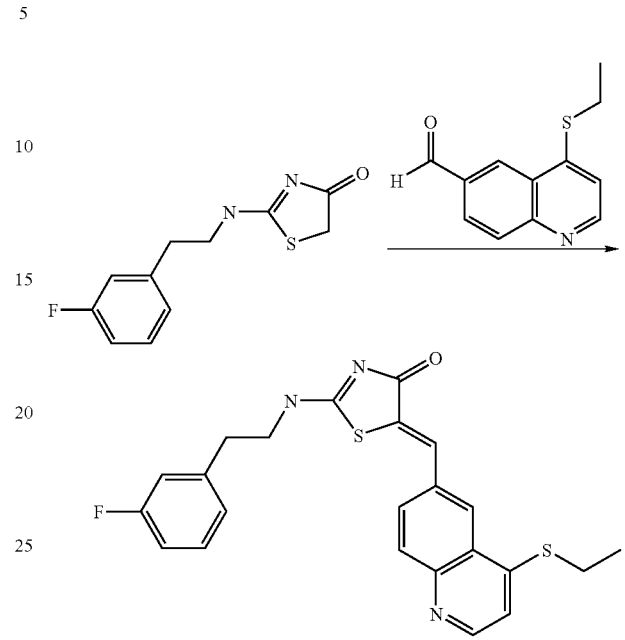

To a suspension of 2-((1R,2S)-2-phenyl-cyclopropylamino)-thiazol-4-one (preparation described in example 2a) (120 mg, 0.52 mmol) and 4-ethylsulfanyl-quinoline-6-carbaldehyde (120 mg, 0.55 mmol) in toluene (4 mL) in a microwave tube were added benzoic acid (7.0 mg, 0.055 mmol) and piperidine (5.5 uL, 0.055 mmol) at room temperature. The microwave tube was sealed and heated to 150° C. in a closed microwave for 30 min. Then, the mixture was cooled to room temperature and diluted with toluene and acetonitrile. After a brief heating and cooling, the solids were collected by filtration and washed with acetonitrile. After drying in air, 90 mg (40% yield) of 5-(4-ethylsulfanyl-quinolin-6-ylmeth-(Z)-ylidine)-2-((1R,2S)-2-phenyl-cyclopropylamino)-thiazol-4-one was isolated as an yellow solid: HRES(+) m/e calcd for $C_{24}H_{21}N_3OS_2$ (M+H)$^+$432.1199, found 432.1197.

To a suspension of 2-[(3-fluorophenyl)-ethylamino]-thiazol-4-one (example 31b, 125 mg, 0.52 mmol) and 4-ethylsulfanyl-quinoline-6-carbaldehyde (example 35b, 120 mg, 0.55 mmol) in toluene (4 mL) in a microwave tube were added benzoic acid (7 mg, 0.055 mmol) and piperidine (5.5 uL, 0.055 mmol) at room temperature. The microwave tube was sealed and heated to 150° C. in a closed microwave for 30 min. Then, the mixture was cooled to room temperature and diluted with acetonitrile. The solids were collected by filtration and washed with acetonitrile. After drying in air, 50 mg (22% yield) of 5-(4-ethylsulfanyl-quinolin-6-ylmeth-(Z)-ylidine)-2-[2-(3-fluorophenyl)-ethylamino]-thiazol-4-one was isolated as an yellow solid: HRES(+) m/e calcd for $C_{23}H_{20}FN_3OS_2$ (M+H)$^+$438.1105, found 438.1105.

Example 36

5-(4-Ethylsulfanyl-quinolin-6-ylmeth-(Z)-ylidine)-2-[2-(3-fluorophenyl)-ethylamino]-thiazol-4-one

Example 37

2-Amino-5-{4-[2-(4-fluorophenyl)-ethoxy]-quinolin-6-ylmeth-(Z)-ylidine}-thiazol-4-one

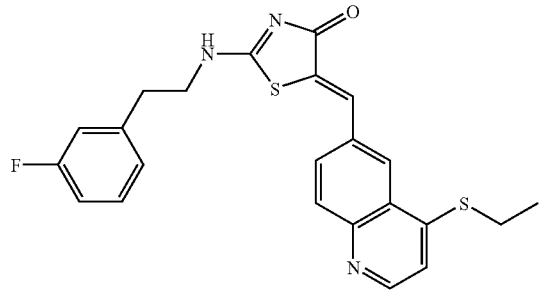

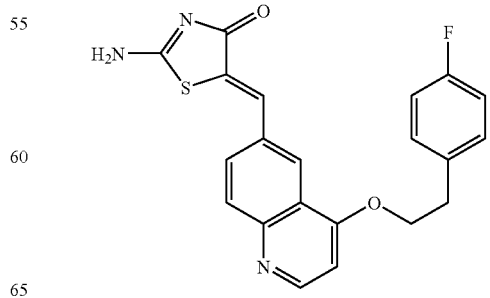

a) Preparation of 4-[2-(4-fluorophenyl)-ethoxy]-quinoline-6-carbaldehyde

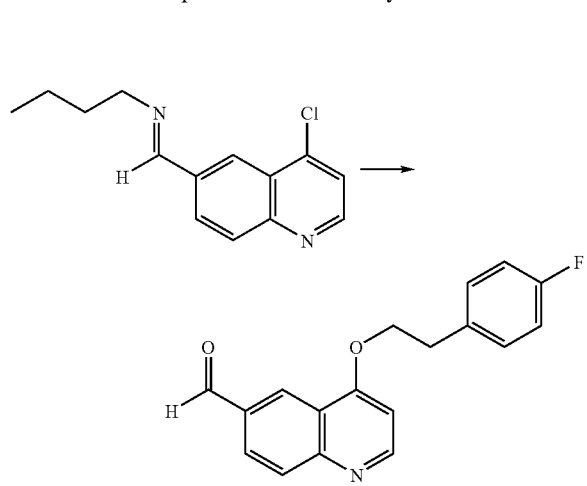

To a solution of 2-(4-fluorophenyl)-ethanol (350 mg, 2.42 mmol) in DMF (15 mL) was added sodium hydride (69.75 mg, 2.91 mmol) at 0° C. and stirred for 15 min at this temperature. Then, a solution of butyl (4-chloroquinolin-6-ylmethylene)-amine (preparation was described in example 27b) (239 mg, 0.97 mmol) in DMF (2.5 mL) was added at 0° C. After addition, the reaction mixture was allowed to warm to room temperature and stirred for 15 h. Then, the mixture was diluted with saturated ammonium chloride solution and the organic compound was extracted into ethyl acetate (3×50 mL). The combined extracts were washed with brine solution and dried over anhydrous magnesium sulfate. After filtration of the drying agent, the solvent was removed under the vacuum and the oily residue was dissolved in THF (5 mL) and 3 mL of HCl solution (3.0N) was added. The resulting solution was stirred for 4 h at room temperature. Then, it was neutralized with saturated sodium bicarbonate solution and the organic compound was extracted into ethyl acetate (3×50 mL). The combined extracts were washed with brine solution and dried over anhydrous magnesium sulfate. After filtration of the drying agent, the solvent was removed under the vacuum and the residue was purified by using a Biotage silica gel column chromatography to obtain 85 mg (11.9% yield) of 4-[2-(4-fluorophenyl)-ethoxy]-quinoline-6-carbaldehyde as a light yellow solid: EI-HRMS m/e calcd for $C_{18}H_{14}FNO_2$ (M$^+$) 295.1009, found 295.1010.

b) Preparation of 2-amino-5-{4-[2-(4-fluorophenyl)-ethoxy]-quinolin-6-ylmeth-(Z)-ylidine}-thiazol-4-one

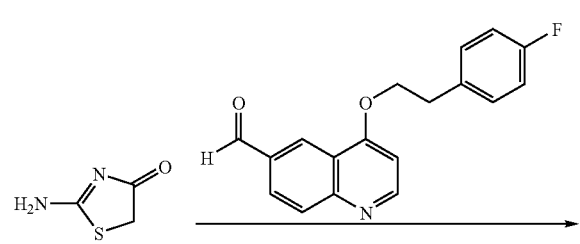

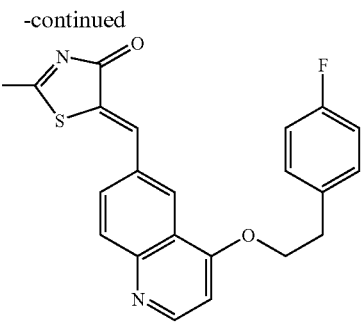

To a suspension of pseudothiohydantoin (31 mg, 0.26 mmol), 4-[2-(4-fluorophenyl)-ethoxy]-quinoline-6-carbaldehyde (78.85 mg, 0.26 mmol) and sodium acetate (65.71 mg, 0.801 mmol) in xylenes (5 mL) was added acetic acid (85 uL) at room temperature. Then, the mixture was refluxed for 15 h at this time lot of brown suspension was formed. The mixture was cooled to room temperature and it was diluted with xylenes and acetonitrile. The solids were collected by filtration and washed with acetonitrile. Then, the solids were dissolved in THF and neutralized with saturated sodium carbonate solution. The resulting solids were collected by filtration and washed with water. After drying in air, 40 mg (38.1% yield) of 2-amino-5-{4-[2-(4-fluorophenyl)-ethoxy]-quinolin-6-ylmeth-(Z)-ylidine}-thiazol-4-one was isolated as a light brown solid: HRES(+) m/e calcd for $C_{21}H_{16}FN_3O_2S$ (M+H)$^+$394.1020, found 394.1022.

Example 38

2-Amino-5-{4-[2-(3-methoxyphenyl)-ethoxy]-quinolin-6-ylmeth-(Z)-ylidine}-thiazol-4-one

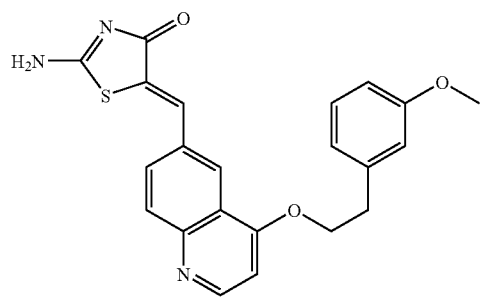

a) Preparation of 4-[2-(3-methoxyphenyl)-ethoxy]-quinoline-6-carbaldehyde

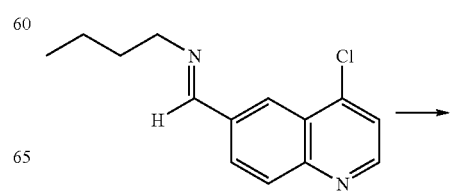

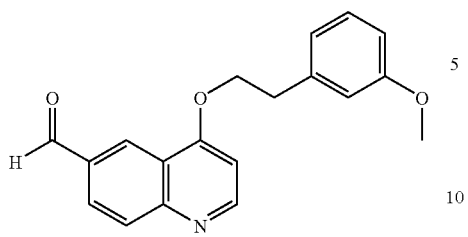

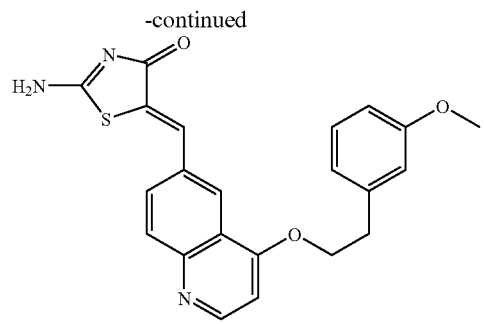

To a solution of 2-(3-methoxyphenyl)-ethanol (359 mg, 2.36 mmol) in DMF (13 mL) was added sodium hydride (62.3 mg, 2.59 mmol) at 0° C. and stirred for 15 min at this temperature. Then, a solution of butyl (4-chloroquinolin-6-ylmethylene)-amine (preparation was described in example 27b) (300 mg, 1.18 mmol) in DMF (3 mL) was added at 0° C. After addition, the reaction mixture was allowed to warm to room temperature and stirred for 30 min. During this period, the color of the solution was changed from white to black and then to brown. Then, the reaction mixture was heated to 60° C. and stirred for 15 h. After cooling to room temperature, the mixture was diluted with saturated ammonium chloride solution and the organic compound was extracted into ethyl acetate (3×50 mL). The combined extracts were washed with brine solution and dried over anhydrous magnesium sulfate. After filtration of the drying agent, the solvent was removed under the vacuum and the oily residue was dissolved in THF (3 mL) and 3 mL of HCl solution (3.0N) was added. The resulting solution was stirred for 2 h at room temperature. Then, it was neutralized with saturated sodium bicarbonate solution and the organic compound was extracted into ethyl acetate (3×50 mL). The combined extracts were washed with brine solution and dried over anhydrous magnesium sulfate. After filtration of the drying agent, the solvent was removed under the vacuum and the residue was purified by using a Biotage silica gel column chromatography to obtain 133 mg (36.7% yield) of 4-[2-(3-methoxyphenyl)-ethoxy]-quinoline-6-carbaldehyde as a light yellow solid: EI-HRMS m/e calcd for $C_{19}H_{17}NO_3$ (M+) 307.1208, found 307.1204.

b) Preparation of 2-amino-5-{4-[2-(3-methoxyphenyl)-ethoxy]-quinolin-6-ylmeth-(Z)-ylidine}-thiazol-4-one

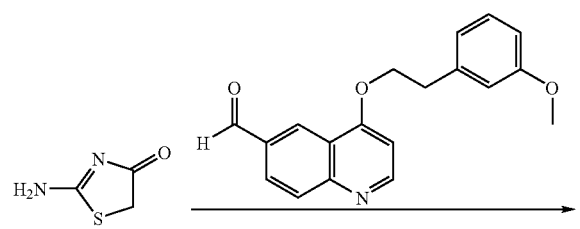

To a suspension of pseudothiohydantoin (28 mg, 0.24 mmol), 4-[2-(3-methoxyphenyl)-ethoxy]-quinoline-6-carbaldehyde (74.07 mg, 0.24 mmol) and sodium acetate (79.08 mg, 0.964) in xylenes (5 mL) was added acetic acid (2 mL) at room temperature. Then, the mixture was refluxed for 15 h at this time lot of brown suspension was formed. The mixture was cooled to room temperature and it was diluted with xylenes and acetonitrile. The solids were collected by filtration and washed with acetonitrile. Then, the solids were dissolved in THF and neutralized with saturated sodium carbonate solution. The resulting solids were collected by filtration and washed with water. After drying in air, 42 mg (43% yield) of 2-amino-5-{4-[2-(3-methoxyphenyl)-ethoxy]-quinolin-6-ylmeth-(Z)-ylidine}-thiazol-4-one was isolated as a light brown solid: HRES(+) m/e calcd for $C_{22}H_{19}N_3O_3S$ (M+H)+ 406.1220, found 406.1222.

Example 39

2-[2-Amino-5-[4-(2,2,2-trifluoro-ethoxy)-quinolin-6-ylmeth-(Z)-ylidine]-thiazol-4-one

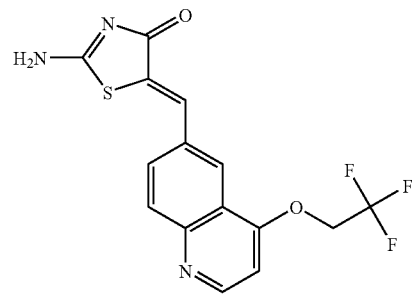

a) Preparation of 2-amino-5-[4-(2,2,2-trifluoro-ethoxy)-quinolin-6-ylmeth-(Z)-ylidine]-thiazol-4-one

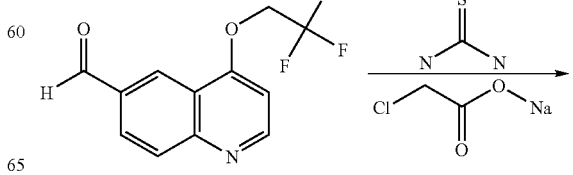

-continued

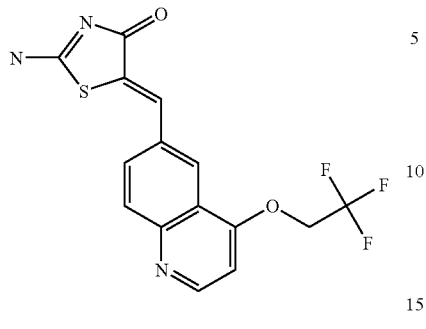

A mixture of 4-(2,2,2-trifluoro-ethoxy)-quinoline-6-carbaldehyde (72.99 mg, 0.28 mmol), thiourea (40 mg, 0.52 mmol) and sodium 2-chloroacetate (61.18 mg, 0.52 mmol) in acetic acid (1 mL) was placed in a microwave tube and the microwave tube was sealed and heated to 150° C. in a closed microwave for 30 min. Then, the mixture was cooled to room temperature and diluted with dichloromethane and saturated sodium bicarbonate solution to afford a suspension. The solids were collected by filtration and washed with acetonitrile. This solid was treated with methanol and THF and the suspension was heated with heat gun. After cooling to room temperature, the solids were collected by filtration and washed with methanol. Then, the filtrate was concentrated under the vacuum and the residue was suspended in acetonitrile and heated with heat gun. After cooing to room temperature, the solids were collected by filtration and washed with acetonitrile. After drying in air, 15 mg (8.16% yield) of 2-amino-5-[4-(2,2,2-trifluoro-ethoxy)-quinolin-6-ylmeth-(Z)-ylidine]-thiazol-4-one was isolated as an yellow solid: HRES(+) m/e calcd for $C_{15}H_{10}F_3N_3O_2S$ (M+H)$^+$ 354.0519, found 354.0517.

Example 40

4-Ethoxy-6-[2-[2-(3-fluoro-phenyl)-ethylamino]-4-oxo-4H-thiazol-(5Z)-ylidenemethyl]-quinoline-3-carbonitrile

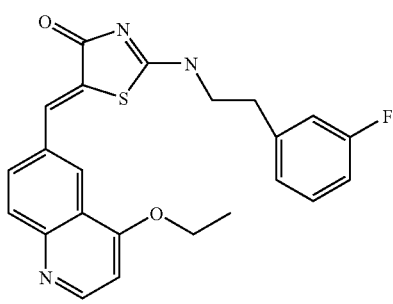

a) Preparation of 5-(4-ethoxy-quinolin-6-ylmethylene)-2-thioxo-thiazolidin-4-one

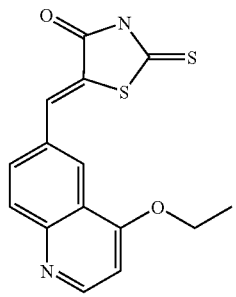

The suspension of 4-ethoxy-quinoline-6-carbaldehyde (example 3b) (4.0 g, 20 mmol) and rhodanine (2.65 g, 20 mmol) in acetic acid (40 mL) was stirred under reflux for 12 h. After cooling to room temperature, water (50 mL) was added. The solid was collected by filtration, washed with water and dried to obtain 5-[1-quinolin-6-yl-meth-(Z)-ylidene]-2-thioxo-thiazolidin-4-one (6.3 g, 100%) as a brown solid. LC-MS m/e 317 (MH$^+$).

b) Preparation of 5-(4-ethoxy-quinolin-6-ylmethylene)-2-methylsulfanyl-thiazol-4-one

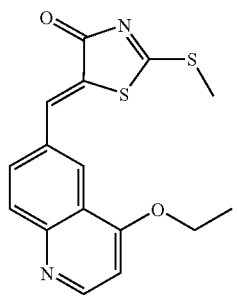

To the suspension of 5-[1-quinolin-6-yl-meth-(Z)-ylidene]-2-thioxo-thiazolidin-4-one (example 40a) (2.4 g, 20 mmol), iodomethane (2.54 mL, 40 mmol) and DIEA (N,N-diisopropylethylamine) (6.4 mL, 30 mmol) in anhydrous ethanol (70 mL) was stirred at room temperature for 24 h. After adding water (50 mL), the solid was collected by filtration, washed with water and dried to give 5-(4-ethoxy-quinolin-6-ylmethylene)-2-methylsulfanyl-thiazol-4-one (5.67 g, 84%) as a yellow solid. LC-MS m/e 331 (MH$^+$)

c) Preparation of 5-(4-ethoxy-quinolin-6-ylmethylene)-2-[2-(3-fluoro-phenyl)-ethylamino]-thiazol-4-one The suspension of 5-(4-ethoxy-quinolin-6-ylmethylene)-2-methylsulfanyl-thiazol-4-one (example 40b) (100 mg, 0.3 mmol), m-fluorophenylethylamine (80 ul, 0.6 mmol) and DIEA (0.10 mL, 0.6 mmol) in acetoniltile (2 mL) was stirred under at 80° C. for 3 h. After cooling to room temperature, the solid was collected by filtration, washed with a little bit of acetonitrile and dried. Flash chromatography (Merck Silica gel 60, 230-400 mesh, 0%-5% methanol in methylene chloride in 30 min) afforded 5-(4-ethoxy-quinolin-6-ylmethylene)-2-[2-(3-fluoro-phenyl)-ethylamino]-thiazol-4-one (90 mg, 70%) as a light yellow solid: LC-MS m/e 422 (MH+).

Example 41

2-[2-(2-Ethoxy-phenyl)-ethylamino]-5-[1-(4-ethoxy-quinolin-6-yl)-meth-(Z)-ylidene]-thiazol-4-one

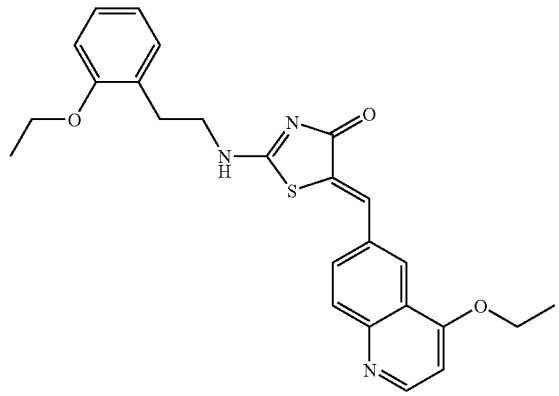

Similar procedure as described in example 40c was used, starting from 5-(4-ethoxy-quinolin-6-ylmethylene)-2-methylsulfanyl-thiazol-4-one (example 40b), 2-(2-ethoxy-phenyl)-ethylamine and DIEA to give 2-[2-(2-ethoxy-phenyl)-ethylamino]-5-[1-(4-ethoxy-quinolin-6-yl)-meth-(Z)-ylidene]-thiazol-4-one. LC-MS m/e 448 (MH+).

Example 42

2-[2-(2-Ethoxy-phenyl)-ethylamino]-5-[1-(4-ethoxy-quinolin-6-yl)-meth-(Z)-ylidene]-thiazol-4-one; compound with methanesulfonic acid

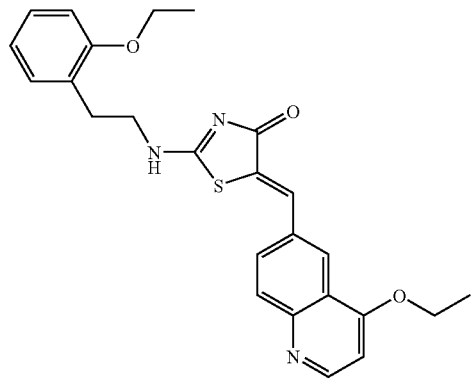

To the suspension of 2-[2-(2-Ethoxy-phenyl)-ethylamino]-5-[1-(4-ethoxy-quinolin-6-yl)-meth-(Z)-ylidene]-thiazol-4-one (60 mg, 0.13 mmol) in ethanol (2 mL) was added methanesulfonic acid (9.6 uL, 0.14 mmol) in ethanol (1 mL). After stirring for 30 min, t-butyl methyl ether (5 mL) was added slowly. The mixture was stirred for 3 hours. The solid was collected by filtration and washed with t-butyl methyl ether and dried to give 2-[2-(2-Ethoxy-phenyl)-ethylamino]-5-[1-(4-ethoxy-quinolin-6-yl)-meth-(Z)-ylidene]-thiazol-4-one; compound with methanesulfonic acid as light yellow solid (66 mg, 91%). LC-MS m/e 448 (MH+).

Example 43

2-(2,2-Difluoro-2-pyridin-2-yl-ethylamino)-5-[1-(4-ethoxy-quinolin-6-yl)-meth-(Z)-ylidene]-thiazol-4-one

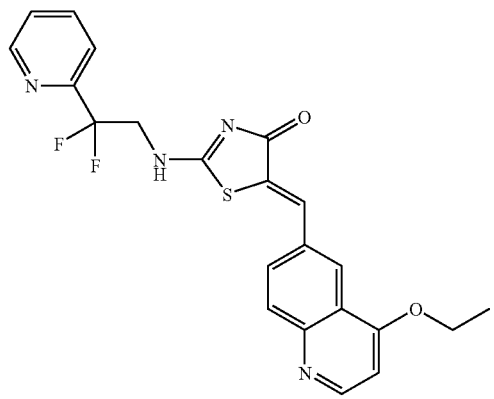

Similar procedure as described in example 40c was used, starting from 5-(4-y-quinolin-6-ylmethylene)-2-methylsulfanyl-thiazol-4-one (example 40b), 2,2-oro-2-pyridin-2-yl-ethylamine and DIEA to give 2-(2,2-Difluoro-2-pyridin-2-yl-amino)-5-[1-(4-ethoxy-quinolin-6-yl)-meth-(Z)-ylidene]-thiazol-4-one. LC-MS m/e (MH+).

Example 44

2-(2,2-Difluoro-2-pyridin-2-yl-ethylamino)-5-[1-(4-ethoxy-quinolin-6-yl)-meth-(Z)-ylidene]-thiazol-4-one; compound with methanesulfonic acid

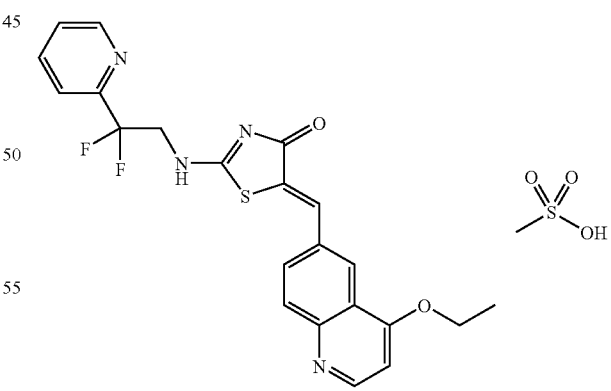

Similar procedure as described in example 42 was used, starting from 2-(2,2-difluoro-2-pyridin-2-yl-ethylamino)-5-[1-(4-ethoxy-quinolin-6-yl)-meth-(Z)-ylidene]-thiazol-4-one (example 43) and methanesulfonic acid to give 2-(2,2-difluoro-2-pyridin-2-yl-ethylamino)-5-[1-(4-ethoxy-quinolin-6-yl)-meth-(Z)-ylidene]-thiazol-4-one; compound with methanesulfonic acid. LC-MS m/e 441 (MH+).

Example 45

2-Amino-5-[1-(4-ethoxy-quinolin-6-yl)-meth-(Z)-ylidene]-thiazol-4-one

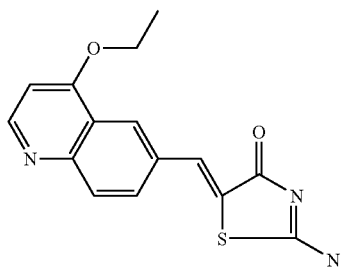

Similar procedure as described in example 34 was used, starting with 4-ethoxy-quinoline-6-carbaldehyde (example 3b), 2-amino-thiazol-4-one, sodium acetate and acetic acid to give 2-Amino-5-[1-(4-ethoxy-quinolin-6-yl)-meth-(Z)-ylidene]-thiazol-4-one. LC-MS m/e 300 (MH$^+$).

Example 46

5-[1-(4-Ethoxy-quinolin-6-y)-meth-(Z)-ylidene]-2-[2-(4-fluoro-phenyl)-cyclopropylamino]-thiazol-4-one

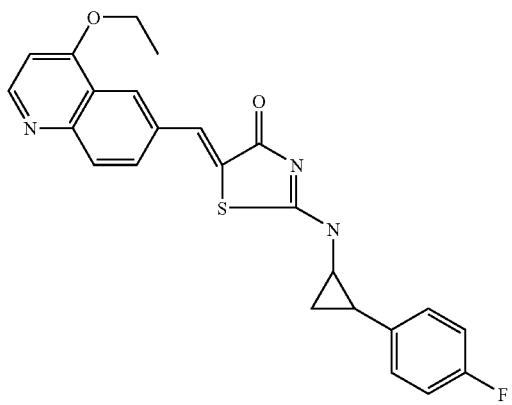

a) Preparation of 2-(4-fluoro-phenyl)-cyclopropanecarboxylic acid ethyl ester

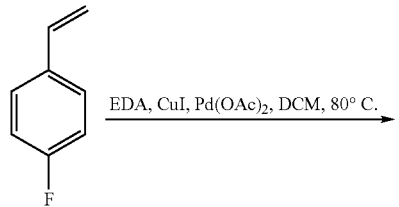

EDA, CuI, Pd(OAc)$_2$, DCM, 80° C.

-continued

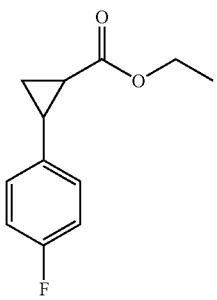

In an oven-dried two-neck round flask equipped with condenser and Argon inlet was charged with 40 mL of newly opened anhydrous chloroform. Dry Argon gas was bubbled through the chloroform. copper (I) iodide (38 mg, 1 mol %) and palladium (II) acetate (45 mg, 1 mol %) were added to the Chloroform and stirred at room temperature for 15 minutes under argon. Then 4-fluorostyrene (2.4 mL, 20 mmol) in 20 mL of dry chloroform was added to the above solution. Finally ethyl diazoacetate (8.3 mL, 80 mmol) in 10 mL of chloroform was added dropwise to the reaction mixture over 2 hour. The reaction mixture was heated at 80° C. for overnight. The reaction mixture was cooled down to room temperature and rotavaped to afford dark green oil. The residue was diluted with 200 mL of ethyl acetate and washed with saturated sodium bicarbonate aqueous solution (1×50 mL), water (1×50 mL) and brine (1×50 mL) respectively. The ethyl acetate layer was dried over Sodium sulfate and concentrated to give 5 gram of light brown oil as crude product, which was purified with flash chromatography (40 gram prepacked column by Isco, Inc., 230-400 mesh, eluants: 0-20% ethyl acetate in hexanes) to obtain 2.625 grams of the desired product as clear oil. The trans configuration of the structure was confirmed by NOE of $^1$H NMR, yield=62%.

b) Preparation of 2-(4-fluoro-phenyl)-cyclopropanecarboxylic acid

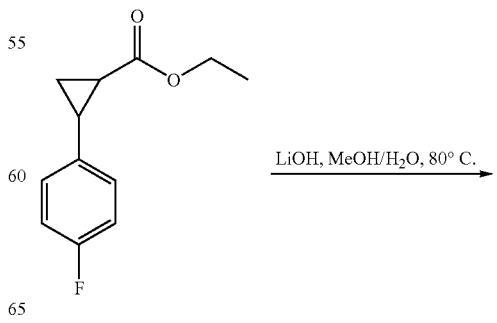

LiOH, MeOH/H$_2$O, 80° C.

-continued

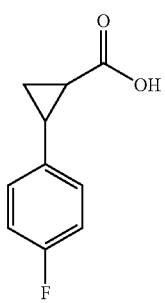

In a round flask was charged with 2-(4-fluoro-phenyl)-cyclopropanecarboxylic acid ethyl ester (1700 mg, 8.16 mmol), lithium monohydrate (1370 mg, 32.7 mmol), methanol (25 mL) and water (10 mL). The mixture was heated at 80° C. for 2 hours. The reaction mixture was rotavaped. The residue was neutralized with 4N hydrochloric acid and extracted with dichloromethane. The dichloromethane layer was washed with brine, dried over sodium sulfate and evaporated to give 1.61 grams of white solid as desired product. LC-MS m/e 179 (MH⁻).

c) Preparation of [2-(4-fluoro-phenyl)-cyclopropyl]-carbamic acid tert-butyl ester

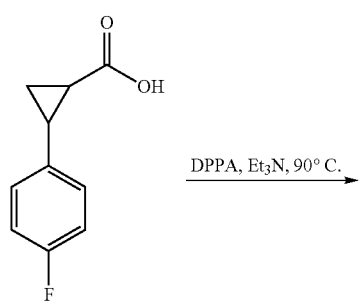

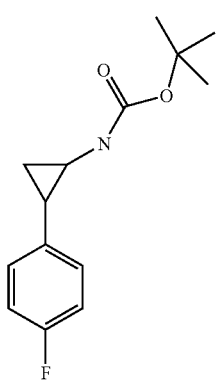

In a round flask equipped with condenser and argon inlet was charged with 2-(4-fluoro-phenyl)-cyclopropanecarboxylic acid (322 mg, 1.79 mmol) and tert-butanol (3000 mg). The mixture was warmed to 30° C. Diphenylphosphoryl azide (0.424 mL, 1.1 eq) was added dropwise to the above mixture. The reaction mixture was stirred at room temperature for 30 minutes and then was heated at 90° C. for overnight. The reaction mixture was concentrated by rotavaping. Sodium bicarbonate aqueous solution (15 mL, 10% w/v) was added to the above residue and stirred at room temperature for 0.5 hours. It was extracted with diethyl ether (3×50 mL) then. The ether layers were combined, dried over sodium sulfate and concentrated. The crude product was purified with flash chromatography (40 gram prepacked column by Isco, Inc., 230-400 mesh, eluant: 0-20% ethyl acetate in hexanes) to afford 364 mg of white solid as the desired product. Two peaks were observed with chiral HPLC (equal amounts but the opposite optical rotation). Yield=62%.

d) Preparation of 2-(4-fluoro-phenyl)-cyclopropylamine

In a round flask was added [2-(4-fluoro-phenyl)-cyclopropyl]-carbamic acid tert-butyl ester (350 mg) and 4N HCl in 1,4-dioxane (3 mL) for 2 hours. The reaction mixture was concentrated by rotavaping to obtain the crude product of 270 mg as white solid. LC-MS m/e 152 (MH⁺). The crude product was directly used for next step.

e) Preparation of 2-[2-(4-fluoro-phenyl)-cyclopropylamino]-thiazol-4-one

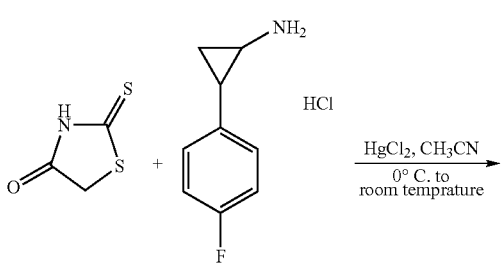

-continued

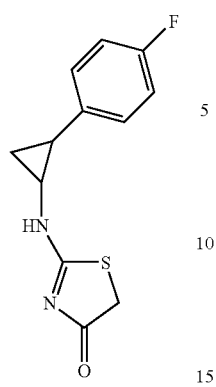

In a three-neck flask equipped with argon inlet was charged with rhodanine (200 mg, 1.5 mmol, 1.4 eq), anhydrous Acetonitrile (5 mL), 2-(4-fluoro-phenyl)-cyclopropylamine HCl salt (200 mg, 1.1 mmol, 1 eq) and diisopropylehtylamine (0.58 mL, 3 eq). The mixture was cooled to 0° C. and mercury (II) chloride (376 mg, 1.3 eq) was added. The reaction mixture was stirred at 0° C. for 30 minutes and room temperature for another 1.5 hours. The reaction mixture was filtered through a celite cake and washed with dichloromethane (3×20 mL), methanol (3×20 mL) and diethyl ether (3×20 mL). The filtrate and washing solutions were combined and concentrated by rotavaping to afford crude product. The crude was purified by flash chromatography (40 gram prepacked column by Isco, Inc., 230400 mesh, eluant: 0-10% methanol in dichloromethane) to obtain 136 mg of pure product. The structure was confirmed with $^1$H NMR, IR and HR-ES (+): 251. The chiral HPLC shows the pattern of two enantiomors. Yield=51% f) Preparation of 5-[1-(4-ethoxy-quinolin-6-yl)-meth-(Z)-ylidene]-2-[2-(4-fluoro-phenyl)-cyclopropylamio]-thiazol-4-one The similar procedure as described in example 35 was used, starting with 4-ethoxy-quinoline-6-carbaldehyde (example 3b), 2-[2-(4-fluoro-phenyl)-cyclopropylamino]-thiazol-4-one, sodium acetate and acetic acid to give 5-[1-(4-ethoxy-quinolin-6-yl)-meth-(Z)-ylidene]-2-[2-(4-fluoro-phenyl)-cyclopropylamino]-thiazol-4-one. LC-MS m/e 434.5 (MH$^+$).

Example 47

2-Amino-5-[1-[4-(piperidin-4-yloxy)-quinolin-6-yl]-meth-(Z)-ylidene]-thiazol-4-one

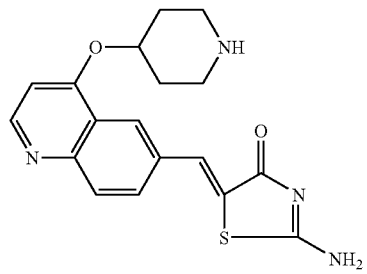

a) Preparation of 4-(6-iodo-quinolin-4-yloxy)-piperidine-1-carboxylic acid tert-butyl ester

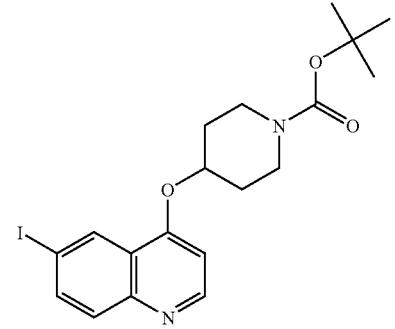

The mixture of 4-chloro-6-iodo-quinoline (217.5 mg, 1 mmol, prepared by similar procedure to example 1e), 4-hydroxy-piperidine-1-carboxylic acid tert-butyl ester (150 mg, 0.75 mmol), and 1-tert-butyl-2,2,4,4-pentakis(dimethylamino)-2λ$^5$, 4λ$^5$-catenadi(phosphazene) in tetrahdyrofuran (2M, 0.75 ml, 1.5 mmol) in acetonitrile (3.5 ml) was stirred at 100° C. for 30 min in microwave instrument (Personal Chemistry). After cooling the reaction, the solvent was evaporated, followed by addition of water, some of sodium carbonate saturated solution. The resulting solution was extracted with dimethylene chloride three times. The combined organic layer was dried over the brain, sodium sulfate, then evaporated to give a reddish gel. Flash chromatography (Merck silica gel 60, 230-400 mesh, 0%-3% methanol in dichloromethane for 30 min) afforded 4-(6-iodo-quinolin-4-yloxy)-piperidine-1-carboxylic acid tert-butyl ester (262.5 mg, 77%) as A light yellow solid. LC-MS m/e 455 (MH$^+$).

b) Preparation of 4-(6-formyl-quinolin-4-yloxy)-piperidine-1-carboxylic acid tert-butyl ester

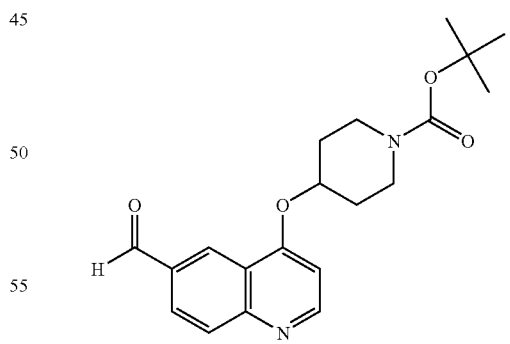

The similar procedure as described in Example 10b was used, starting from 4-(6-iodo-quinolin-4-yloxy)-piperidine-1-carboxylic acid tert-butyl ester (example 48a), diphenylpropyl phsophine, palladium acetate, triethyl amine, and trihexylsilane in anhydrous DMF (25 ml) was charged with carbon monoxide at 75 psi to give 4-(6-formyl-quinolin-4-yloxy)-piperidine-1-carboxylic acid tert-butyl ester. LC-MS m/e 357 (MH$^+$).

c) 4-{6-[2-Amino-4-oxo-4H-thiazol-(5Z)-ylidenemethyl]-quinolin-4-yloxy}-piperidine-1-carboxylic acid tert-butyl ester

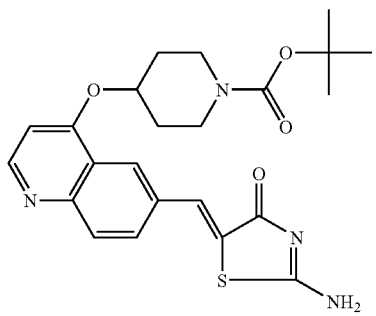

The similar procedure as described in example 35 was used, starting from 4-(6-formyl-quinolin-4-yloxy)-piperidine-1-carboxylic acid tert-butyl ester, 2-Amino-thiazol-4-one (example 48b), sodium acetate and acetic acid to obtain 4-{6-[2-amino-4-oxo-4H-thiazol-(5Z)-ylidenemethyl]-quinolin-4-yloxy}-piperidine-1-carboxylic acid tert-butyl ester as a yellow solid. Purification was performed with flash chromatography (Merck silica gel 60, 230-400 mesh, 1%-5% methanol in dichloromethane for 30 min. LC-MS m/e 455.5 (MH$^+$).

d) 2-Amino-5-[1-[4-(piperidin-4-yloxy)-quinolin-6-yl]-meth-(Z)-ylidene]-thiazol-4-one

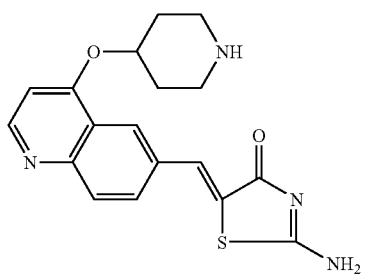

The suspension of 4-{6-[2-amino-4-oxo-4H-thiazol-(5Z)-ylidenemethyl]-quinolin-4-yloxy}-piperidine-1-carboxylic acid tert-butyl ester (70 mg, 0.15 mmol) in dichloromethane (1 ml) was treated with hydrogen chloride (in 1,4-dioxane, 4M, 1 ml) for 1.5 hr at room temperature. After removing the solvent, the obtained solid was treated with either. Ion exchange extraction chromatography (Cation exchanger: benenesulfonic acid, 2 g/6 ml, 1M ammonia in methanol and dichloromethane) afforded the free base form of 2-Amino-5-[1-[4-(piperidin-4-yloxy)-quinolin-6-yl]-meth-(Z)-ylidene]-thiazol-4-one. LC-MS m/e 355 (MH$^+$).

Example 48

5-[1-[4-(1-Acetyl-piperidin-4-yloxy)-quinolin-6-yl]-meth-(Z)-ylidene]-2-amino-thiazol-4-one

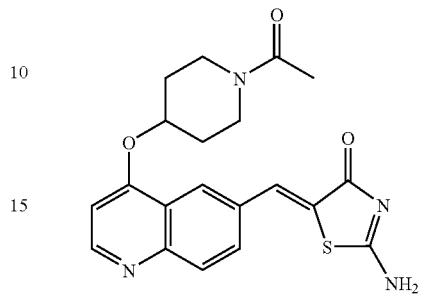

The suspension of 2-amino-5-[1-[4-(piperidin-4-yloxy)-quinolin-6-yl]-meth-(Z)-ylidene]-thiazol-4-one (223 mg, 0.63 mmol, example 48) and diisopropylethyl amine(1.4 ml, 7.9 mmol) in anhydrous dichloromethane and dimethyl formamide (1:1, 8 ml) was cooled to 0° C., followed by slow addition of acetyl chloride (54 mg, 0.69 mmol) in dichloromethane (0.5 ml). The resulting solution was then warmed up to room temperature for 1 hr. Both 5-[1-[4-(1-Acetyl-piperidin-4-yloxy)-quinolin-6-yl]-meth-(Z)-ylidene]-2-amino-thiazol-4-one and N-{5-[1-[4-(1-acetyl-piperidin-4-yloxy)-quinolin-6-yl]-meth-(Z)-ylidene]-4-oxo-4,5-dihydro-thiazol-2-yl}-acetamide were obtained. Then the solution was treated with sodium hydroxide (aq., 1N, 7 ml) at room temperature for overnight. After removing the solvents, a yellow solid was collected. HPLC (YMC C18, 2%-60% CH$_3$CN/H$_2$O in 20 min, float rate 20 ml/min) afforded 5-[1-[4-(1-acetyl-piperidin-4-yloxy)-quinolin-6-yl]-meth-(Z)-ylidene]-2-amino-thiazol-4-one (76 mg, 30%) as light yellow solid. LC-MS m/e 397 (MH$^+$).

Example 49

The pharmacological properties of the compounds of this invention may be confirmed by a number of pharmacological assays. The exemplified pharmacological assays which follow have been carried out with the compounds according to the invention and their salts. The compounds of the invention exhibited CDK1/Cyclin B activity with Ki values of less than 5.0 μM. This demonstrates that all of these compounds were active to inhibit CDK1/Cyclin B.

Kinase Assays

To determine inhibition of CDK1 activity, either Flash-Plate™ (NEN™-Life Science Products) assay or HTRF assay was performed. Both types of kinase assays were carried out using recombinant human CDK1/Cyclin B complex. GST-cyclinB (GST-cycB) and CDK1 cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. Cell 1993, 75, 805-816). A 6×-Histidine tagged truncated form of retinoblastoma (Rb) protein (amino acid 386-928) was used as the substrate for the CDK1/Cyclin B assay (the expression plasmid was provided by Dr. Veronica Sullivan, Department of Molecular Virology, Roche Research Centre, Welwyn Garden City, United Kingdom). The Rb protein is a natural substrate for phosphorylation by CDK1 (see Herwig and Strauss Eur. J. Biochem. Vol. 246 (1997) pp. 581-601 and the references cited therein). The expression of the 62 Kd protein was under the control of an IPTG inducible promoter in an M15 *E. coli* strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

For the FlashPlate kinase assay, 96-well FlashPlates were coated with Rb protein at 10 μg/ml, using 100 μl per well. Plates were incubated at 4° C. overnight or at room temperature for 3 hours on a shaker. To control for nonspecific phosphorylation, one row of wells was coated with 100 μl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 μl reaction mix (25 mM HEPES, 20 mM $MgCl_2$, 0.002% Tween 20, 2 mM DTT, 1 μM ATP, 4 nM $^{33}$P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times 1 - \frac{\text{test compound} - \text{nonspecific}}{\text{total} - \text{nonspecific}}$$

where "test compound" refers to the average counts per minute of the test duplicates, "nonspecific" refers to the average counts per minute when no CDK1/Cyclin B, etc., was added, and "total" refers to the average counts per minute when no compound was added. The $IC_{50}$ value is the concentration of test compound that reduces by 50% the protein-kinase induced incorporation of the radiolabel under the test conditions described. The value of the inhibitor constant Ki is calculated by the following: Ki=IC50/(1+[S]/Km), where [S] is the ATP concentration and Km is Michaelis constant.

The Homogeneous Time Resolved Fluorescence (HTRF) kinase assay was carried out in 96-well polypropylene plates (BD Biosciences, Bedford, Mass.). Test compounds were first dissolved in DMSO, and then diluted in kinase assay buffer 1 (25 mM HEPES, pH7.0, 8 mM $MgCl_2$, 1.5 mM DTT, and 162 μM ATP) with DMSO concentration at 15%. The CDK1/Cyclin B enzyme was diluted in kinase assay buffer 2 (25 mM HEPES, pH 7.0, 8 mM $MgCl_2$, 0.003% Tween 20, 0.045% BSA, 1.5 mM DTT, and 0.338 μM Rb protein). To initiate the kinase reaction, 20 μL of compound solution was mixed with 40 μL of CDK1/Cyclin B solution in assay plates with final concentration of CDK1/Cyclin B and Rb at 0.1 μg/mL and 0.113 μM, respectively, and incubated at 37° C. for 30 min. 15 μL of anti-phospho-Rb (Ser 780) antibody (Cell Signaling Technology, Beverly, Mass.,) was added with a 1:7692 dilution of the antibody.

Incubation was continued at 37° C. for 25 min, after which LANCE Eu-W1024 labeled anti-rabbit IgG (1 nm, PerkinElmer, Wellesley, Mass.) and anti-His antibody conjugated to SureLight-Allophucocyanin (20 nM, PerkinElmer, Wellesley, Mass.) were added to the wells. Incubation was continued at 37° C. for another 40 min. At the completion of the incubation, 35 μL of reaction mixture was transferred to fresh 384-well black polystyrene plates (Corning Incorporated, Corning, N.Y.) and read on a fluorescent plate reader at excitation wavelength of 340 nm and emission wavelength of 665/615 nm.

Ki values showing CDK1/Cyclin B activity that applied to compounds of the subject matter of this invention ranges from about 0.001 μM to about 5.000 μM. Specific data for some examples are as follows:

| Example | Ki (μM) |
|---------|---------|
| 5  | 0.039  |
| 10 | 1.185  |
| 15 | 0.21   |
| 20 | 0.032  |
| 25 | 0.34   |
| 30 | 0.281  |
| 35 | 0.0372 |
| 40 | 0.013  |

The invention claimed is:

1. A compound of the formula:

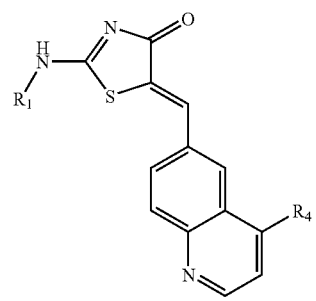

I wherein $R_1$ is hydrogen, lower alkyl, aryloxy-lower alkyl, lower alkoxy-lower alkyl or;

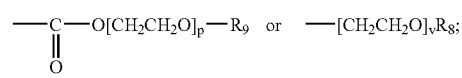

or $R_2$—$(X)_n$—

X is lower alkylene, hydroxyloweralkylene, cycloloweralkylene, aryl lower alkylene, carboxyloweralkylene, hydroxy lower alkylene, amido lower alkylene, mono- or di-halo lower alkylene, amino lower alkylene, mono- or di-lower alkyl amino lower alkylene or imido lower alkylene;

$R_2$ is

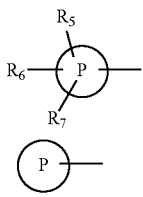

is an aryl ring, cyclolower alkyl ring containing from 3 to 6 carbon atoms, a 4 to 6 membered heterocycloalkyl ring containing from 3 to 5 carbon atoms and from 1 to 2 hetero atoms selected from the group consisting of oxygen, nitrogen and sulfur, or a 5 or 6 membered heteroaromatic ring containing from 1 to 2 hetero atoms selected from the group consisting of oxygen, sulfur and nitrogen; $R_5$, $R_6$ and $R_7$ are independently selected from the group consisting of hydroxy, lower alkyl sulfone, hydroxy-lower alkyl, hydrogen, lower alkyl, halogen, perfluro lower alkyl, lower alkoxy, amino, mono- or di-lower alkyl amino, or when two of the substituents $R_5$, $R_6$ and $R_7$ are substituted on adjacent carbon atoms on ring

, these two substituents can be taken together with their adjacent, attached carbon atoms to form an aryl ring, a 3 to 6 membered cyclolower alkyl ring, a 4 to 6 membered heterocycloalkyl ring or a 4 to 6 membered heteroaromatic ring, said heterocycloalkyl ring and said heteroaromatic ring containing from 1 to 2 hetero atoms selected from the group consisting of oxygen, nitrogen or sulfur;

$R_4$ is halo,

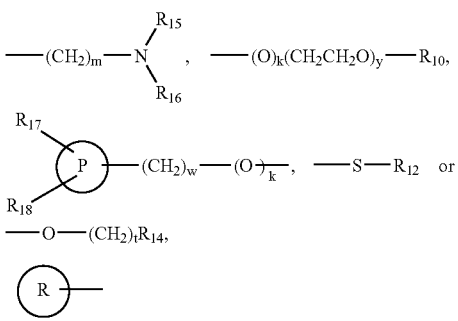

is an aryl ring, a cycloalkyl ring containing from 2 to 6 carbon atoms, a 4 to 6 membered heterocyclic alkyl ring containing from 3 to 5 carbon atoms and from 1 to 2 hetero atoms selected from the group consisting of a oxygen, sulfur and nitrogen or a 5 to 6 numbered heteroaromatic right containing from 1 to 2 hetro atoms selected from the group consisting of oxygen sulfur and nitrogen; $R_8$, $R_9$, $R_{11}$, $R_{15}$ and $R_{16}$ are independently hydrogen or lower alkyl; $R_{10}$ and $R_{12}$, are lower alkyl; $R_{14}$ is perfluro lower alkyl or —N $R_{15}R_{16}$; $R_{17}$ and $R_{18}$ are independently hydrogen, lower alkyl, or

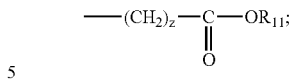

n and k are integers from 0 to 1; m, w, y and z are integers from 0 to 3; p is an integer from 0 to 6 and v and t are integers from 1 to 6;

or pharmaceutically acceptable salts thereof.

2. The compound of claim 1 wherein said compound is:

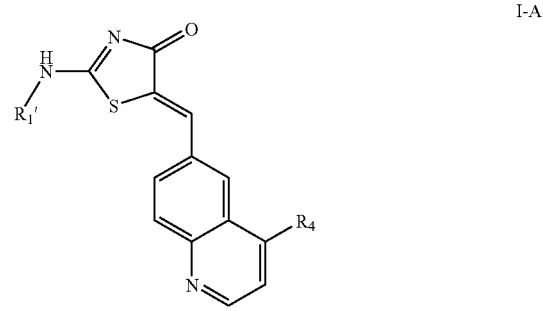

I-A wherein $R_1'$ is hydrogen, lower alkyl, or lower alkoxy-lower alkyl and $R_4$ is as above, or pharmaceutically acceptable salts thereof.

3. The compound of claim 2 wherein aryl is phenyl.

4. The compound of claim 3 wherein $R_1'$ is hydrogen.

5. The compound of claim 4 wherein $R_4'$ is —$(O)_k$ $(CH_2CH_2O)_y$—$R_{10}$; and $R_{10}$, k and y are as above.

6. The compound of claim 5 wherein said compound is 2-amino-5-(4-methoxy-quinolin-6-ylmeth-(Z)-ylidine)-thiazol-4-one.

7. The compound of claim 5 wherein said compound is 2-amino-5-[4-(2-methoxy-ethoxy)-quinolin-6-ylmeth-(Z)-ylidine]-thiazol-4-one.

8. The compound of claim 5 wherein said compound is 2-amino-5-(4-butoxy-quinolin-6-ylmeth-(Z)-ylidine)-thiazol-4-one.

9. The compound of claim 4 where $R_4$ is

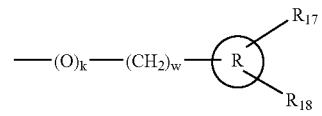

where w, k, (R), $R_{17}$ and $R_{18}$ are as above.

10. The compound of claim 9 wherein w is 0.

11. The compound of claim 10 wherein said compound is 2-amino-5-(4-phenoxy-quinolin-6-ylmeth-(Z)-ylidine)-thiazol-4-one.

12. The compound of claim 10 wherein said compound is 2-amino-5-[1-[4-(piperidin-4-yloxy)-quinolin-6-yl]-meth-(Z)-ylidene]-thiazol-4-one.

13. The compound of claim 9 wherein w is an integer from 1 to 3.

14. The compound of claim 13 wherein said compound is 2-amino-5-{4-[2-(3-methoxyphenyl)-ethoxy]-quinolin-6-ylmeth-(Z)-ylidine}-thiazol-4-one.

15. The compound of claim 13 wherein said compound is 2-amino-5-{4-[2-(4-fluorophenyl)-ethoxy]-quinolin-6-ylmeth-(Z)-ylidine}-thiazol-4-one.

16. The compound of claim 4 wherein $R_4$ is —S—$R_{12}$ and $R_{12}$ is as above.

17. The compound of claim 16 wherein said compound is 2-amino-5-(4-ethylsulfanyl-quinolin-6-ylmeth-(Z)-ylidine)-thiazol-4-one.

18. The compound of claim 4 wherein $R_4$ is —O—($CH_2$)$_r R_{14}$.

19. The compound of claim 18 wherein $R_{14}$ is a perfluro lower alkyl group.

20. The compound of claim 19 wherein $R_{14}$ is trifluoro methyl.

21. The compound of claim 20 wherein said compound is 2-amino-5-[4-(2,2,2-trifluoro-ethoxy)-quinolin-6-ylmeth-(Z)-ylidine]-thiazol-4-one.

22. The compound of claim 1 wherein said compound has the formula:

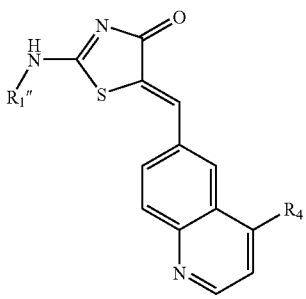

I-B wherein
$R_1''$ is $R_{12}$—(X')$_n$—;
n and $R_4$ are as above; and
X is lower alkylene, hydroxyloweralkylene, cyclolower alkylene, hydroxy lower alkylene, mono- or di-halo lower alkylene;
$R_2$ is

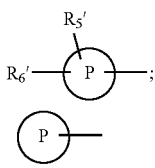

is an aryl ring, cycloalkyl ring containing from 2 to 6 carbon atoms, a 4 to 6 membered heterocycloalkyl ring containing from 3 to 5 carbon atoms and from 1 to 2 hetero atoms selected from the group consisting of oxygen, nitrogen and sulfur, a 5 or 6 membered heteroaromatic ring containing from 1 to 2 hetero atoms selected from the group consisting of oxygen, sulfur and nitrogen;
$R_5'$ and $R_6'$ are independently selected from the group consisting of hydroxy, lower alkyl sulfone, hydroxy-lower alkyl, hydrogen, lower alkyl, halogen, perfluro lower alkyl, lower alkoxy, amino, mono- or di-lower alkyl amino;
or pharmaceutically acceptable salts thereof.

23. The compound of claim 22 wherein aryl is phenyl.

24. The compound of claim 23 wherein n is 1.

25. The compound of claim 24 wherein X' is cycloloweralkylene.

26. The compound of claim 25 wherein said cycloloweralkylene is cyclopropyl.

27. The compound of claim 26 wherein $R_2'$ is phenyl or halophenyl.

28. The compound of claim 27 wherein $R_4$ is —(O)$_k$($CH_2CH_2O$)$_y$—$R_{10}$; and y, k and $R_{10}$ are as above.

29. The compound of claim 28 wherein said compound is 5-(4-methoxy-quinolin-6-ylmeth-(Z)-ylidine)-2-((1R,2S)-2-phenyl-cyclopropylamino)-thiazol-4-one.

30. The compound of claim 28 wherein said compound is 5-(4-ethoxy-quinolin-6-ylmeth-(Z)-ylidine)-2-((1R,2S)-2-phenyl-cyclopropylamino)-thiazol-4-one.

31. The compound of claim 28 wherein said compound is 5-[1-(4-ethoxy-quinolin-6-yl)-meth-(Z)-ylidene]-2-[2-(4-fluoro-phenyl)-cyclopropylamino]-thiazol-4-one.

32. The compound of claim 28 wherein said compound is 5-[4-(2-methoxy-ethoxy)-quinolin-6-ylmeth-(Z)-ylidine]-2-((1R,2S)-2-phenyl-cyclopropylamino)-thiazol-4-one.

33. The compound of claim 28 wherein said compound is 5-(4-butoxy-quinolin-6-ylmeth-(Z)-ylidine)-2-((1R,2S)-2-phenyl-cyclopropylamino)-thiazol-4-one.

34. The compound of claim 26 wherein $R_4$ is halo.

35. The compound of claim 34 wherein compound is 5-(4-chloro-quinolin-6-ylmeth-(Z)-ylidine)-2-((1R,2S)-2-phenyl-cyclopropylamino)-thiazol-4-one.

36. The compound of claim 26 wherein $R_4$ is

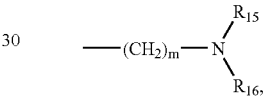

where $R_{15}$, $R_{16}$ and m are as above.

37. The compound of claim 36 wherein said compound is 5-(4-diethylamino-quinolin-6-ylmeth-(Z)-ylidine)-2-((1R,2S)-2-phenyl-cyclopropylamino)-thiazol-4-one.

38. The compound of claim 26 wherein $R_4$ is —S—$R_{12}$.

39. The compound of claim 38 wherein said compound is 5-(4-ethylsulfanyl-quinolin-6-ylmeth-(Z)-ylidine)-2-((1R,2S)-2-phenyl-cyclopropylamino)-thiazol-4-one.

40. The compound of claim 26 wherein $R_4$ is

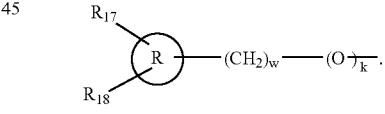

41. The compound of claim 40 wherein k is 1.

42. The compound of claim 41 wherein said compound is 5-(4-cyclohexylmethoxy-quinolin-6-ylmeth-(Z)-ylidine)-2-((1R,2S)-2-phenyl-cyclopropylamino)-thiazol-4-one.

43. The compound of claim 41 wherein said compound is 5-(4-phenoxy-quinolin-6-ylmeth-(Z)-ylidine)-2-((1R,2S)-2-phenyl-cyclopropylamino)-thiazol-4-one.

44. The compound of claim 40 wherein k is 0.

45. The compound of claim 44 wherein said compound is 5-(4-morpholin-4-yl-quinolin-6-ylmeth-(Z)-ylidine)-2-((1R,2S)-2-phenyl-cyclopropylamino)-thiazol-4-one.

46. The compound of claim 22 wherein X' is lower alkylene.

47. The compound of claim 46 wherein the ring Ⓟ is phenyl.

48. The compound of claim 47 wherein $R_4$ is —(O)$_K$($CH_2CH_2O$)$_y$—$R_{10}$.

49. The compound of claim 48 wherein said compound is 2-[2-(2-ethoxy-phenyl)-ethylamino]-5-[1-(4-ethoxy-quinolin-6-yl)-meth-(Z)-ylidene]-thiazol-4-one.

50. The compound of claim 48 wherein said compound is 2-(2-chloro-benzylamino)-5-(4-ethoxy-quinolin-6-ylmeth-(Z)-ylidine)-thiazol-4-one.

51. The compound of claim 48 wherein said compound is 2-(2-chloro-6-methyl-benzylamino)-5-(4-ethoxy-quinolin-6-ylmeth-(Z)-ylidine)-thiazol-4-one.

52. The compound of claim 47 wherein $R_4$ is —O—$(CH_2)_m R_{14}$; and $R_{14}$ and m are as above.

53. The compound of claim 52 wherein said compound is 2-[2-(3-fluorophenyl)-ethylamino]-5-[4-(2,2,2-trifluoro-ethoxy)-quinolin-6-ylmeth-(Z)-ylidine]-thiazol-4-one.

54. The compound of claim 52 wherein said compound is 5-[4-(2-dimethylamino-ethoxy)-quinolin-6-ylmeth-(Z)-ylidine]-2-[2-(3-fluorophenyl)-ethylamino]-thiazol-4-one.

55. The compound of claim 22 wherein $R_4$ is —S—$R_{12}$ and $R_{12}$ is as above.

56. The compound of claim 55 wherein said compound 5-(4-ethylsulfanyl-quinolin-6-ylmeth-(Z)-ylidine)-2-[2-(3-fluorophenyl)-ethylamino]-thiazol-4-one.

57. The compound of claim 46 where the ring

is a heteroaromatic ring.

58. The compound of claim 57 wherein $R_4$ is —$(O)_K(CH_2CH_2O)_y$—$R_{10}$.

59. The compound of claim 58 wherein said compound is 5-(4-methoxy-quinolin-6-ylmeth-(Z)-ylidine)-2-[(thiophen-2-ylmethyl)-amino]-thiazol-4-one.

60. The compound of claim 58 wherein said compound is 5-(4-ethoxy-quinolin-6-ylmeth-(Z)-ylidine)-2-[(thiophen-2-ylmethyl)-amino]-thiazol-4-one.

61. The compound of claim 58 wherein said compound is 5-[4-(2-methoxy-ethoxy)-quinolin-6-ylmeth-(Z)-ylidine]-2-[(thiophen-2-ylmethyl)-amino]-thiazol-4-one.

62. The compound of claim 58 wherein said compound is 2-[(3-methyl-thiophen-2-ylmethyl)-amino]-5-(4-ethoxy-quinolin-6-ylmeth-(Z)-ylidine)-thiazol-4-one.

63. The compound of claim 57 wherein $R_4$ is halo.

64. The compound of claim 63 wherein said compound is 5-(4-chloro-quinolin-6-ylmeth-(Z)-ylidine)-2-[(thiophen-2-ylmethyl)-amino]-thiazol-4-one.

65. The compound of claim 57 wherein $R_4$ is

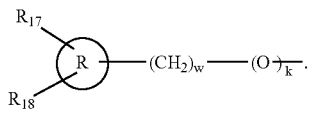

66. The compound of claim 65 wherein said compound is 5-(4-phenoxy-quinolin-6-ylmeth-(Z)-ylidine)-2-[(thiophen-2-ylmethyl)-amino]-thiazol-4-one.

67. The compound of claim 65 wherein said compound is 5-(4-cyclohexylmethoxy-quinolin-6-ylmeth-(Z)-ylidine)-2-[(thiophen-2-ylmethyl)-amino]-thiazol-4-one.

68. The compound of claim 65 wherein said compound is 5-(4-morpholin-4-yl-quinolin-6-ylmeth-(Z)-ylidine)-2-[(thiophen-2-ylmethyl)-amino]-thiazol-4-one.

69. The compound of claim 24 wherein X' is hydroxy lower alkylene.

70. The compound of claim 69 wherein $R_4$ is —$(O)_K(CH_2CH_2O)_y$—$R_{10}$.

71. The compound of claim 70 wherein said compound is 5-(4-ethoxy-quinolin-6-ylmeth-(Z)-ylidine)-2-(2-hydroxy-1-(R)-phenyl-ethylamino)-thiazol-4-one.

72. The compound of claim 70 wherein said compound is 2-(2-hydroxy-1-(R)-phenyl-ethylamino)-5-(4-methoxy-quinolin-6-ylmeth-(Z)-ylidine)-thiazol-4-one.

73. The compound of claim 70 wherein said compound is -[4-(2-methoxy-ethoxy)-quinolin-6-ylmeth-(Z)-ylidine]-2-(2-hydroxy-1-(R)-phenyl-ethylamino)-thiazol-4-one.

74. The compound of claim 69 wherein $R_4$ is

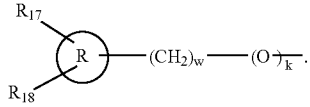

75. The compound of claim 74 wherein said compound is 5-(4-cyclohexylmethoxy-quinolin-6-ylmeth-(Z)-ylidine)-2-(2-hydroxy-1-(R)-phenyl-ethylamino)-thiazol-4-one.

76. The compound of claim 74 wherein said compound is 5-(4-morpholin-4-yl-quinolin-6-ylmeth-(Z)-ylidine)-2-(2-hydroxy-1-(R)-phenyl-ethylamino)-thiazol-4-one.

77. The compound of claim 24 wherein X' is dihalo lower alkylene.

78. The compound of claim 77 wherein $R_1$ is a heteroaromatic ring.

79. The compound of claim 78 wherein $R_4$ is —$(O)_K(CH_2CH_2O)_y$—$R_{10}$.

80. The compound of claim 79 wherein said compound is 2-(2,2-difluoro-2-pyridin-2-yl-ethylamino)-5-[1-(4-ethoxy-quinolin-6-yl)-meth-(Z)-ylidene]-thiazol-4-one; compound with methanesulfonic acid.

* * * * *